United States Patent
Chen et al.

(10) Patent No.: US 10,258,697 B2
(45) Date of Patent: Apr. 16, 2019

(54) EFFICIENT DELIVERY OF THERAPEUTIC MOLECULES IN VITRO AND IN VIVO

(71) Applicant: Massachusetts Eye and Ear Infirmary, Boston, MA (US)

(72) Inventors: Zheng-Yi Chen, Somerville, MA (US); David Liu, Cambridge, MA (US); John Anthony Zuris, Cambridge, MA (US); David B. Thompson, Cambridge, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 15/523,325

(22) PCT Filed: Oct. 29, 2015

(86) PCT No.: PCT/US2015/058096
§ 371 (c)(1),
(2) Date: Apr. 28, 2017

(87) PCT Pub. No.: WO2016/069912
PCT Pub. Date: May 6, 2016

(65) Prior Publication Data
US 2017/0340754 A1 Nov. 30, 2017

Related U.S. Application Data

(60) Provisional application No. 62/072,209, filed on Oct. 29, 2014.

(51) Int. Cl.

| | | |
|---|---|---|
| C12N 15/11 | (2006.01) | |
| A61K 48/00 | (2006.01) | |
| C12N 15/87 | (2006.01) | |
| C12N 5/0793 | (2010.01) | |
| A61K 38/00 | (2006.01) | |
| C12N 15/88 | (2006.01) | |
| C12N 9/22 | (2006.01) | |
| C12N 15/113 | (2010.01) | |
| C12N 15/90 | (2006.01) | |
| A61K 9/127 | (2006.01) | |
| C07J 7/00 | (2006.01) | |
| C07K 7/06 | (2006.01) | |
| C07K 7/08 | (2006.01) | |
| C07K 14/46 | (2006.01) | |
| C07K 14/47 | (2006.01) | |
| C07K 19/00 | (2006.01) | |
| C12N 9/52 | (2006.01) | |
| A61K 38/10 | (2006.01) | |
| C12N 9/00 | (2006.01) | |
| A61K 47/64 | (2017.01) | |
| A61K 47/69 | (2017.01) | |

(52) U.S. Cl.
CPC ........ *A61K 48/0008* (2013.01); *A61K 9/1272* (2013.01); *A61K 38/00* (2013.01); *A61K 38/10* (2013.01); *A61K 47/64* (2017.08); *A61K 47/6911* (2017.08); *A61K 48/0075* (2013.01); *A61K 48/0083* (2013.01); *C07J 7/009* (2013.01); *C07K 7/06* (2013.01); *C07K 7/08* (2013.01); *C07K 14/463* (2013.01); *C07K 14/47* (2013.01); *C07K 19/00* (2013.01); *C12N 5/062* (2013.01); *C12N 9/00* (2013.01); *C12N 9/22* (2013.01); *C12N 9/52* (2013.01); *C12N 15/11* (2013.01); *C12N 15/113* (2013.01); *C12N 15/87* (2013.01); *C12N 15/88* (2013.01); *C12N 15/907* (2013.01); *C12Y 304/2207* (2013.01); *C07K 2319/06* (2013.01); *C07K 2319/21* (2013.01); *C07K 2319/33* (2013.01); *C07K 2319/60* (2013.01); *C12N 2310/20* (2017.05); *C12N 2310/3513* (2013.01); *C12N 2510/00* (2013.01)

(58) Field of Classification Search
None
See application file for complete search history.

(56) References Cited

U.S. PATENT DOCUMENTS

2014/0242699 A1 * 8/2014 Zhang ................ C12N 15/86
435/455

OTHER PUBLICATIONS

Simeon et al in "Discovery and Characterization of a New Cell-Penetrating Protein" (ACS Chem Biol. 2013 vol. 8, No. 12.: pp. 1-21). (Year: 2013).*

Cronican et al. in "Potent delivery of functional proteins into Mammalian cells in vitro and in vivo using a supercharged protein". ACS Chem Biol 2010, vol. 5 No. 8: pp. 747-752; 2010). (Year: 2010).*

* cited by examiner

*Primary Examiner* — Catherine S Hibbert
(74) *Attorney, Agent, or Firm* — Mintz Levin Cohn Ferris Glovsky and Popeo, P.C.; Ingrid A. Beattie; Nicholas A. Zachariades

(57) ABSTRACT

Compositions are described for direct protein delivery into multiple cell types in the mammalian inner ear. The compositions are used to deliver protein(s) (such as gene editing factors) editing of genetic mutations associated with deafness or associated disorders thereof. The delivery of genome editing proteins for gene editing and correction of genetic mutations protect or restore hearing from genetic deafness. Methods of treatment include the intracellular delivery of these molecules to a specific therapeutic target.

4 Claims, 15 Drawing Sheets
Specification includes a Sequence Listing.

TCAAGGCTGTGCAGATGCTCTGGGTGAACCTCATCATGGACACGTTGCCTCCCGGCCCGGCCAGAGCCACCTAGGAGAGACTGCTTCGA  
AGTTCCGAGACGTTCTACGAGACCACCACTTGGAGTAGTCCTGTGCAAGGGAGGGACCGGGACCGGTGTCGGTGATGCTCTGAGACGAAGACT

| | 2,910 2,920 2,930 2,940 2,950 2,960 2,970 2,980 2,990 3,000 | |
|---|---|---|
| T7pro.PMCA2-1 | TAATACGACTCACTATAGGG CAAGGCTGTGCAGATGCTCT GTTTTAGAGCTAGAAATAGC | SEQ ID NO: 22 |
| T7pro.PMCA2-2 | TAATACGACTCACTATAGG GCTCTGGGTGAACCTCATCA GTTTTAGAGCTAGAAATAGCA | SEQ ID NO: 23 |
| T7pro.PMCA2-3 | TAATACGACTCACTATAGGG AGGGCAAACGTGTCCATGATG GTTTTAGAGCTAGAAATAGC | SEQ ID NO: 24 |
| T7pro.PMCA2-4wt | TAATACGACTCACTATAGGG CATGGACACGTTTGCCTCCC GTTTTAGAGCTAGAAATAGC | SEQ ID NO: 25 |
| T7pro.PMCA2-4mut | TAATACGACTCACTATAGGG CATGGACACGTTTGCCTTCC GTTTTAGAGCTAGAAATAGC | SEQ ID NO: 26 |
| T7pro.PMCA2-5wt | TAATACGACTCACTATAGGG CACGTTTGCCTCCCGGCCC GTTTTAGAGCTAGAAATAGC | SEQ ID NO: 27 |
| T7pro.PMCA2-5mut | TAATACGACTCACTATAGGG CACGTTTGCCTTCCTGGCCC GTTTTAGAGCTAGAAATAGC | SEQ ID NO: 28 |
| T7pro.PMCA2-6wt | TAATACGACTCACTATAGGG CTCTGTGGCCAGGGCCAGGG GTTTTAGAGCTAGAAATAGC | SEQ ID NO: 29 |
| T7pro.PMCA2-6mut | TAATACGACTCACTATAGGG CTCTGTGGCCAGGGCCAGG GTTTTAGAGCTAGAAATAGC | SEQ ID NO: 30 |
| T7pro.PMCA2-7wtPAM | TAATACGACTCACTATAGGG TGGCTCTGTGGCCAGGGCCA GTTTTAGAGCTAGAAATAGC | SEQ ID NO: 31 |
| T7pro.PMCA2-8 | TAATACGACTCACTATAGGG CCTGGCCACAGAGCCACCTA GTTTTAGAGCTAGAAATAGC | SEQ ID NO: 32 |
| T7pro.PMCA2-9 | TAATACGACTCACTATAGGG CTACGGAGAGCTTGCTTCTG GTTTTAGAGCTAGAAATAGC | SEQ ID NO: 33 |

FIG. 2

FIG. 7A  FIG. 7B
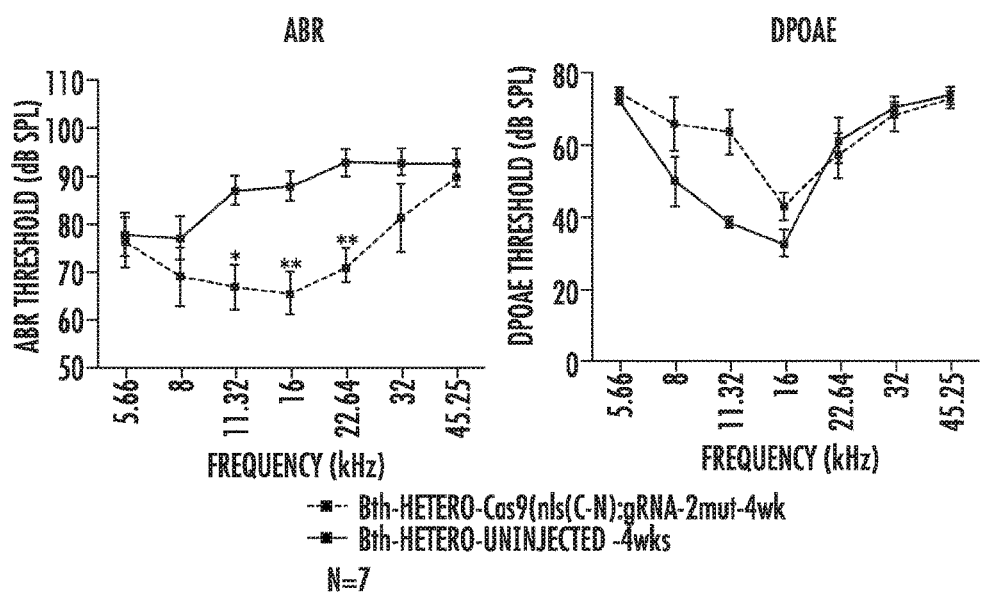
FIG. 8 tdT/Myo7a/Sox2/

SEQUENCE LISTING

```
<160> NUMBER OF SEQ ID NOS: 102

<210> SEQ ID NO 1
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
    130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
```

```
                180              185              190
Gly Pro Val Leu Leu Pro Arg Asn His Tyr Leu Ser Thr Arg Ser Lys
            195              200              205
Leu Ser Lys Asp Pro Lys Glu Lys Arg Asp His Met Val Leu Leu Glu
        210              215              220
Phe Val Thr Ala Ala Gly Ile Lys His Gly Arg Asp Glu Arg Tyr Lys
225              230              235              240
Thr Gly Gly Ser Gly Gly Ser Gly Gly Ser Gly Gly Ser Gly Gly Ser
                245              250              255
Gly Gly Ser Gly Gly Ser Gly Gly Ser Gly Gly Thr Ala Ser Asn Leu
            260              265              270
Leu Thr Val His Gln Asn Leu Pro Ala Leu Pro Val Asp Ala Thr Ser
        275              280              285
Asp Glu Val Arg Lys Asn Leu Met Asp Met Phe Arg Asp Arg Gln Ala
        290              295              300
Phe Ser Glu His Thr Trp Lys Met Leu Leu Ser Val Cys Arg Ser Trp
305              310              315              320
Ala Ala Trp Cys Lys Leu Asn Asn Arg Lys Trp Phe Pro Ala Glu Pro
            325              330              335
Glu Asp Val Arg Asp Tyr Leu Leu Tyr Leu Gln Ala Arg Gly Leu Ala
            340              345              350
Val Lys Thr Ile Gln Gln His Leu Gly Gln Leu Asn Met Leu His Arg
            355              360              365
Arg Ser Gly Leu Pro Arg Pro Ser Asp Ser Asn Ala Val Ser Leu Val
        370              375              380
Met Arg Arg Ile Arg Lys Glu Asn Val Asp Ala Gly Glu Arg Ala Lys
385              390              395              400
Gln Ala Leu Ala Phe Glu Arg Thr Asp Phe Asp Gln Val Arg Ser Leu
                405              410              415
Met Glu Asn Ser Asp Arg Cys Gln Asp Ile Arg Asn Leu Ala Phe Leu
            420              425              430
Gly Ile Ala Tyr Asn Thr Leu Leu Arg Ile Ala Glu Ile Ala Arg Ile
        435              440              445
Arg Val Lys Asp Ile Ser Arg Thr Asp Gly Gly Arg Met Leu Ile His
        450              455              460
Ile Gly Arg Thr Lys Thr Leu Val Ser Thr Ala Gly Val Glu Lys Ala
465              470              475              480
Leu Ser Leu Gly Val Thr Lys Leu Val Glu Arg Trp Ile Ser Val Ser
                485              490              495
Gly Val Ala Asp Asp Pro Asn Asn Tyr Leu Phe Cys Arg Val Arg Lys
            500              505              510
Asn Gly Val Ala Ala Pro Ser Ala Thr Ser Gln Leu Ser Thr Arg Ala
            515              520              525
Leu Glu Gly Ile Phe Glu Ala Thr His Arg Leu Ile Tyr Gly Ala Lys
            530              535              540
Asp Asp Ser Gly Gln Arg Tyr Leu Ala Trp Ser Gly His Ser Ala Arg
545              550              555              560
Val Gly Ala Ala Arg Asp Met Ala Arg Ala Gly Val Ser Ile Pro Glu
                565              570              575
Ile Met Gln Ala Gly Gly Trp Thr Asn Val Asn Ile Val Met Asn Tyr
            580              585              590
Ile Arg Asn Leu Asp Ser Glu Thr Gly Ala Met Val Arg Leu Leu Glu
            595              600              605
```

```
Asp Gly Asp Gly Gly Ser His His His His His
610                 615                 620

<210> SEQ ID NO 2
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Ala Ser Lys Gly Glu Glu Leu Phe Thr Gly Val Val Pro Ile
1               5                   10                  15

Leu Val Glu Leu Asp Gly Asp Val Asn Gly His Lys Phe Ser Val Arg
            20                  25                  30

Gly Glu Gly Glu Gly Asp Ala Thr Asn Gly Lys Leu Thr Leu Lys Phe
        35                  40                  45

Ile Cys Thr Thr Gly Lys Leu Pro Val Pro Trp Pro Thr Leu Val Thr
50                  55                  60

Thr Leu Thr Tyr Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
130                 135                 140

Tyr Asn Phe Asn Ser His Asn Val Tyr Ile Thr Ala Asp Lys Gln Lys
145                 150                 155                 160

Asn Gly Ile Lys Ala Asn Phe Lys Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
210                 215                 220

Phe Val Thr Ala Ala Gly Ile Thr His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
```

340                 345                 350
        Val Lys Thr Ile Gln Gln His Leu Gly Gln Leu Asn Met Leu His Arg
                355                 360                 365

Arg Ser Gly Leu Pro Arg Pro Ser Asp Ser Asn Ala Val Ser Leu Val
            370                 375                 380

Met Arg Arg Ile Arg Lys Glu Asn Val Asp Ala Gly Glu Arg Ala Lys
        385                 390                 395                 400

Gln Ala Leu Ala Phe Glu Arg Thr Asp Phe Asp Gln Val Arg Ser Leu
                        405                 410                 415

Met Glu Asn Ser Asp Arg Cys Gln Asp Ile Arg Asn Leu Ala Phe Leu
                    420                 425                 430

Gly Ile Ala Tyr Asn Thr Leu Leu Arg Ile Ala Glu Ile Ala Arg Ile
                435                 440                 445

Arg Val Lys Asp Ile Ser Arg Thr Asp Gly Gly Arg Met Leu Ile His
            450                 455                 460

Ile Gly Arg Thr Lys Thr Leu Val Ser Thr Ala Gly Val Glu Lys Ala
        465                 470                 475                 480

Leu Ser Leu Gly Val Thr Lys Leu Val Glu Arg Trp Ile Ser Val Ser
                        485                 490                 495

Gly Val Ala Asp Asp Pro Asn Asn Tyr Leu Phe Cys Arg Val Arg Lys
                    500                 505                 510

Asn Gly Val Ala Ala Pro Ser Thr Ser Gln Leu Ser Thr Arg Ala
                515                 520                 525

Leu Glu Gly Ile Phe Glu Ala Thr His Arg Leu Ile Tyr Gly Ala Lys
            530                 535                 540

Asp Asp Ser Gly Gln Arg Tyr Leu Ala Trp Ser His Ser Ala Arg
        545                 550                 555                 560

Val Gly Ala Ala Arg Asp Met Ala Arg Ala Gly Val Ser Ile Pro Glu
                        565                 570                 575

Ile Met Gln Ala Gly Gly Trp Thr Asn Val Asn Ile Val Met Asn Tyr
                    580                 585                 590

Ile Arg Asn Leu Asp Ser Glu Thr Gly Ala Met Val Arg Leu Leu Glu
                595                 600                 605

Asp Gly Asp Gly Gly Ser His His His His His
            610                 615                 620

<210> SEQ ID NO 3
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Ala Ser Lys Gly Glu Glu Leu Phe Thr Gly Val Val Pro Ile
        1               5                   10                  15

Leu Val Glu Leu Asp Gly Asp Val Asn Gly His Lys Phe Ser Val Arg
                        20                  25                  30

Gly Glu Gly Glu Gly Asp Ala Thr Asn Gly Lys Leu Thr Leu Lys Phe
                    35                  40                  45

Ile Cys Thr Thr Gly Lys Leu Pro Val Pro Trp Pro Thr Leu Val Thr
                50                  55                  60

Thr Leu Thr Tyr Gly Val Gln Cys Phe Ser Arg Tyr Pro Asp His Met
        65                  70                  75                  80

```
Asp Gln His Asp Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
            115                 120                 125

Gly Ile Asp Phe Lys Glu Asp Gly Asn Ile Leu Gly His Lys Leu Glu
130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
            195                 200                 205

Leu Ser Lys Asp Pro Asn Glu Asp Arg Asp His Met Val Leu Leu Glu
210                 215                 220

Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
            275                 280                 285

Asp Glu Val Arg Lys Asn Leu Met Asp Met Phe Arg Asp Arg Gln Ala
            290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
            355                 360                 365

Arg Ser Gly Leu Pro Arg Pro Ser Asp Ser Asn Ala Val Ser Leu Val
370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
            435                 440                 445

Arg Val Lys Asp Ile Ser Arg Thr Asp Gly Gly Arg Met Leu Ile His
            450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
```

```
                    500                 505                 510
Asn Gly Val Ala Ala Pro Ser Ala Thr Ser Gln Leu Ser Thr Arg Ala
            515                 520                 525

Leu Glu Gly Ile Phe Glu Ala Thr His Arg Leu Ile Tyr Gly Ala Lys
        530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605

Asp Gly Asp Gly Gly Ser His His His His His His
610                 615                 620

<210> SEQ ID NO 4
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240
```

```
Thr Gly Gly Ser Gly Gly Ser Gly Gly Ser Gly Gly Ser
            245                 250                 255

Gly Gly Ser Gly Gly Ser Gly Gly Ser Gly Thr Ala Ser Asn Leu
            260                 265                 270

Leu Thr Val His Gln Asn Leu Pro Ala Leu Pro Val Asp Ala Thr Ser
            275                 280                 285

Asp Glu Val Arg Lys Asn Leu Met Asp Met Phe Arg Asp Arg Gln Ala
290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
            355                 360                 365

Arg Ser Gly Leu Pro Arg Pro Ser Asp Ser Asn Ala Val Ser Leu Val
            370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
            435                 440                 445

Arg Val Lys Asp Ile Ser Arg Thr Asp Gly Gly Arg Met Leu Ile His
450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
            515                 520                 525

Leu Glu Gly Ile Phe Glu Ala Thr His Arg Leu Ile Tyr Gly Ala Lys
            530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
            595                 600                 605

Asp Gly Asp Gly Gly Ser His His His His His
            610                 615                 620

<210> SEQ ID NO 5
<211> LENGTH: 353
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 5

```
Met Ala Ser Asn Leu Leu Thr Val His Gln Asn Leu Pro Ala Leu Pro
1               5                   10                  15

Val Asp Ala Thr Ser Asp Glu Val Arg Lys Asn Leu Met Asp Met Phe
            20                  25                  30

Arg Asp Arg Gln Ala Phe Ser Glu His Thr Trp Lys Met Leu Leu Ser
        35                  40                  45

Val Cys Arg Ser Trp Ala Ala Trp Cys Lys Leu Asn Asn Arg Lys Trp
    50                  55                  60

Phe Pro Ala Glu Pro Glu Asp Val Arg Asp Tyr Leu Leu Tyr Leu Gln
65                  70                  75                  80

Ala Arg Gly Leu Ala Val Lys Thr Ile Gln Gln His Leu Gly Gln Leu
                85                  90                  95

Asn Met Leu His Arg Arg Ser Gly Leu Pro Arg Pro Ser Asp Ser Asn
            100                 105                 110

Ala Val Ser Leu Val Met Arg Arg Ile Arg Lys Glu Asn Val Asp Ala
        115                 120                 125

Gly Glu Arg Ala Lys Gln Ala Leu Ala Phe Glu Arg Thr Asp Phe Asp
130                 135                 140

Gln Val Arg Ser Leu Met Glu Asn Ser Asp Arg Cys Gln Asp Ile Arg
145                 150                 155                 160

Asn Leu Ala Phe Leu Gly Ile Ala Tyr Asn Thr Leu Leu Arg Ile Ala
                165                 170                 175

Glu Ile Ala Arg Ile Arg Val Lys Asp Ile Ser Arg Thr Asp Gly Gly
            180                 185                 190

Arg Met Leu Ile His Ile Gly Arg Thr Lys Thr Leu Val Ser Thr Ala
        195                 200                 205

Gly Val Glu Lys Ala Leu Ser Leu Gly Val Thr Lys Leu Val Glu Arg
210                 215                 220

Trp Ile Ser Val Ser Gly Val Ala Asp Asp Pro Asn Asn Tyr Leu Phe
225                 230                 235                 240

Cys Arg Val Arg Lys Asn Gly Val Ala Ala Pro Ser Ala Thr Ser Gln
                245                 250                 255

Leu Ser Thr Arg Ala Leu Glu Gly Ile Phe Glu Ala Thr His Arg Leu
            260                 265                 270

Ile Tyr Gly Ala Lys Asp Asp Ser Gly Gln Arg Tyr Leu Ala Trp Ser
        275                 280                 285

Gly His Ser Ala Arg Val Gly Ala Ala Arg Asp Met Ala Arg Ala Gly
290                 295                 300

Val Ser Ile Pro Glu Ile Met Gln Ala Gly Gly Trp Thr Asn Val Asn
305                 310                 315                 320

Ile Val Met Asn Tyr Ile Arg Asn Leu Asp Ser Glu Thr Gly Ala Met
                325                 330                 335

Val Arg Leu Leu Glu Asp Gly Asp Gly Ser His His His His
            340                 345                 350

His
```

<210> SEQ ID NO 6
<211> LENGTH: 1368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg

```
                820             825             830
Leu Ser Asp Tyr Asp Val Asp His Ile Val Pro Gln Ser Phe Leu Lys
            835             840             845
Asp Asp Ser Ile Asp Asn Lys Val Leu Thr Arg Ser Asp Lys Asn Arg
850             855             860
Gly Lys Ser Asp Asn Val Pro Ser Glu Glu Val Val Lys Lys Met Lys
865             870             875             880
Asn Tyr Trp Arg Gln Leu Leu Asn Ala Lys Leu Ile Thr Gln Arg Lys
            885             890             895
Phe Asp Asn Leu Thr Lys Ala Glu Arg Gly Gly Leu Ser Glu Leu Asp
            900             905             910
Lys Ala Gly Phe Ile Lys Arg Gln Leu Val Glu Thr Arg Gln Ile Thr
            915             920             925
Lys His Val Ala Gln Ile Leu Asp Ser Arg Met Asn Thr Lys Tyr Asp
            930             935             940
Glu Asn Asp Lys Leu Ile Arg Glu Val Lys Val Ile Thr Leu Lys Ser
945             950             955             960
Lys Leu Val Ser Asp Phe Arg Lys Asp Phe Gln Phe Tyr Lys Val Arg
            965             970             975
Glu Ile Asn Asn Tyr His His Ala His Asp Ala Tyr Leu Asn Ala Val
            980             985             990
Val Gly Thr Ala Leu Ile Lys Lys Tyr Pro Lys Leu Glu Ser Glu Phe
            995             1000            1005
Val Tyr Gly Asp Tyr Lys Val Tyr Asp Val Arg Lys Met Ile Ala
            1010            1015            1020
Lys Ser Glu Gln Glu Ile Gly Lys Ala Thr Ala Lys Tyr Phe Phe
            1025            1030            1035
Tyr Ser Asn Ile Met Asn Phe Phe Lys Thr Glu Ile Thr Leu Ala
            1040            1045            1050
Asn Gly Glu Ile Arg Lys Arg Pro Leu Ile Glu Thr Asn Gly Glu
            1055            1060            1065
Thr Gly Glu Ile Val Trp Asp Lys Gly Arg Asp Phe Ala Thr Val
            1070            1075            1080
Arg Lys Val Leu Ser Met Pro Gln Val Asn Ile Val Lys Lys Thr
            1085            1090            1095
Glu Val Gln Thr Gly Gly Phe Ser Lys Glu Ser Ile Leu Pro Lys
            1100            1105            1110
Arg Asn Ser Asp Lys Leu Ile Ala Arg Lys Lys Asp Trp Asp Pro
            1115            1120            1125
Lys Lys Tyr Gly Gly Phe Asp Ser Pro Thr Val Ala Tyr Ser Val
            1130            1135            1140
Leu Val Val Ala Lys Val Glu Lys Gly Lys Ser Lys Lys Leu Lys
            1145            1150            1155
Ser Val Lys Glu Leu Leu Gly Ile Thr Ile Met Glu Arg Ser Ser
            1160            1165            1170
Phe Glu Lys Asn Pro Ile Asp Phe Leu Glu Ala Lys Gly Tyr Lys
            1175            1180            1185
Glu Val Lys Lys Asp Leu Ile Ile Lys Leu Pro Lys Tyr Ser Leu
            1190            1195            1200
Phe Glu Leu Glu Asn Gly Arg Lys Arg Met Leu Ala Ser Ala Gly
            1205            1210            1215
Glu Leu Gln Lys Gly Asn Glu Leu Ala Leu Pro Ser Lys Tyr Val
            1220            1225            1230
```

-continued

```
Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 7
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
                35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
```

-continued

```
                210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640
```

```
His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050
```

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

His His His His His His
    1370

<210> SEQ ID NO 8
<211> LENGTH: 1382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Pro Lys Lys Lys Arg Lys Val Met Asp Lys Lys Tyr Ser Ile Gly
1               5                   10                  15

```
Leu Ala Ile Gly Thr Asn Ser Val Gly Trp Ala Val Ile Thr Asp Glu
            20                  25                  30

Tyr Lys Val Pro Ser Lys Lys Phe Lys Val Leu Gly Asn Thr Asp Arg
        35                  40                  45

His Ser Ile Lys Lys Asn Leu Ile Gly Ala Leu Leu Phe Asp Ser Gly
 50                  55                  60

Glu Thr Ala Glu Ala Thr Arg Leu Lys Arg Thr Ala Arg Arg Arg Tyr
 65                  70                  75                  80

Thr Arg Arg Lys Asn Arg Ile Cys Tyr Leu Gln Glu Ile Phe Ser Asn
                 85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
            115                 120                 125

Asn Ile Val Asp Glu Val Ala Tyr His Glu Lys Tyr Pro Thr Ile Tyr
            130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
            195                 200                 205

Ile Asn Ala Ser Gly Val Asp Ala Lys Ala Ile Leu Ser Ala Arg Leu
            210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Leu Asp Asn Leu Leu Ala
            275                 280                 285

Gln Ile Gly Asp Gln Tyr Ala Asp Leu Phe Leu Ala Ala Lys Asn Leu
            290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
            340                 345                 350

Glu Lys Tyr Lys Glu Ile Phe Phe Asp Gln Ser Lys Asn Gly Tyr Ala
            355                 360                 365

Gly Tyr Ile Asp Gly Gly Ala Ser Gln Glu Glu Phe Tyr Lys Phe Ile
            370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
            420                 425                 430
```

-continued

```
Arg Gln Glu Asp Phe Tyr Pro Phe Leu Lys Asp Asn Arg Glu Lys Ile
            435                 440                 445

Glu Lys Ile Leu Thr Phe Arg Ile Pro Tyr Tyr Val Gly Pro Leu Ala
    450                 455                 460

Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala
                485                 490                 495

Gln Ser Phe Ile Glu Arg Met Thr Asn Phe Asp Lys Asn Leu Pro Asn
                500                 505                 510

Glu Lys Val Leu Pro Lys His Ser Leu Leu Tyr Glu Tyr Phe Thr Val
            515                 520                 525

Tyr Asn Glu Leu Thr Lys Val Lys Tyr Val Thr Glu Gly Met Arg Lys
530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                565                 570                 575

Phe Lys Lys Ile Glu Cys Phe Asp Ser Val Glu Ile Ser Gly Val Glu
                580                 585                 590

Asp Arg Phe Asn Ala Ser Leu Gly Thr Tyr His Asp Leu Leu Lys Ile
            595                 600                 605

Ile Lys Asp Lys Asp Phe Leu Asp Asn Glu Glu Asn Glu Asp Ile Leu
        610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                645                 650                 655

Lys Gln Leu Lys Arg Arg Arg Tyr Thr Gly Trp Gly Arg Leu Ser Arg
            660                 665                 670

Lys Leu Ile Asn Gly Ile Arg Asp Lys Gln Ser Gly Lys Thr Ile Leu
        675                 680                 685

Asp Phe Leu Lys Ser Asp Gly Phe Ala Asn Arg Asn Phe Met Gln Leu
690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                725                 730                 735

Gly Ser Pro Ala Ile Lys Lys Gly Ile Leu Gln Thr Val Lys Val Val
            740                 745                 750

Asp Glu Leu Val Lys Val Met Gly Arg His Lys Pro Glu Asn Ile Val
        755                 760                 765

Ile Glu Met Ala Arg Glu Asn Gln Thr Thr Gln Lys Gly Gln Lys Asn
    770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                805                 810                 815

Glu Lys Leu Tyr Leu Tyr Tyr Leu Gln Asn Gly Arg Asp Met Tyr Val
            820                 825                 830

Asp Gln Glu Leu Asp Ile Asn Arg Leu Ser Asp Tyr Asp Val Asp His
        835                 840                 845

Ile Val Pro Gln Ser Phe Leu Lys Asp Asp Ser Ile Asp Asn Lys Val
```

```
                850              855              860
Leu Thr Arg Ser Asp Lys Asn Arg Gly Lys Ser Asp Asn Val Pro Ser
865              870              875              880

Glu Glu Val Val Lys Lys Met Lys Asn Tyr Trp Arg Gln Leu Leu Asn
                885              890              895

Ala Lys Leu Ile Thr Gln Arg Lys Phe Asp Asn Leu Thr Lys Ala Glu
                900              905              910

Arg Gly Gly Leu Ser Glu Leu Asp Lys Ala Gly Phe Ile Lys Arg Gln
                915              920              925

Leu Val Glu Thr Arg Gln Ile Thr Lys His Val Ala Gln Ile Leu Asp
                930              935              940

Ser Arg Met Asn Thr Lys Tyr Asp Glu Asn Asp Lys Leu Ile Arg Glu
945              950              955              960

Val Lys Val Ile Thr Leu Lys Ser Lys Leu Val Ser Asp Phe Arg Lys
                965              970              975

Asp Phe Gln Phe Tyr Lys Val Arg Glu Ile Asn Asn Tyr His His Ala
                980              985              990

His Asp Ala Tyr Leu Asn Ala Val Val Gly Thr Ala Leu Ile Lys Lys
        995              1000             1005

Tyr Pro Lys Leu Glu Ser Glu Phe Val Tyr Gly Asp Tyr Lys Val
    1010             1015             1020

Tyr Asp Val Arg Lys Met Ile Ala Lys Ser Glu Gln Glu Ile Gly
    1025             1030             1035

Lys Ala Thr Ala Lys Tyr Phe Phe Tyr Ser Asn Ile Met Asn Phe
    1040             1045             1050

Phe Lys Thr Glu Ile Thr Leu Ala Asn Gly Glu Ile Arg Lys Arg
    1055             1060             1065

Pro Leu Ile Glu Thr Asn Gly Glu Thr Gly Glu Ile Val Trp Asp
    1070             1075             1080

Lys Gly Arg Asp Phe Ala Thr Val Arg Lys Val Leu Ser Met Pro
    1085             1090             1095

Gln Val Asn Ile Val Lys Lys Thr Glu Val Gln Thr Gly Gly Phe
    1100             1105             1110

Ser Lys Glu Ser Ile Leu Pro Lys Arg Asn Ser Asp Lys Leu Ile
    1115             1120             1125

Ala Arg Lys Lys Asp Trp Asp Pro Lys Lys Tyr Gly Gly Phe Asp
    1130             1135             1140

Ser Pro Thr Val Ala Tyr Ser Val Leu Val Val Ala Lys Val Glu
    1145             1150             1155

Lys Gly Lys Ser Lys Lys Leu Lys Ser Val Lys Glu Leu Leu Gly
    1160             1165             1170

Ile Thr Ile Met Glu Arg Ser Ser Phe Glu Lys Asn Pro Ile Asp
    1175             1180             1185

Phe Leu Glu Ala Lys Gly Tyr Lys Glu Val Lys Lys Asp Leu Ile
    1190             1195             1200

Ile Lys Leu Pro Lys Tyr Ser Leu Phe Glu Leu Glu Asn Gly Arg
    1205             1210             1215

Lys Arg Met Leu Ala Ser Ala Gly Glu Leu Gln Lys Gly Asn Glu
    1220             1225             1230

Leu Ala Leu Pro Ser Lys Tyr Val Asn Phe Leu Tyr Leu Ala Ser
    1235             1240             1245

His Tyr Glu Lys Leu Lys Gly Ser Pro Glu Asp Asn Glu Gln Lys
    1250             1255             1260
```

Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305

Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp His His His His His
    1370                1375                1380

<210> SEQ ID NO 9
<211> LENGTH: 1384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn

```
                225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
```

-continued

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

```
Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Pro Lys Lys Lys Arg Lys Val Met Asp Lys His His His His His
    1370                1375                1380

His

<210> SEQ ID NO 10
<211> LENGTH: 1653
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Ala Ser Lys Gly Glu Arg Leu Phe Arg Gly Lys Val Pro Ile
1               5                   10                  15
```

-continued

| | | | | | | | | | | | | |
|---|---|---|---|---|---|---|---|---|---|---|---|---|
|Leu|Val|Glu|Leu|Lys|Gly|Asp|Val|Asn|Gly|His|Lys|Phe|Ser|Val|Arg|
| | | |20 | | | |25 | | | |30 | | |

Gly Lys Gly Lys Gly Asp Ala Thr Arg Gly Lys Leu Thr Leu Lys Phe
            35                  40                  45

Ile Cys Thr Thr Gly Lys Leu Pro Val Pro Trp Pro Thr Leu Val Thr
 50                  55                  60

Thr Leu Thr Ser Gly Val Gln Cys Phe Ser Arg Tyr Pro Lys His Met
 65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
             100                 105                 110

Glu Val Lys Phe Glu Gly Arg Thr Leu Val Asn Arg Ile Lys Leu Lys
             115                 120                 125

Gly Arg Asp Phe Lys Glu Lys Gly Asn Ile Leu Gly His Lys Leu Arg
        130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
            195                 200                 205

Leu Ser Lys Asp Pro Lys Glu Lys Arg Asp His Met Val Leu Leu Glu
210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser
            245                 250                 255

Gly Gly Ser Gly Gly Ser Gly Gly Thr Ala Leu Ala Leu
            260                 265                 270

Pro Lys Lys Lys Arg Lys Val Met Asp Lys Lys Tyr Ser Ile Gly Leu
            275                 280                 285

Asp Ile Gly Thr Asn Ser Val Gly Trp Ala Val Ile Thr Asp Glu Tyr
        290                 295                 300

Lys Val Pro Ser Lys Lys Phe Lys Val Leu Gly Asn Thr Asp Arg His
305                 310                 315                 320

Ser Ile Lys Lys Asn Leu Ile Gly Ala Leu Leu Phe Asp Ser Gly Glu
                325                 330                 335

Thr Ala Glu Ala Thr Arg Leu Lys Arg Thr Ala Arg Arg Arg Tyr Thr
            340                 345                 350

Arg Arg Lys Asn Arg Ile Cys Tyr Leu Gln Glu Ile Phe Ser Asn Glu
        355                 360                 365

Met Ala Lys Val Asp Asp Ser Phe Phe His Arg Leu Glu Glu Ser Phe
370                 375                 380

Leu Val Glu Glu Asp Lys Lys His Glu Arg His Pro Ile Phe Gly Asn
385                 390                 395                 400

Ile Val Asp Glu Val Ala Tyr His Glu Lys Tyr Pro Thr Ile Tyr His
                405                 410                 415

Leu Arg Lys Lys Leu Val Asp Ser Thr Asp Lys Ala Asp Leu Arg Leu
            420                 425                 430

Ile Tyr Leu Ala Leu Ala His Met Ile Lys Phe Arg Gly His Phe Leu

```
            435                 440                 445
Ile Glu Gly Asp Leu Asn Pro Asp Asn Ser Asp Val Asp Lys Leu Phe
    450                 455                 460

Ile Gln Leu Val Gln Thr Tyr Asn Gln Leu Phe Glu Glu Asn Pro Ile
465                 470                 475                 480

Asn Ala Ser Gly Val Asp Ala Lys Ala Ile Leu Ser Ala Arg Leu Ser
                485                 490                 495

Lys Ser Arg Arg Leu Glu Asn Leu Ile Ala Gln Leu Pro Gly Glu Lys
            500                 505                 510

Lys Asn Gly Leu Phe Gly Asn Leu Ile Ala Leu Ser Leu Gly Leu Thr
            515                 520                 525

Pro Asn Phe Lys Ser Asn Phe Asp Leu Ala Glu Asp Ala Lys Leu Gln
    530                 535                 540

Leu Ser Lys Asp Thr Tyr Asp Asp Asp Leu Asp Asn Leu Leu Ala Gln
545                 550                 555                 560

Ile Gly Asp Gln Tyr Ala Asp Leu Phe Leu Ala Ala Lys Asn Leu Ser
                565                 570                 575

Asp Ala Ile Leu Leu Ser Asp Ile Leu Arg Val Asn Thr Glu Ile Thr
            580                 585                 590

Lys Ala Pro Leu Ser Ala Ser Met Ile Lys Arg Tyr Asp Glu His His
            595                 600                 605

Gln Asp Leu Thr Leu Leu Lys Ala Leu Val Arg Gln Gln Leu Pro Glu
    610                 615                 620

Lys Tyr Lys Glu Ile Phe Phe Asp Gln Ser Lys Asn Gly Tyr Ala Gly
625                 630                 635                 640

Tyr Ile Asp Gly Gly Ala Ser Gln Glu Glu Phe Tyr Lys Phe Ile Lys
                645                 650                 655

Pro Ile Leu Glu Lys Met Asp Gly Thr Glu Glu Leu Leu Val Lys Leu
            660                 665                 670

Asn Arg Glu Asp Leu Leu Arg Lys Gln Arg Thr Phe Asp Asn Gly Ser
            675                 680                 685

Ile Pro His Gln Ile His Leu Gly Glu Leu His Ala Ile Leu Arg Arg
    690                 695                 700

Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
                725                 730                 735

Gly Asn Ser Arg Phe Ala Trp Met Thr Arg Lys Ser Glu Glu Thr Ile
            740                 745                 750

Thr Pro Trp Asn Phe Glu Glu Val Val Asp Lys Gly Ala Ser Ala Gln
            755                 760                 765

Ser Phe Ile Glu Arg Met Thr Asn Phe Asp Lys Asn Leu Pro Asn Glu
    770                 775                 780

Lys Val Leu Pro Lys His Ser Leu Leu Tyr Glu Tyr Phe Thr Val Tyr
785                 790                 795                 800

Asn Glu Leu Thr Lys Val Lys Tyr Val Thr Glu Gly Met Arg Lys Pro
                805                 810                 815

Ala Phe Leu Ser Gly Glu Gln Lys Lys Ala Ile Val Asp Leu Leu Phe
            820                 825                 830

Lys Thr Asn Arg Lys Val Thr Val Lys Gln Leu Lys Glu Asp Tyr Phe
            835                 840                 845

Lys Lys Ile Glu Cys Phe Asp Ser Val Glu Ile Ser Gly Val Glu Asp
    850                 855                 860
```

```
Arg Phe Asn Ala Ser Leu Gly Thr Tyr His Asp Leu Leu Lys Ile Ile
865                 870                 875                 880

Lys Asp Lys Asp Phe Leu Asp Asn Glu Glu Asn Glu Asp Ile Leu Glu
            885                 890                 895

Asp Ile Val Leu Thr Leu Thr Leu Phe Glu Asp Arg Glu Met Ile Glu
            900                 905                 910

Glu Arg Leu Lys Thr Tyr Ala His Leu Phe Asp Asp Lys Val Met Lys
            915                 920                 925

Gln Leu Lys Arg Arg Arg Tyr Thr Gly Trp Gly Arg Leu Ser Arg Lys
930                 935                 940

Leu Ile Asn Gly Ile Arg Asp Lys Gln Ser Gly Lys Thr Ile Leu Asp
945                 950                 955                 960

Phe Leu Lys Ser Asp Gly Phe Ala Asn Arg Asn Phe Met Gln Leu Ile
            965                 970                 975

His Asp Asp Ser Leu Thr Phe Lys Glu Asp Ile Gln Lys Ala Gln Val
            980                 985                 990

Ser Gly Gln Gly Asp Ser Leu His Glu His Ile Ala Asn Leu Ala Gly
            995                 1000                1005

Ser Pro Ala Ile Lys Lys Gly Ile Leu Gln Thr Val Lys Val Val
    1010                1015                1020

Asp Glu Leu Val Lys Val Met Gly Arg His Lys Pro Glu Asn Ile
    1025                1030                1035

Val Ile Glu Met Ala Arg Glu Asn Gln Thr Thr Gln Lys Gly Gln
    1040                1045                1050

Lys Asn Ser Arg Glu Arg Met Lys Arg Ile Glu Glu Gly Ile Lys
    1055                1060                1065

Glu Leu Gly Ser Gln Ile Leu Lys Glu His Pro Val Glu Asn Thr
    1070                1075                1080

Gln Leu Gln Asn Glu Lys Leu Tyr Leu Tyr Tyr Leu Gln Asn Gly
    1085                1090                1095

Arg Asp Met Tyr Val Asp Gln Glu Leu Asp Ile Asn Arg Leu Ser
    1100                1105                1110

Asp Tyr Asp Val Asp His Ile Val Pro Gln Ser Phe Leu Lys Asp
    1115                1120                1125

Asp Ser Ile Asp Asn Lys Val Leu Thr Arg Ser Asp Lys Asn Arg
    1130                1135                1140

Gly Lys Ser Asp Asn Val Pro Ser Glu Glu Val Val Lys Lys Met
    1145                1150                1155

Lys Asn Tyr Trp Arg Gln Leu Leu Asn Ala Lys Leu Ile Thr Gln
    1160                1165                1170

Arg Lys Phe Asp Asn Leu Thr Lys Ala Glu Arg Gly Gly Leu Ser
    1175                1180                1185

Glu Leu Asp Lys Ala Gly Phe Ile Lys Arg Gln Leu Val Glu Thr
    1190                1195                1200

Arg Gln Ile Thr Lys His Val Ala Gln Ile Leu Asp Ser Arg Met
    1205                1210                1215

Asn Thr Lys Tyr Asp Glu Asn Asp Lys Leu Ile Arg Glu Val Lys
    1220                1225                1230

Val Ile Thr Leu Lys Ser Lys Leu Val Ser Asp Phe Arg Lys Asp
    1235                1240                1245

Phe Gln Phe Tyr Lys Val Arg Glu Ile Asn Asn Tyr His His Ala
    1250                1255                1260
```

His Asp Ala Tyr Leu Asn Ala Val Val Gly Thr Ala Leu Ile Lys
1265                    1270                1275

Lys Tyr Pro Lys Leu Glu Ser Glu Phe Val Tyr Gly Asp Tyr Lys
1280                    1285                1290

Val Tyr Asp Val Arg Lys Met Ile Ala Lys Ser Glu Gln Glu Ile
1295                    1300                1305

Gly Lys Ala Thr Ala Lys Tyr Phe Phe Tyr Ser Asn Ile Met Asn
1310                    1315                1320

Phe Phe Lys Thr Glu Ile Thr Leu Ala Asn Gly Glu Ile Arg Lys
1325                    1330                1335

Arg Pro Leu Ile Glu Thr Asn Gly Glu Thr Gly Glu Ile Val Trp
1340                    1345                1350

Asp Lys Gly Arg Asp Phe Ala Thr Val Arg Lys Val Leu Ser Met
1355                    1360                1365

Pro Gln Val Asn Ile Val Lys Lys Thr Glu Val Gln Thr Gly Gly
1370                    1375                1380

Phe Ser Lys Glu Ser Ile Leu Pro Lys Arg Asn Ser Asp Lys Leu
1385                    1390                1395

Ile Ala Arg Lys Lys Asp Trp Asp Pro Lys Lys Tyr Gly Gly Phe
1400                    1405                1410

Asp Ser Pro Thr Val Ala Tyr Ser Val Leu Val Val Ala Lys Val
1415                    1420                1425

Glu Lys Gly Lys Ser Lys Lys Leu Lys Ser Val Lys Glu Leu Leu
1430                    1435                1440

Gly Ile Thr Ile Met Glu Arg Ser Ser Phe Glu Lys Asn Pro Ile
1445                    1450                1455

Asp Phe Leu Glu Ala Lys Gly Tyr Lys Glu Val Lys Lys Asp Leu
1460                    1465                1470

Ile Ile Lys Leu Pro Lys Tyr Ser Leu Phe Glu Leu Glu Asn Gly
1475                    1480                1485

Arg Lys Arg Met Leu Ala Ser Ala Gly Glu Leu Gln Lys Gly Asn
1490                    1495                1500

Glu Leu Ala Leu Pro Ser Lys Tyr Val Asn Phe Leu Tyr Leu Ala
1505                    1510                1515

Ser His Tyr Glu Lys Leu Lys Gly Ser Pro Glu Asp Asn Glu Gln
1520                    1525                1530

Lys Gln Leu Phe Val Glu Gln His Lys His Tyr Leu Asp Glu Ile
1535                    1540                1545

Ile Glu Gln Ile Ser Glu Phe Ser Lys Arg Val Ile Leu Ala Asp
1550                    1555                1560

Ala Asn Leu Asp Lys Val Leu Ser Ala Tyr Asn Lys His Arg Asp
1565                    1570                1575

Lys Pro Ile Arg Glu Gln Ala Glu Asn Ile Ile His Leu Phe Thr
1580                    1585                1590

Leu Thr Asn Leu Gly Ala Pro Ala Ala Phe Lys Tyr Phe Asp Thr
1595                    1600                1605

Thr Ile Asp Arg Lys Arg Tyr Thr Ser Thr Lys Glu Val Leu Asp
1610                    1615                1620

Ala Thr Leu Ile His Gln Ser Ile Thr Gly Leu Tyr Glu Thr Arg
1625                    1630                1635

Ile Asp Leu Ser Gln Leu Gly Gly Asp His His His His His His
1640                    1645                1650

<210> SEQ ID NO 11
<211> LENGTH: 1653
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Ser Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Leu Ala Leu
            260                 265                 270

Pro Lys Lys Lys Arg Lys Val Met Asp Lys Lys Tyr Ser Ile Gly Leu
        275                 280                 285

Asp Ile Gly Thr Asn Ser Val Gly Trp Ala Val Ile Thr Asp Glu Tyr
    290                 295                 300

Lys Val Pro Ser Lys Lys Phe Lys Val Leu Gly Asn Thr Asp Arg His
305                 310                 315                 320

Ser Ile Lys Lys Asn Leu Ile Gly Ala Leu Leu Phe Asp Ser Gly Glu
                325                 330                 335

Thr Ala Glu Ala Thr Arg Leu Lys Arg Thr Ala Arg Arg Tyr Thr
            340                 345                 350

Arg Arg Lys Asn Arg Ile Cys Tyr Leu Gln Glu Ile Phe Ser Asn Glu
        355                 360                 365
```

Met Ala Lys Val Asp Asp Ser Phe His Arg Leu Glu Glu Ser Phe
370             375                 380

Leu Val Glu Glu Asp Lys Lys His Glu Arg His Pro Ile Phe Gly Asn
385                 390                 395                 400

Ile Val Asp Glu Val Ala Tyr His Glu Lys Tyr Pro Thr Ile Tyr His
                405                 410                 415

Leu Arg Lys Lys Leu Val Asp Ser Thr Asp Lys Ala Asp Leu Arg Leu
            420                 425                 430

Ile Tyr Leu Ala Leu Ala His Met Ile Lys Phe Arg Gly His Phe Leu
        435                 440                 445

Ile Glu Gly Asp Leu Asn Pro Asp Asn Ser Asp Val Asp Lys Leu Phe
450                 455                 460

Ile Gln Leu Val Gln Thr Tyr Asn Gln Leu Phe Glu Glu Asn Pro Ile
465                 470                 475                 480

Asn Ala Ser Gly Val Asp Ala Lys Ala Ile Leu Ser Ala Arg Leu Ser
                485                 490                 495

Lys Ser Arg Arg Leu Glu Asn Leu Ile Ala Gln Leu Pro Gly Glu Lys
            500                 505                 510

Lys Asn Gly Leu Phe Gly Asn Leu Ile Ala Leu Ser Leu Gly Leu Thr
        515                 520                 525

Pro Asn Phe Lys Ser Asn Phe Asp Leu Ala Glu Asp Ala Lys Leu Gln
530                 535                 540

Leu Ser Lys Asp Thr Tyr Asp Asp Asp Leu Asp Asn Leu Leu Ala Gln
545                 550                 555                 560

Ile Gly Asp Gln Tyr Ala Asp Leu Phe Leu Ala Ala Lys Asn Leu Ser
                565                 570                 575

Asp Ala Ile Leu Leu Ser Asp Ile Leu Arg Val Asn Thr Glu Ile Thr
            580                 585                 590

Lys Ala Pro Leu Ser Ala Ser Met Ile Lys Arg Tyr Asp Glu His His
        595                 600                 605

Gln Asp Leu Thr Leu Leu Lys Ala Leu Val Arg Gln Gln Leu Pro Glu
610                 615                 620

Lys Tyr Lys Glu Ile Phe Phe Asp Gln Ser Lys Asn Gly Tyr Ala Gly
625                 630                 635                 640

Tyr Ile Asp Gly Gly Ala Ser Gln Glu Glu Phe Tyr Lys Phe Ile Lys
                645                 650                 655

Pro Ile Leu Glu Lys Met Asp Gly Thr Glu Glu Leu Leu Val Lys Leu
            660                 665                 670

Asn Arg Glu Asp Leu Leu Arg Lys Gln Arg Thr Phe Asp Asn Gly Ser
        675                 680                 685

Ile Pro His Gln Ile His Leu Gly Glu Leu His Ala Ile Leu Arg Arg
690                 695                 700

Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
                725                 730                 735

Gly Asn Ser Arg Phe Ala Trp Met Thr Arg Lys Ser Glu Glu Thr Ile
            740                 745                 750

Thr Pro Trp Asn Phe Glu Glu Val Val Asp Lys Gly Ala Ser Ala Gln
        755                 760                 765

Ser Phe Ile Glu Arg Met Thr Asn Phe Asp Lys Asn Leu Pro Asn Glu
770                 775                 780

Lys Val Leu Pro Lys His Ser Leu Leu Tyr Glu Tyr Phe Thr Val Tyr

```
                785                 790                 795                 800
Asn Glu Leu Thr Lys Val Lys Tyr Val Thr Glu Gly Met Arg Lys Pro
                    805                 810                 815
Ala Phe Leu Ser Gly Glu Gln Lys Lys Ala Ile Val Asp Leu Leu Phe
                    820                 825                 830
Lys Thr Asn Arg Lys Val Thr Val Lys Gln Leu Lys Glu Asp Tyr Phe
                    835                 840                 845
Lys Lys Ile Glu Cys Phe Asp Ser Val Glu Ile Ser Gly Val Glu Asp
                    850                 855                 860
Arg Phe Asn Ala Ser Leu Gly Thr Tyr His Asp Leu Leu Lys Ile Ile
865                 870                 875                 880
Lys Asp Lys Asp Phe Leu Asp Asn Glu Glu Asn Glu Asp Ile Leu Glu
                    885                 890                 895
Asp Ile Val Leu Thr Leu Thr Leu Phe Glu Asp Arg Glu Met Ile Glu
                    900                 905                 910
Glu Arg Leu Lys Thr Tyr Ala His Leu Phe Asp Asp Lys Val Met Lys
                    915                 920                 925
Gln Leu Lys Arg Arg Arg Tyr Thr Gly Trp Gly Arg Leu Ser Arg Lys
                    930                 935                 940
Leu Ile Asn Gly Ile Arg Asp Lys Gln Ser Gly Lys Thr Ile Leu Asp
945                 950                 955                 960
Phe Leu Lys Ser Asp Gly Phe Ala Asn Arg Asn Phe Met Gln Leu Ile
                    965                 970                 975
His Asp Asp Ser Leu Thr Phe Lys Glu Asp Ile Gln Lys Ala Gln Val
                    980                 985                 990
Ser Gly Gln Gly Asp Ser Leu His Glu His Ile Ala Asn Leu Ala Gly
                    995                 1000                1005
Ser Pro Ala Ile Lys Lys Gly Ile Leu Gln Thr Val Lys Val Val
                    1010                1015                1020
Asp Glu Leu Val Lys Val Met Gly Arg His Lys Pro Glu Asn Ile
                    1025                1030                1035
Val Ile Glu Met Ala Arg Glu Asn Gln Thr Thr Gln Lys Gly Gln
                    1040                1045                1050
Lys Asn Ser Arg Glu Arg Met Lys Arg Ile Glu Glu Gly Ile Lys
                    1055                1060                1065
Glu Leu Gly Ser Gln Ile Leu Lys Glu His Pro Val Glu Asn Thr
                    1070                1075                1080
Gln Leu Gln Asn Glu Lys Leu Tyr Leu Tyr Tyr Leu Gln Asn Gly
                    1085                1090                1095
Arg Asp Met Tyr Val Asp Gln Glu Leu Asp Ile Asn Arg Leu Ser
                    1100                1105                1110
Asp Tyr Asp Val Asp His Ile Val Pro Gln Ser Phe Leu Lys Asp
                    1115                1120                1125
Asp Ser Ile Asp Asn Lys Val Leu Thr Arg Ser Asp Lys Asn Arg
                    1130                1135                1140
Gly Lys Ser Asp Asn Val Pro Ser Glu Glu Val Val Lys Lys Met
                    1145                1150                1155
Lys Asn Tyr Trp Arg Gln Leu Leu Asn Ala Lys Leu Ile Thr Gln
                    1160                1165                1170
Arg Lys Phe Asp Asn Leu Thr Lys Ala Glu Arg Gly Gly Leu Ser
                    1175                1180                1185
Glu Leu Asp Lys Ala Gly Phe Ile Lys Arg Gln Leu Val Glu Thr
                    1190                1195                1200
```

```
Arg Gln Ile Thr Lys His Val Ala Gln Ile Leu Asp Ser Arg Met
1205                1210                1215

Asn Thr Lys Tyr Asp Glu Asn Asp Lys Leu Ile Arg Glu Val Lys
1220                1225                1230

Val Ile Thr Leu Lys Ser Lys Leu Val Ser Asp Phe Arg Lys Asp
1235                1240                1245

Phe Gln Phe Tyr Lys Val Arg Glu Ile Asn Asn Tyr His His Ala
1250                1255                1260

His Asp Ala Tyr Leu Asn Ala Val Val Gly Thr Ala Leu Ile Lys
1265                1270                1275

Lys Tyr Pro Lys Leu Glu Ser Glu Phe Val Tyr Gly Asp Tyr Lys
1280                1285                1290

Val Tyr Asp Val Arg Lys Met Ile Ala Lys Ser Glu Gln Glu Ile
1295                1300                1305

Gly Lys Ala Thr Ala Lys Tyr Phe Phe Tyr Ser Asn Ile Met Asn
1310                1315                1320

Phe Phe Lys Thr Glu Ile Thr Leu Ala Asn Gly Glu Ile Arg Lys
1325                1330                1335

Arg Pro Leu Ile Glu Thr Asn Gly Glu Thr Gly Glu Ile Val Trp
1340                1345                1350

Asp Lys Gly Arg Asp Phe Ala Thr Val Arg Lys Val Leu Ser Met
1355                1360                1365

Pro Gln Val Asn Ile Val Lys Lys Thr Glu Val Gln Thr Gly Gly
1370                1375                1380

Phe Ser Lys Glu Ser Ile Leu Pro Lys Arg Asn Ser Asp Lys Leu
1385                1390                1395

Ile Ala Arg Lys Lys Asp Trp Asp Pro Lys Lys Tyr Gly Gly Phe
1400                1405                1410

Asp Ser Pro Thr Val Ala Tyr Ser Val Leu Val Val Ala Lys Val
1415                1420                1425

Glu Lys Gly Lys Ser Lys Lys Leu Lys Ser Val Lys Glu Leu Leu
1430                1435                1440

Gly Ile Thr Ile Met Glu Arg Ser Ser Phe Glu Lys Asn Pro Ile
1445                1450                1455

Asp Phe Leu Glu Ala Lys Gly Tyr Lys Glu Val Lys Lys Asp Leu
1460                1465                1470

Ile Ile Lys Leu Pro Lys Tyr Ser Leu Phe Glu Leu Glu Asn Gly
1475                1480                1485

Arg Lys Arg Met Leu Ala Ser Ala Gly Glu Leu Gln Lys Gly Asn
1490                1495                1500

Glu Leu Ala Leu Pro Ser Lys Tyr Val Asn Phe Leu Tyr Leu Ala
1505                1510                1515

Ser His Tyr Glu Lys Leu Lys Gly Ser Pro Glu Asp Asn Glu Gln
1520                1525                1530

Lys Gln Leu Phe Val Glu Gln His Lys His Tyr Leu Asp Glu Ile
1535                1540                1545

Ile Glu Gln Ile Ser Glu Phe Ser Lys Arg Val Ile Leu Ala Asp
1550                1555                1560

Ala Asn Leu Asp Lys Val Leu Ser Ala Tyr Asn Lys His Arg Asp
1565                1570                1575

Lys Pro Ile Arg Glu Gln Ala Glu Asn Ile Ile His Leu Phe Thr
1580                1585                1590
```

```
Leu Thr Asn Leu Gly Ala Pro Ala Ala Phe Lys Tyr Phe Asp Thr
    1595            1600                1605

Thr Ile Asp Arg Lys Arg Tyr Thr Ser Thr Lys Glu Val Leu Asp
    1610            1615                1620

Ala Thr Leu Ile His Gln Ser Ile Thr Gly Leu Tyr Glu Thr Arg
    1625            1630                1635

Ile Asp Leu Ser Gln Leu Gly Gly Asp His His His His His His
    1640            1645                1650

<210> SEQ ID NO 12
<211> LENGTH: 1467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145             150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225             230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720
```

-continued

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val

```
                1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275
Arg Val Ile Leu Ala Asp Ala Asn Leu Asp Lys Val Leu Ser Ala
        1280                1285                1290
Tyr Asn Lys His Arg Asp Lys Pro Ile Arg Glu Gln Ala Glu Asn
        1295                1300                1305
Ile Ile His Leu Phe Thr Leu Thr Asn Leu Gly Ala Pro Ala Ala
        1310                1315                1320
Phe Lys Tyr Phe Asp Thr Thr Ile Asp Arg Lys Arg Tyr Thr Ser
        1325                1330                1335
Thr Lys Glu Val Leu Asp Ala Thr Leu Ile His Gln Ser Ile Thr
        1340                1345                1350
Gly Leu Tyr Glu Thr Arg Ile Asp Leu Ser Gln Leu Gly Gly Asp
        1355                1360                1365
Gly Ser Pro Lys Lys Lys Arg Lys Val Ser Ser Asp Tyr Lys Asp
        1370                1375                1380
His Asp Gly Asp Tyr Lys Asp His Asp Ile Asp Tyr Lys Asp Asp
        1385                1390                1395
Asp Asp Lys Ala Ala Gly Gly Gly Gly Ser Gly Arg Ala Asp Ala
        1400                1405                1410
Leu Asp Asp Phe Asp Leu Asp Met Leu Gly Ser Asp Ala Leu Asp
        1415                1420                1425
Asp Phe Asp Leu Asp Met Leu Gly Ser Asp Ala Leu Asp Asp Phe
        1430                1435                1440
Asp Leu Asp Met Leu Gly Ser Asp Ala Leu Asp Asp Phe Asp Leu
        1445                1450                1455
Asp Met Leu His His His His His His
        1460                1465

<210> SEQ ID NO 13
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
```

```
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
            485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
            565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
            645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
            725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
            805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
            835                 840                 845
```

```
Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245
```

```
Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

His His His His His His
    1370
```

<210> SEQ ID NO 14
<211> LENGTH: 1860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgggtgcta gcaaaggtga agagctgttt gacggtgtag taccgatctt agtggaatta      60
gacggcgacg tgaacggtca cgaatttagc gtgcgcggcg agggcgaagg tgacgctacc     120
gagggtgaat tgaccctgaa gtttatttgc acaacaggcg aattaccegt tccgtggccc     180 accttagtga ccaccctgac ctatggcgtt cagtgcttca gtgattaccc agatcatatg     240
gatcaacacg atttttttcaa atcagccatg cctgaaggat atgttcaaga gcgtacaatc     300
agcttcaagg acgatggcac ctataaaacg cgtgcggaag tgaaatttga aggcgacaca     360
ttagtaaacc gtatcgaact gaaaggtatc gacttcaaag aagacggcaa catttttaggc     420 cataagctgg aatataactt taattctcat gacgtgtata ttacggccga taaacaggaa     480
aacggtatca aggcagaatt tgaaattcgc ataacgtgg aggacggcag cgttcaatta     540
gcggatcatt atcaacaaaa cacgccgatt ggtgatgggc ctgtactgtt acctgacgat     600
cactacctga gcacggagtc agccctgagc aaagatccga cgaagaccg cgatcacatg     660 gttctgttag aattcgtgac cgctgcaggc attgatcatg aatggacga gctgtacaag     720 accggtggta gcggtggttc tggtggtagcg gcggtagcgg tggtagcggt     780
ggtagcggtg gcagcggcgg taccgcgagc aatttactga ccgtacacca aaatttgcct     840
gcattgccgg tcgatgcaac gagtgatgag gttcgcaaga acctgatgga catgttcagg     900
gatcgccagg cgttttctga gcataccctgg aaaatgcttc tgtccgtttg ccggtcgtgg     960
gcggcatggt gcaagttgaa taccggaaa tggtttccccg cagaacctga agatgttcgc    1020
gattatcttc tatatcttca ggcgcgcggt ctggcagtaa aaactatcca gcaacatttg    1080
ggccagctaa acatgcttca tcgtcggtcc gggctgccac gaccaagtga cagcaatgct    1140
gtttcactgg ttatgcggcg tatccgaaaa gaaaacgttg atgccggtga acgtgcaaaa    1200
caggctctag cgttcgaacg cactgatttc gaccaggttc gttcactcat ggaaaatagc    1260
```

| gatcgctgcc aggatatacg taatctggca tttctgggga ttgcttataa caccctgtta | 1320 |
| cgtatagccg aaattgccag gatcagggtt aaagatatct cacgtactga cggtgggaga | 1380 |
| atgttaatcc atattggcag aacgaaaacg ctggttagca ccgcaggtgt agagaaggca | 1440 |
| cttagcctgg gggtaactaa actggtcgag cgatggattt ccgtctctgg tgtagctgat | 1500 |
| gatccgaata actacctgtt ttgccgggtc agaaaaaatg tgttgccgc gccatctgcc | 1560 |
| accagccagc tatcaactcg cgccctgaaa gggattttg aagcaactca tcgattgatt | 1620 |
| tacggcgcta aggatgactc tggtcagaga tacctggcct ggtctggaca cagtgcccgt | 1680 |
| gtcggagccg cgcgagatat ggcccgcgct ggagtttcaa taccggagat catgcaagct | 1740 |
| ggtggctgga ccaatgtaaa tattgtcatg aactatatcc gtaacctgga tagtgaaaca | 1800 |
| ggggcaatgg tgcgcctgct ggaagatggc gacggcggat cccatcacca ccaccatcac | 1860 |

<210> SEQ ID NO 15
<211> LENGTH: 1059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| atggcgagca atttactgac cgtacaccaa aatttgcctg cattgccggt cgatgcaacg | 60 |
| agtgatgagg ttcgcaagaa cctgatggac atgttcaggg atcgccaggc gttttctgag | 120 |
| catacctgga aaatgcttct gtccgtttgc cggtcgtggg cggcatggtg caagttgaat | 180 |
| aaccggaaat ggtttcccgc agaacctgaa gatgttcgcg attatcttct atatcttcag | 240 |
| gcgcgcggtc tggcagtaaa aactatccag caacatttgg gccagctaaa catgcttcat | 300 |
| cgtcggtccg ggctgccacg accaagtgac agcaatgctg tttcactggt tatgcggcgt | 360 |
| atccgaaaag aaaacgttga tgccggtgaa cgtgcaaaac aggctctagc gttcgaacgc | 420 |
| actgatttcg accaggttcg ttcactcatg gaaaatagcg atcgctgcca ggatatacgt | 480 |
| aatctggcat ttctggggat tgcttataac accctgttac gtatagccga aattgccagg | 540 |
| atcagggtta aagatatctc acgtactgac ggtgggagaa tgttaatcca tattggcaga | 600 |
| acgaaaacgc tggttagcac cgcaggtgta gagaaggcac ttagcctggg ggtaactaaa | 660 |
| ctggtcgagc gatggatttc cgtctctggt gtagctgatg atccgaataa ctacctgttt | 720 |
| tgccgggtca gaaaaaatgg tgttgccgcg ccatctgcca ccagccagct atcaactcgc | 780 |
| gccctggaag ggattttga gcaactcat cgattgattt acggcgctaa ggatgactct | 840 |
| ggtcagagat acctggcctg gtctggacac agtgcccgtg tcggagccgc gcgagatatg | 900 |
| gcccgcgctg gagtttcaat accggagatc atgcaagctg gtggctggac caatgtaaat | 960 |
| attgtcatga actatatccg taacctggat agtgaaacag gggcaatggt gcgcctgctg | 1020 |
| gaagatggcg acggcggatc ccatcaccac caccatcac | 1059 |

<210> SEQ ID NO 16
<211> LENGTH: 4959
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgggtgcta gcaaaggtga agagctgttt gacggtgtag taccgatctt agtggaatta      60
gacggcgacg tgaacggtca cgaatttagc gtgcgcggcg agggcgaagg tgacgctacc     120
gagggtgaat tgaccctgaa gtttatttgc acaacaggcg aattaccgt tccgtggccc     180
accttagtga ccaccctgac ctatggcgtt cagtgcttca gtgattaccc agatcatatg     240
gatcaacacg attttttcaa atcagccatg cctgaaggat atgttcaaga gcgtacaatc     300
agcttcaagg acgatggcac ctataaaacg cgtgcggaag tgaaatttga aggcgacaca     360
ttagtaaacc gtatcgaact gaaaggtatc gacttcaaag aagacggcaa cattttaggc     420
cataagctgg aatataactt taattctcat gacgtgtata ttacggccga taaacaggaa     480
aacggtatca aggcagaatt tgaaattcgc cataacgtgg aggacggcag cgttcaatta     540
gcggatcatt atcaacaaaa cacgccgatt ggtgatgggc ctgtactgtt acctgacgat     600
cactacctga gcacggagtc agccctgagc aaagatccga acgaagaccg cgatcacatg     660
gttctgttag aattcgtgac cgctgcaggc attgatcatg gaatggacga gctgtacaag     720
accggtggta gcggtggttc tggtggttct ggtggtagcg gcggtagcgg tggtagcggt     780
ggtagcggtg gcagcggcgg taccgcgctc gcgctgccca agaagaagag gaaggtgatg     840
gataagaaat actcaatagg cttagatatc ggcacaaata gcgtcggatg gcggtgatc     900
actgatgaat ataaggttcc gtctaaaaag ttcaaggttc tgggaaatac agaccgccac     960
agtatcaaaa aaatcttat aggggctctt ttatttgaca gtggagagac agcggaagcg    1020
actcgtctca acggacagc tcgtagaagg tatacacgtc ggaagaatcg tatttgttat    1080
ctacaggaga ttttttcaaa tgagatggcg aaagtagatg atagtttctt tcatcgactt    1140
gaagagtctt ttttggtgga agaagacaag aagcatgaac gtcatcctat ttttggaaat    1200
atagtagatg aagttgctta tcatgagaaa tatccaacta tctatcatct gcgaaaaaaa    1260
ttggtagatt ctactgataa agcggatttg cgcttaatct atttggcctt agcgcatatg    1320
attaagtttc gtggtcattt tttgattgag ggagatttaa atcctgataa tagtgatgtg    1380
gacaaactat ttatccagtt ggtacaaacc tacaatcaat tatttgaaga aaaccctatt    1440
aacgcaagtg gagtagatgc taaagcgatt ctttctgcac gattgagtaa atcaagacga    1500
ttagaaaatc tcattgctca gctccccggt gagaagaaaa atggcttatt tgggaatctc    1560
attgctttgt cattgggttt gacccctaat tttaaatcaa attttgattt ggcagaagat    1620
gctaaattac agctttcaaa agatacttac gatgatgatt tagataattt attggcgcaa    1680
attggagatc aatatgctga tttgttttg gcagctaaga ttttatcaga tgctatttta    1740
ctttcagata tcctaagagt aaatactgaa ataactaagg ctcccctatc agcttcaatg    1800
attaaacgct acgatgaaca tcatcaagac ttgactcttt taaaagcttt agttcgacaa    1860
caacttccag aaaagtataa agaaatcttt tttgatcaat caaaaacgg atatgcaggt    1920
tatattgatg ggggagctag ccaagaagaa ttttataaat ttatcaaacc aattttagaa    1980
aaaatggatg gtactgagga attattggtg aaactaaatc gtgaagattt gctgcgcaag    2040
caacggacct tgacaacgg ctctattccc catcaaattc acttgggtga gctgcatgct    2100
attttgagaa gacaagaaga cttttatcca tttttaaaag acaatcgtga aagattgaa    2160
aaaatcttga cttttcgaat tccttattat gttggtccat tggcgcgtgg caatagtcgt    2220
tttgcatgga tgactcggaa gtctgaagaa acaattaccc catggaattt tgaagaagtt    2280
gtcgataaag gtgcttcagc tcaatcattt attgaacgca tgacaaactt tgataaaaat    2340
cttccaaatg aaaagtact accaaaacat agtttgcttt atgagtattt tacggtttat    2400
```

```
aacgaattga caaaggtcaa atatgttact gaaggaatgc gaaaaccagc atttctttca    2460
ggtgaacaga agaaagccat tgttgattta ctcttcaaaa caaatcgaaa agtaaccgtt    2520
aagcaattaa aagaagatta tttcaaaaaa atagaatgtt ttgatagtgt tgaaatttca    2580
ggagttgaag atagatttaa tgcttcatta ggtacctacc atgatttgct aaaaattatt    2640
aaagataaag attttttgga taatgaagaa aatgaagata tcttagagga tattgtttta    2700
acattgacct tatttgaaga tagggagatg attgaggaaa gacttaaaac atatgctcac    2760
ctctttgatg ataaggtgat gaaacagctt aaacgtcgcc gttatactgg ttggggacgt    2820
ttgtctcgaa aattgattaa tggtattagg gataagcaat ctggcaaaac aatattagat    2880
tttttgaaat cagatggttt tgccaatcgc aattttatgc agctgatcca tgatgatagt    2940
ttgacattta aagaagacat tcaaaaagca caagtgtctg acaaggcga tagtttacat     3000 gaacatattg caaatttagc tggtagccct gctattaaaa aaggtatttt acagactgta    3060
aaagttgttg atgaattggt caagtaatg gggcggcata agccagaaaa tatcgttatt     3120
gaaatggcac gtgaaaatca gacaactcaa aagggccaga aaaattcgcg agagcgtatg    3180
aaacgaatcg aagaaggtat caagaattta ggaagtcaga ttcttaaaga gcatcctgtt    3240
gaaaatactc aattgcaaaa tgaaaagctc tatctctatt atctccaaaa tggaagagac    3300
atgtatgtgg accaagaatt agatattaat cgtttaagtg attatgatgt cgatcacatt    3360
gttccacaaa gtttccttaa agacgattca atagacaata aggtcttaac gcgttctgat    3420
aaaaatcgtg gtaaatcgga taacgttcca agtgaagaag tagtcaaaaa gatgaaaaac    3480
tattggagac aacttctaaa cgccaagtta atcactcaac gtaagtttga taatttaacg    3540
aaagctgaac gtggaggttt gagtgaactt gataaagctg gttttatcaa acgccaattg    3600
gttgaaactc gccaaatcac taagcatgtg gcacaaattt tggatagtcg catgaatact    3660
aaatacgatg aaaatgataa acttattcga gaggttaaag tgattacctt aaaatctaaa    3720
ttagtttctg acttccgaaa agatttccaa ttctataaag tacgtgagat taacaattac    3780
catcatgccc atgatgcgta tctaaatgcc gtcgttggaa ctgctttgat taagaaatat    3840
ccaaaacttg aatcggagtt tgtctatggt gattataaag tttatgatgt tcgtaaaatg    3900
attgctaagt ctgagcaaga ataggcaaa gcaaccgcaa atatttctt ttactctaat     3960 atcatgaact tcttcaaaac agaaattaca cttgcaaatg gagagattcg caaacgccct    4020
ctaatcgaaa ctaatgggga aactggagaa attgtctggg ataaagggcg agattttgcc    4080
acagtgcgca aagtattgtc catgcccca gtcaatattg tcaagaaaac agaagtacag     4140
acaggcggat tctccaagga gtcaattta ccaaaaagaa attcggacaa gcttattgct     4200
cgtaaaaaag actgggatcc aaaaaaatat ggtggttttg atagtccaac ggtagcttat    4260
tcagtcctag tggttgctaa ggtggaaaaa gggaaatcga agaagttaaa atccgttaaa    4320
gagttactag ggatcacaat tatggaaaga agttcctttg aaaaaaatcc gattgacttt    4380
ttagaagcta aaggatataa ggaagttaaa aaagacttaa tcattaaact acctaaatat    4440 agtcttttg agttagaaaa cggtcgtaaa cggatgctgg ctagtgccgg agaattacaa     4500
aaaggaaatg agctggctct gccaagcaaa tatgtgaatt ttttatattt agctagtcat    4560
tatgaaaagt tgaagggtag tccagaagat aacgaacaaa aacaattgtt tgtggagcag    4620
cataagcatt atttagatga gattattgag caaatcagtg aattttctaa gcgtgttatt    4680
ttagcagatg ccaatttaga taaagttctt agtgcatata acaaacatag agacaaacca    4740
```

| | | |
|---|---|---|
| atacgtgaac aagcagaaaa tattattcat ttatttacgt tgacgaatct tggagctccc | 4800 | |
| gctgcttta aatattttga tacaacaatt gatcgtaaac gatatacgtc tacaaaagaa | 4860 | |
| gttttagatg ccactcttat ccatcaatcc atcactggtc tttatgaaac acgcattgat | 4920 | |
| ttgagtcagc taggaggtga ccatcaccac caccatcac | 4959 | |

<210> SEQ ID NO 17
<211> LENGTH: 4959
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

| | | |
|---|---|---|
| atgggtgcta gcaaaggtga acgtctgttt cgtggtaaag taccgatctt agtggaatta | 60 | |
| aagggcgacg tgaacggtca taaatttagc gtgcgcggca aaggcaaagg tgacgctacc | 120 | |
| cgtggtaaat tgaccctgaa gtttatttgc acaacaggca aattaccccgt tccgtggccc | 180 | |
| accttagtga ccaccctgac ctatggcgtt cagtgcttca gtcgttaccc taaacatatg | 240 | |
| aaacgtcacg attttttcaa atcagccatg cctaaaggat atgttcaaga gcgtacaatc | 300 | |
| agcttcaaga aggatggcaa atataaaacg cgtgcggaag tgaaatttga aggccgcaca | 360 | |
| ttagtaaatc gtatcaaact gaaaggtcgt gacttcaaag aaaaaggcaa cattttaggc | 420 | |
| cataaactgc gttataactt taattctcat aaggtgtata ttacggccga taaacgcaag | 480 | |
| aatggtatca aggcaaaatt caaaattcgc cataacgtga agacggcag cgttcaatta | 540 | |
| gcggatcatt atcaacaaaa cacgccgatt ggtcgcgggc ctgtactgtt acctcgcaac | 600 | |
| cactacctga gcacccgttc taaactgagc aaagatccga agaaaaacg cgatcacatg | 660 | |
| gttctgttag aattcgtgac cgctgcaggc attaagcacg gacgcgacga acgctacaag | 720 | |
| accggtggta gcggtggttc tggtggttct ggtggtagcg gcggtagcgg tggtagcggt | 780 | |
| ggtagcggtg gcagcggcgg taccgcgctc gcgctgccca agaagaagag gaaggtgatg | 840 | |
| gataagaaat actcaatagg cttagatatc ggcacaaata gcgtcggatg ggcggtgatc | 900 | |
| actgatgaat ataaggttcc gtctaaaaag ttcaaggttc tgggaaatac agaccgccac | 960 | |
| agtatcaaaa aaaatcttat aggggctctt ttatttgaca gtggagagac agcggaagcg | 1020 | |
| actcgtctca aacggacagc tcgtagaagg tatacacgtc ggaagaatcg tatttgttat | 1080 | |
| ctacaggaga ttttttcaaa tgagatggcg aaagtagatg atagtttctt tcatcgactt | 1140 | |
| gaagagtctt ttttggtgga agaagacaag aagcatgaac gtcatcctat ttttggaaat | 1200 | |
| atagtagatg aagttgctta tcatgagaaa tatccaacta tctatcatct gcgaaaaaaa | 1260 | |
| ttggtagatt ctactgataa agcggatttg cgcttaatct atttggcctt agcgcatatg | 1320 | |
| attaagtttc gtggtcattt tttgattgag ggagatttaa atcctgataa tagtgatgtg | 1380 | |
| gacaaactat ttatccagtt ggtacaaacc tacaatcaat atttgaaga aaaccctatt | 1440 | |
| aacgcaagtg gagtagatgc taaagcgatt ctttctgcac gattgagtaa atcaagacga | 1500 | |
| ttagaaaatc tcattgctca gctccccggt gagaagaaaa atggcttatt tgggaatctc | 1560 | |
| attgctttgt cattgggttt gacccctaat tttaaatcaa attttgattt ggcagaagat | 1620 | |
| gctaaattac agctttcaaa agatacttac gatgatgatt tagataattt attggcgcaa | 1680 | |
| attggagatc aatatgctga tttgtttttg gcagctaaga atttatcaga tgctattta | 1740 | |
| ctttcagata tcctaagagt aaatactgaa ataactaagg ctcccctatc agcttcaatg | 1800 | |

```
attaaacgct acgatgaaca tcatcaagac ttgactcttt taaaagcttt agttcgacaa      1860
caacttccag aaaagtataa agaaatcttt tttgatcaat caaaaaacgg atatgcaggt      1920
tatattgatg ggggagctag ccaagaagaa ttttataaat ttatcaaacc aattttagaa      1980
aaaatggatg gtactgagga attattggtg aaactaaatc gtgaagattt gctgcgcaag      2040
caacggacct ttgacaacgg ctctattccc catcaaattc acttgggtga gctgcatgct      2100
attttgagaa gacaagaaga cttttatcca ttttttaaaag acaatcgtga gaagattgaa      2160
aaaatcttga cttttcgaat tccttattat gttggtccat ggcgcgtgg caatagtcgt       2220 tttgcatgga tgactcggaa gtctgaagaa acaattaccc catgaatttt tgaagaagtt      2280
gtcgataaag gtgcttcagc tcaatcattt attgaacgca tgacaaactt tgataaaaat      2340
cttccaaatg aaaagtact accaaaacat agtttgcttt atgagtattt tacggtttat        2400
aacgaattga caaaggtcaa atatgttact gaaggaatgc gaaaaccagc atttctttca      2460
ggtgaacaga agaagccat tgttgattta ctcttcaaaa caaatcgaaa agtaaccgtt        2520
aagcaattaa agaagatta tttcaaaaaa atagaatgtt ttgatagtgt tgaaatttca       2580
ggagttgaag atagatttaa tgcttcatta ggtacctacc atgatttgct aaaaattatt      2640
aaagataaag attttttgga taatgaagaa atgaagata tcttagagga tattgttta       2700 acattgacct tatttgaaga tagggagatg attgaggaaa gacttaaaac atatgctcac     2760
ctctttgatg ataaggtgat gaaacagctt aaacgtcgcc gttatactgg ttggggacgt     2820
ttgtctcgaa aattgattaa tggtattagg gataagcaat ctggcaaaac aatattagat     2880
tttttgaaat cagatggttt tgccaatcgc aattttatgc agctgatcca tgatgatagt     2940
ttgacattta aagaagacat tcaaaaagca caagtgtctg acaaggcga tagtttacat       3000 gaacatattg caaatttagc tggtagccct gctattaaaa aaggtatttt acagactgta     3060
aaagttgttg atgaattggt caaagtaatg gggcggcata agccagaaaa tatcgttatt     3120
gaaatggcac gtgaaaatca gacaactcaa aagggccaga aaaattcgcg agagcgtatg     3180
aaacgaatcg aagaaggtat caagaattta ggaagtcaga ttcttaaaga gcatcctgtt     3240
gaaaatactc aattgcaaaa tgaaaagctc tatctctatt atctccaaaa tggaagagac     3300
atgtatgtgg accaagaatt agatattaat cgtttaagtg attatgatgt cgatcacatt     3360
gttccacaaa gttccttaa agacgattca atagacaata aggtcttaac gcgttctgat      3420
aaaaatcgtg gtaaatcgga taacgttcca agtgaagaag tagtcaaaaa gatgaaaaac     3480
tattggagac aacttctaaa cgccaagtta atcactcaac gtaagtttga taatttaacg     3540
aaagctgaac gtggaggttt gagtgaactt gataaagctg gttttatcaa acgccaattg     3600
gttgaaactc gccaaatcac taagcatgtg gcacaaattt tggatagtcg catgaatact     3660
aaatacgatg aaaatgataa acttattcga gaggttaaag tgattacctt aaaatctaaa     3720
ttagtttctg acttccgaaa agatttccaa ttctataaag tacgtgagat taacaattac     3780
catcatgccc atgatgcgta tctaaatgcc gtcgttggaa ctgctttgat taagaaatat     3840
ccaaaacttg aatcggagtt tgtctatggt gattataaag tttatgatgt tcgtaaaatg     3900
attgctaagt ctgagcaaga aataggcaaa gcaaccgcaa atatttctt ttactctaat      3960 atcatgaact tcttcaaaac agaaattaca cttgcaaatg gagagattcg caaacgccct     4020
ctaatcgaaa ctaatgggga aactggagaa attgtctggg ataaagggcg agattttgcc     4080
acagtgcgca agtattgtc catgcccaa gtcaatattg tcaagaaaac agaagtacag       4140
acaggcggat tctccaagga gtcaatttta ccaaaaagaa attcggacaa gcttattgct     4200
```

```
cgtaaaaaag actgggatcc aaaaaaatat ggtggttttg atagtccaac ggtagcttat    4260
tcagtcctag tggttgctaa ggtggaaaaa gggaaatcga agaagttaaa atccgttaaa    4320
gagttactag ggatcacaat tatggaaaga agttcctttg aaaaaaatcc gattgacttt    4380
ttagaagcta aaggatataa ggaagttaaa aaagacttaa tcattaaact acctaaatat    4440 agtcttttg agttagaaaa cggtcgtaaa cggatgctgg ctagtgccgg agaattacaa     4500
aaaggaaatg agctggctct gccaagcaaa tatgtgaatt ttttatattt agctagtcat    4560
tatgaaaagt tgaagggtag tccagaagat aacgaacaaa aacaattgtt tgtggagcag    4620
cataagcatt atttagatga gattattgag caaatcagtg aattttctaa gcgtgttatt    4680
ttagcagatg ccaatttaga taaagttctt agtgcatata acaaacatag agacaaacca    4740
atacgtgaac aagcagaaaa tattattcat ttatttacgt tgacgaatct ggagctccc     4800 gctgctttta aatattttga tacaacaatt gatcgtaaac gatatacgtc tacaaaagaa    4860
gttttagatg ccactcttat ccatcaatcc atcactggtc tttatgaaac acgcattgat    4920
ttgagtcagc taggaggtga ccatcaccac caccatcac                           4959

<210> SEQ ID NO 18
<211> LENGTH: 4152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggct cttttatttg acagtggaga gacagcggaa      180
gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt cttttttggt ggaagaagac aagaagcatg aacgtcatcc tattttttgga    360 aatatagtag atgaagttgc ttatcatgag aaatatccaa ctatctatca tctgcgaaaa     420
aaattggtag attctactga taaagcggat ttgcgcttaa tctatttggc cttagcgcat    480
atgattaagt ttcgtggtca ttttttgatt gagggagatt taaatcctga taatagtgat     540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaatggctt atttgggaat     720 ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta gaattttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga    1020
caacaacttc cagaaaagta taaagaaatc ttttttgatc aatcaaaaaa cggatatgca    1080
ggttatattg atgggggagc tagccaagaa gaatttttata aatttatcaa accaatttta    1140
gaaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
```

```
gctattttga gaagacaaga agactttat  ccatttttaa aagacaatcg tgagaagatt     1320
gaaaaaatct tgactttcg  aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc  agctcaatca tttattgaac gcatgacaaa ctttgataaa    1500
aatcttccaa atgaaaagt  actaccaaaa catagtttgc tttatgagta ttttacggtt    1560
tataacgaat tgacaaggt  caaatatgtt actgaaggaa tgcgaaaacc agcatttctt    1620
tcaggtgaac agaagaaagc cattgttgat ttactcttca aaacaaatcg aaaagtaacc    1680
gttaagcaat taaagaaga  ttatttcaaa aaatagaat  gttttgatag tgttgaaatt    1740
tcaggagttg aagatagatt taatgcttca ttaggtacct accatgattt gctaaaaatt    1800
attaaagata aagatttttt ggataatgaa gaaaatgaag atatcttaga ggatattgtt    1860
ttaacattga ccttatttga agataggag  atgattgagg aaagacttaa acatatgct     1920 cacctctttg atgataaggt gatgaaacag cttaaacgtc gccgttatac tggttgggga    1980
cgtttgtctc gaaaattgat taatggtatt agggataagc aatctggcaa acaatatta    2040 gattttttga aatcagatgg ttttgccaat cgcaatttta tgcagctgat ccatgatgat    2100
agtttgacat ttaagaaga  cattcaaaaa gcacaagtgt ctggacaagg cgatagttta    2160
catgaacata ttgcaaattt agctggtagc cctgctatta aaaaaggtat tttacagact    2220
gtaaaagttg ttgatgaatt ggtcaaagta atggggcggc ataagccaga aatatcgtt    2280 attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatat  aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac  cttaaaatct    2880 aaattagttt ctgacttccg aaaagatttc caattctata agtacgtga  gattaacaat    2940 taccatcatg cccatgatgc gtatctaaat gccgtcgttg gaactgcttt gattaagaaa    3000
tatccaaaac ttgaatcgga gtttgtctat ggtgattata agtttatga  tgttcgtaaa    3060 atgattgcta agtctgagca agaaatagc  aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aagggaaat  cgaagaagtt aaaatccgtt    3480
aaagagttac tagggatcac aattatgaa  agaagttcct ttgaaaaaaa tccgattgac    3540
tttttagaag ctaaaggata taaggaagtt aaaaaagact taatcattaa actacctaaa    3600
```

```
tatagtctttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa     4020 gaagttttag atgccactct tatccatcaa tccatcactg gtctttatga aacacgcatt    4080
gatttgagtc agctaggagg tgaccccaag aagaagagga aggtgatgga taagcatcac    4140
caccaccatc ac                                                         4152
```

<210> SEQ ID NO 19
<211> LENGTH: 4401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atggataaga aatactcaat aggcttagct atcggcacaa atagcgtcgg atgggcggtg      60
atcactgatg aatataaggt tccgtctaaa aagttcaagg ttctgggaaa tacagaccgc     120
cacagtatca aaaaaatct tataggggct cttttatttg acagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt ctttttttggt ggaagaagac aagaagcatg aacgtcatcc tattttttgga    360 aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt ttcgtggtca tttttttgatt gagggagatt taaatcctga taatagtgat     540
gtggacaaac tatttatcca gttggtacaa acctacaatc aattatttga agaaaaccct     600
attaacgcaa gtggagtaga tgctaaagcg attctttctg cacgattgag taaatcaaga     660
cgattagaaa atctcattgc tcagctcccc ggtgagaaga aaaatggctt atttgggaat     720
ctcattgctt tgtcattggg tttgaccccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga    1020
caacaacttc cagaaaagta taagaaatc ttttttgatc aatcaaaaaa cggatatgca    1080
ggttatattg atgggggagc tagccaagaa gaattttata atttatcaa accaatttta    1140 gaaaaaatgg atggtactga ggaattattg gtgaaactaa atcgtgaaga tttgctgcgc    1200
aagcaacgga ccttttgacaa cggctctatt ccccatcaaa ttcacttggg tgagctgcat    1260 gctatttttga aagacaaga agactttttat ccatttttaa aagacaatcg tgagaagatt    1320
gaaaaaatct tgacttttcg aattcccttat tatgttggtc cattggcgcg tggcaatagt    1380
cgttttgcat ggatgactcg gaagtctgaa gaaacaatta ccccatggaa ttttgaagaa    1440
```

```
gttgtcgata aaggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaaatgaag atatcttaga ggatattgtt    1860
ttaacattga ccttatttga agatagggag atgattgagg aaagacttaa acatatgct    1920 cacctctttg atgataaggt gatgaaacag cttaaacgtc gccgttatac tggttgggga    1980
cgtttgtctc gaaaattgat taatggtatt agggataagc aatctggcaa acaatatta    2040 gattttttga atcagatgg ttttgccaat cgcaatttta tgcagctgat ccatgatgat    2100
agtttgacat ttaagaaga cattcaaaaa gcacaagtgt ctggacaagg cgatagttta    2160
catgaacata ttgcaaattt agctggtagc cctgctatta aaaaggtat tttacagact    2220 gtaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatgcc    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac cttaaaatct    2880 aaattagttt ctgacttccg aaaagatttc caattctata agtacgtga gattaacaat    2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaagagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga atttttata tttagctagt    3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
```

-continued

```
attttagcag atgccaattt agataaagtt cttagtgcat ataacaaaca tagagacaaa      3900
ccaatacgtg aacaagcaga aaatattatt catttattta cgttgacgaa tcttggagct      3960
cccgctgctt ttaaatattt tgatacaaca attgatcgta aacgatatac gtctacaaaa      4020
gaagttttag atgccactct tatccatcaa tccatcactg gtctttatga aacacgcatt      4080
gatttgagtc agctaggagg tgacggttct cccaagaaga agaggaaagt ctcgagcgac      4140
tacaaagacc atgacggtga ttataaagat catgacatcg attacaagga tgacgatgac      4200
aaggctgcag gagcggtgg aagcgggcgc gccgacgcgc tggacgattt cgatctcgac      4260
atgctgggtt ctgatgccct cgatgacttt gacctggata tgttgggaag cgacgcattg      4320
gatgactttg atctggacat gctcggctcc gatgctctgg acgatttcga tctcgatatg      4380
ttacatcacc accaccatca c                                                4401
```

<210> SEQ ID NO 20
<211> LENGTH: 238
<212> TYPE: PRT
<213> ORGANISM: Aequorea victoria

<400> SEQUENCE: 20

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 21
<211> LENGTH: 96
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 21
tcaaggctgt gcagatgctc tgggtgaacc tcatcatgga cacgtttgcc tccctggccc    60
tggccacaga gccacctacg gagactctgc ttctga                              96

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
taatacgact cactataggg caaggctgtg cagatgctct gttttagagc tagaaatagc    60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taatacgact cactataggg ctctgggtga acctcatcag ttttagagct agaaatagca    60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
taatacgact cactataggg aggcaaacgt gtccatgatg gttttagagc tagaaatagc    60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
taatacgact cactataggg catggacacg tttgcctccc gttttagagc tagaaatagc    60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
taatacgact cactataggg catggacacg tttgccttcc gttttagagc tagaaatagc    60

<210> SEQ ID NO 27
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 27
taatacgact cactataggg cacgtttgcc tccctggccc gttttagagc tagaaatagc    60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taatacgact cactataggg cacgtttgcc ttcctggccc gttttagagc tagaaatagc    60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
taatacgact cactataggg ctctgtggcc agggccaggg gttttagagc tagaaatagc    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
taatacgact cactataggg ctctgtggcc agggccagga gttttagagc tagaaatagc    60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taatacgact cactataggg tggctctgtg gccagggcca gttttagagc tagaaatagc    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
taatacgact cactataggg cctggccaca gagccaccta gttttagagc tagaaatagc    60

<210> SEQ ID NO 33
<211> LENGTH: 60
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 33
taatacgact cactataggg ctacggagac tctgcttctg gttttagagc tagaaatagc      60

<210> SEQ ID NO 34
<211> LENGTH: 13
<212> TYPE: PRT
<213> ORGANISM: Litoria aurea

<400> SEQUENCE: 34

Gly Leu Phe Asp Ile Ile Lys Lys Ile Ala Glu Ser Phe
1               5                   10

<210> SEQ ID NO 35
<211> LENGTH: 16
<212> TYPE: PRT
<213> ORGANISM: Litoria citropa

<400> SEQUENCE: 35

Gly Leu Phe Asp Ile Ile Lys Lys Val Ala Ser Val Ile Gly Gly Leu
1               5                   10                  15

<210> SEQ ID NO 36
<211> LENGTH: 14
<212> TYPE: PRT
<213> ORGANISM: Rana catesbeiana

<400> SEQUENCE: 36

Phe Leu Phe Pro Leu Ile Thr Ser Phe Leu Ser Lys Val Leu
1               5                   10

<210> SEQ ID NO 37
<211> LENGTH: 13
<212> TYPE: PRT
<213> ORGANISM: Rana catesbeiana

<400> SEQUENCE: 37

Phe Ile Ser Ala Ile Ala Ser Met Leu Gly Lys Phe Leu
1               5                   10

<210> SEQ ID NO 38
<211> LENGTH: 13
<212> TYPE: PRT
<213> ORGANISM: Litoria ewingi

<400> SEQUENCE: 38

Gly Trp Phe Asp Val Val Lys His Ile Ala Ser Ala Val
1               5                   10

<210> SEQ ID NO 39
<211> LENGTH: 13
<212> TYPE: PRT
<213> ORGANISM: Hylarana picturata

<400> SEQUENCE: 39

Phe Phe Gly Ser Val Leu Lys Leu Ile Pro Lys Ile Leu
1               5                   10

<210> SEQ ID NO 40
<211> LENGTH: 13
<212> TYPE: PRT
<213> ORGANISM: Calliphora vicina
```

```
<400> SEQUENCE: 40

His Gly Val Ser Gly His Gly Gln His Gly Val His Gly
1               5                   10

<210> SEQ ID NO 41
<211> LENGTH: 13
<212> TYPE: PRT
<213> ORGANISM: Rana temporaria

<400> SEQUENCE: 41

Phe Leu Pro Leu Ile Gly Arg Val Leu Ser Gly Ile Leu
1               5                   10

<210> SEQ ID NO 42
<211> LENGTH: 13
<212> TYPE: PRT
<213> ORGANISM: Litoria sp.
<220> FEATURE:
<223> OTHER INFORMATION: Litoria aurea or Litoria raniformis

<400> SEQUENCE: 42

Gly Leu Phe Asp Ile Ile Lys Lys Ile Ala Glu Ser Ile
1               5                   10

<210> SEQ ID NO 43
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 43

Gly Leu Leu Asp Ile Val Lys Lys Val Val Gly Ala Phe Gly Ser Leu
1               5                   10                  15

<210> SEQ ID NO 44
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 44

Gly Leu Phe Asp Ile Val Lys Lys Val Val Gly Ala Leu Gly Ser Leu
1               5                   10                  15

<210> SEQ ID NO 45
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 45

Gly Leu Phe Asp Ile Val Lys Lys Val Val Gly Ala Ile Gly Ser Leu
1               5                   10                  15

<210> SEQ ID NO 46
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 46
```

Gly Leu Phe Asp Ile Val Lys Lys Val Val Gly Thr Leu Ala Gly Leu
1               5                   10                  15

<210> SEQ ID NO 47
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 47

Gly Leu Phe Asp Ile Val Lys Lys Val Val Gly Ala Phe Gly Ser Leu
1               5                   10                  15

<210> SEQ ID NO 48
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 48

Gly Leu Phe Asp Ile Ala Lys Lys Val Ile Gly Val Ile Gly Ser Leu
1               5                   10                  15

<210> SEQ ID NO 49
<211> LENGTH: 17
<212> TYPE: PRT
<213> ORGANISM: Litoria sp.
<220> FEATURE:
<223> OTHER INFORMATION: Litoria aurea or Litoria raniformis

<400> SEQUENCE: 49

Gly Leu Phe Asp Ile Val Lys Lys Ile Ala Gly His Ile Ala Gly Ser
1               5                   10                  15

Ile

<210> SEQ ID NO 50
<211> LENGTH: 17
<212> TYPE: PRT
<213> ORGANISM: Litoria sp.
<220> FEATURE:
<223> OTHER INFORMATION: Litoria aurea or Litoria raniformis

<400> SEQUENCE: 50

Gly Leu Phe Asp Ile Val Lys Lys Ile Ala Gly His Ile Ala Ser Ser
1               5                   10                  15

Ile

<210> SEQ ID NO 51
<211> LENGTH: 17
<212> TYPE: PRT
<213> ORGANISM: Litoria sp.
<220> FEATURE:
<223> OTHER INFORMATION: Litoria aurea or Litoria raniformis

<400> SEQUENCE: 51

Gly Leu Phe Asp Ile Val Lys Lys Ile Ala Gly His Ile Val Ser Ser
1               5                   10                  15

Ile

<210> SEQ ID NO 52
<211> LENGTH: 13
<212> TYPE: PRT
<213> ORGANISM: Rana temporaria

<400> SEQUENCE: 52

Phe Val Gln Trp Phe Ser Lys Phe Leu Gly Arg Ile Leu
1               5                   10

<210> SEQ ID NO 53
<211> LENGTH: 16
<212> TYPE: PRT
<213> ORGANISM: Litoria citropa

<400> SEQUENCE: 53

Gly Leu Phe Asp Val Ile Lys Lys Val Ala Ser Val Ile Gly Gly Leu
1               5                   10                  15

<210> SEQ ID NO 54
<211> LENGTH: 16
<212> TYPE: PRT
<213> ORGANISM: Litoria citropa

<400> SEQUENCE: 54

Gly Leu Phe Asp Ile Ile Lys Lys Val Ala Ser Val Val Gly Gly Leu
1               5                   10                  15

<210> SEQ ID NO 55
<211> LENGTH: 15
<212> TYPE: PRT
<213> ORGANISM: Rana dybowskii

<400> SEQUENCE: 55

Val Trp Pro Leu Gly Leu Val Ile Cys Lys Ala Leu Lys Ile Cys
1               5                   10                  15

<210> SEQ ID NO 56
<211> LENGTH: 14
<212> TYPE: PRT
<213> ORGANISM: Rana cascadae

<400> SEQUENCE: 56

Asn Phe Leu Gly Thr Leu Val Asn Leu Ala Lys Lys Ile Leu
1               5                   10

<210> SEQ ID NO 57
<211> LENGTH: 13
<212> TYPE: PRT
<213> ORGANISM: Rana ornativentris

<400> SEQUENCE: 57

Phe Leu Pro Leu Ile Gly Lys Ile Leu Gly Thr Ile Leu
1               5                   10

<210> SEQ ID NO 58
<211> LENGTH: 13
<212> TYPE: PRT
<213> ORGANISM: Rana boylii

<400> SEQUENCE: 58

Phe Leu Pro Ile Ile Ala Lys Val Leu Ser Gly Leu Leu
1               5                   10

<210> SEQ ID NO 59
<211> LENGTH: 13
<212> TYPE: PRT
<213> ORGANISM: Unknown
<220> FEATURE:
<223> OTHER INFORMATION: Description of Unknown: Antimicrobial peptide

```
<400> SEQUENCE: 59

Phe Leu Pro Ile Val Gly Lys Leu Leu Ser Gly Leu Leu
1               5                   10

<210> SEQ ID NO 60
<211> LENGTH: 13
<212> TYPE: PRT
<213> ORGANISM: Rana virgatipes

<400> SEQUENCE: 60

Phe Leu Ser Ser Ile Gly Lys Ile Leu Gly Asn Leu Leu
1               5                   10

<210> SEQ ID NO 61
<211> LENGTH: 13
<212> TYPE: PRT
<213> ORGANISM: Pelophylax saharica

<400> SEQUENCE: 61

Phe Leu Ser Gly Ile Val Gly Met Leu Gly Lys Leu Phe
1               5                   10

<210> SEQ ID NO 62
<211> LENGTH: 9
<212> TYPE: PRT
<213> ORGANISM: Apis mellifera

<400> SEQUENCE: 62

Thr Pro Phe Lys Leu Ser Leu His Leu
1               5

<210> SEQ ID NO 63
<211> LENGTH: 14
<212> TYPE: PRT
<213> ORGANISM: Hyla punctata

<400> SEQUENCE: 63

Gly Ile Leu Asp Ala Ile Lys Ala Ile Ala Lys Ala Ala Gly
1               5                   10

<210> SEQ ID NO 64
<211> LENGTH: 12
<212> TYPE: PRT
<213> ORGANISM: Litoria sp.
<220> FEATURE:
<223> OTHER INFORMATION: Litoria aurea or Litoria raniformis

<400> SEQUENCE: 64

Leu Phe Asp Ile Ile Lys Lys Ile Ala Glu Ser Phe
1               5                   10

<210> SEQ ID NO 65
<211> LENGTH: 25
<212> TYPE: PRT
<213> ORGANISM: Unknown
<220> FEATURE:
<223> OTHER INFORMATION: Description of Unknown: Antimicrobial peptide

<400> SEQUENCE: 65

Leu Phe Asp Ile Ile Lys Lys Ile Ala Glu Ser Gly Phe Leu Phe Asp
1               5                   10                  15

Ile Ile Lys Lys Ile Ala Glu Ser Phe
            20                  25
```

<210> SEQ ID NO 66
<211> LENGTH: 24
<212> TYPE: PRT
<213> ORGANISM: Cryptotympana dubia

<400> SEQUENCE: 66

Gly Leu Leu Asn Gly Leu Ala Leu Arg Leu Gly Lys Arg Ala Leu Lys
1               5                   10                  15

Lys Ile Ile Lys Arg Leu Cys Arg
            20

<210> SEQ ID NO 67
<211> LENGTH: 14
<212> TYPE: PRT
<213> ORGANISM: Unknown
<220> FEATURE:
<223> OTHER INFORMATION: Description of Unknown: Antimicrobial peptide

<400> SEQUENCE: 67

Gly His His His His His His His His His His His His His
1               5                   10

<210> SEQ ID NO 68
<211> LENGTH: 10
<212> TYPE: PRT
<213> ORGANISM: Unknown
<220> FEATURE:
<223> OTHER INFORMATION: Description of Unknown: Antimicrobial peptide

<400> SEQUENCE: 68

Phe Lys Cys Arg Arg Trp Gln Trp Arg Met
1               5                   10

<210> SEQ ID NO 69
<211> LENGTH: 10
<212> TYPE: PRT
<213> ORGANISM: Vigna sesquipedalis

<400> SEQUENCE: 69

Lys Thr Cys Glu Asn Leu Ala Asp Thr Tyr
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Leu Phe Asp Ile Ile Lys Lys Ile Ala Glu Ser Phe
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ala Phe Asp Ile Ile Lys Lys Ile Ala Glu Ser Phe
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Leu Ala Asp Ile Ile Lys Lys Ile Ala Glu Ser Phe
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Phe Ala Ile Ile Lys Lys Ile Ala Glu Ser Phe
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Leu Phe Asp Ala Ile Lys Lys Ile Ala Glu Ser Phe
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Leu Phe Asp Ile Ala Lys Lys Ile Ala Glu Ser Phe
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Leu Phe Asp Ile Ile Ala Lys Ile Ala Glu Ser Phe
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 77

Gly Leu Phe Asp Ile Ile Lys Ala Ile Ala Glu Ser Phe
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Leu Phe Asp Ile Ile Lys Lys Ala Ala Glu Ser Phe
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Leu Phe Asp Ile Ile Lys Lys Ile Ala Ala Ser Phe
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Leu Phe Asp Ile Ile Lys Lys Ile Ala Glu Ala Phe
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Leu Phe Asp Ile Ile Lys Lys Ile Ala Glu Ser Ala
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Leu Phe Asp Ile Ile His Lys Ile Ala Glu Ser Phe
1               5                   10

<210> SEQ ID NO 83
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Gly Leu Phe Asp Ile Ile Lys His Ile Ala Glu Ser Phe
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Leu Phe Asp Ile Ile Lys Lys Ile Ala His Ser Phe
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Leu Phe Asp Ile Ile Arg Lys Ile Ala Glu Ser Phe
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Leu Phe Asp Ile Ile Lys Arg Ile Ala Glu Ser Phe
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Leu Phe Asp Ile Ile Lys Lys Ile Ala Arg Ser Phe
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Leu Phe Asp Ile Ile Lys Lys Ile Ala Asp Ser Phe
1               5                   10
```

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Pro Glu Thr Gly Gly
1               5

<210> SEQ ID NO 90
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
gggacagaac atccccagga gttttagagc tagaaatagc aagttaaaat aaggctagtc    60
cgttatcaac ttgaaaaagt ggcaccgagt cggtgctttt ttt                     103

<210> SEQ ID NO 91
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
ggtgggacag aacatcccca gggttttaga gctagaaata gcaagttaaa ataaggctag    60
tccgttatca acttgaaaaa gtggcaccga gtcggtgctt ttttt                   105

<210> SEQ ID NO 92
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gggtgggaca gaacatcccc gttttagagc tagaaatagc aagttaaaat aaggctagtc    60
cgttatcaac ttgaaaaagt ggcaccgagt cggtgctttt ttt                     103

<210> SEQ ID NO 93
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gggacagaac ttccccagga gttttagagc tagaaatagc aagttaaaat aaggctagtc    60
cgttatcaac ttgaaaaagt ggcaccgagt cggtgctttt ttt                     103

<210> SEQ ID NO 94
<211> LENGTH: 105
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 94
ggtgggacag aacttcccca gggttttaga gctagaaata gcaagttaaa ataaggctag      60
tccgttatca acttgaaaaa gtggcaccga gtcggtgctt ttttt                    105

<210> SEQ ID NO 95
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gggtgggaca gaacttcccc gttttagagc tagaaatagc aagttaaaat aaggctagtc      60
cgttatcaac ttgaaaaagt ggcaccgagt cggtgctttt ttt                      103

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Pro Glu Thr Gly Gly Gly
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 97

His His His His His His His His His His
1               5                   10

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 98

His His His His His His
1               5

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

```
Gly Gly Gly Lys
1

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Pro Glu Thr Gly His His His His His
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

His His His His His His Glu Asn Leu Tyr Phe Gln
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Arg Arg Arg Arg Arg Arg Arg
1               5
```

EFFICIENT DELIVERY OF THERAPEUTIC MOLECULES IN VITRO AND IN VIVO

CROSS REFERENCE TO RELATED APPLICATIONS

This is a national stage filing in accordance with 35 U.S.C. § 371 of PCT/US2015/058096, filed Oct. 29, 2015, which claims the benefit of the priority of U.S. Provisional Patent Application No. 62/072,209, filed Oct. 29, 2014, the contents of each are incorporated herein by reference.

FIELD OF THE INVENTION

The present invention relates to protein therapeutics including genome-editing. Embodiments are directed to delivery of proteins that are fused to an anionic molecule, antimicrobial or membrane destabilization molecules. These anionic molecules include, an oligonucleotide, a polynucleotide, negatively supercharged proteins, that contain natural anionic domains, or that natively bind to anionic nucleic acids.

BACKGROUND

Therapeutic proteins including peptide hormones, cytokines, and monoclonal antibodies have achieved widespread success as research tools and are among the fastest growing classes of drugs. Many powerful and potentially therapeutic proteins have been discovered or engineered over the past two decades, including enzymes capable of metabolic complementation (Hartung, S. D. et al. *Gene. Mol. Ther.* 9, 866-875 (2004)), neutralizing antibodies against intracellular targets (Wang, J. et al. *Nat. Biotechnol.* 26, 901-908 (2008)), engineered transcription factors (Urnov, F. D., et al. *Nat. Rev. Genet.* 11, 636-646 (2010)), and programmable genome-editing enzymes (Sander, J. D. & Joung, J. K. *Nat. Biotechnol.* 32, 347-355 (2014); Gaj, T., et al. *Trends Biotechnol.* 31, 397-405 (2013)). While protein biologics have proven effective for extracellular targets, their use to address intracellular targets is comparatively undeveloped due to the inability of most proteins to spontaneously enter mammalian cells. Enabling exogenous proteins to access intracellular targets is most commonly achieved by delivery of their encoding DNA sequences through chemical transfection (Midoux, P., et al. *Br. J. Pharmacol.* 157, 166-178 (2009)), electroporation (Bodles-Brakhop, A. M., et al. *Mol. Ther.* 17, 585-592 (2009)), or viral delivery (Kay, M. A., et al. *Nat. Med.* 7, 33-40 (2001)). The introduction of exogenous DNA into cells, however, raises the possibility of permanent recombination into the genome, potential disruption of endogenous genes, and long-term exposure to the encoded agent. For some research or therapeutic applications, including genome editing applications that seek to effect a one-time, permanent modification of genomic DNA, the functional delivery of non-replicable protein agents may offer improved safety or broader applicability.

The recent development of methods to deliver in vitro transcribed mRNAs or mRNA analogs has offered an alternative to DNA delivery without requiring nuclear transport of an encoding gene, and with greatly reduced potential for genomic insertion of the foreign nucleic acid. While promising, mRNA delivery continues to face challenges including immunogenicity and RNA stability. While chemical modifications and the inclusion of base analogs can mitigate some of these issues, the large-scale production of high-quality modified mRNAs remains a challenge (Zangi, L. et al. *Nat. Biotechnol.* 31, 898-907 (2013)). Moreover, proteins containing important natural or synthetic post-translational modifications may not be amenable to production by endogenous translation machinery. Therefore, while both DNA and mRNA delivery have become powerful research tools with therapeutic implications, the development of effective and general protein delivery methods remains an important challenge for the molecular life sciences.

Current or conventional protein delivery technologies are based on fusion or conjugation to cationic molecules that facilitate endocytosis, such as unstructured peptides (Wadia, J. S., et al. *Nat. Med.* 10, 310-315 (2004); Daniels, D. S. & Schepartz, A. J. *Am. Chem. Soc.* 129, 14578-14579 (2007)) or engineered superpositively charged proteins (Cronican, J. J. et al. *ACS Chem. Biol.* 5, 747-752 (2010); Thompson, D. B., et al. *Methods Enzymol.* 503, 293-319 (2012); Thompson, D. B., et al. *Chem. Biol.* 19, 831-843 (2012)). While such delivery can be effective in cell culture, and has even shown some success in vivo, cationic protein-based delivery methods have not seen widespread adoption. Unprotected proteins can be rapidly degraded by extracellular and endosomal proteases (Heitz, F., et al. *Br. J. Pharmacol.* 157, 195-206 (2009)), or neutralized by binding to serum proteins, blood cells, and the extracellular matrix (Caron, N. J. et al. *Mol. Ther. J. Am. Soc. Gene Ther.* 3, 310-318 (2001); Chesnoy, S. & Huang, L. *Annu. Rev. Biophys. Biomol. Struct.* 29, 27-47 (2000)). In addition, the low efficiency of endosomal escape and avoidance of lysosomal degradation are major challenges to all endocytic protein delivery strategies, as evidenced by ongoing interest in endosome altering (Thompson, D. B., et al. *Chem. Biol.* 19, 831-843 (2012); Al-Taei, S. et al. *Bioconjug. Chem.* 17, 90-100 (2006)) and destabilizing strategies (Shete, H. K., *J. Nanosci. Nanotechnol.* 14, 460-174 (2014)). These challenges have proven especially difficult in vivo (Aguilera, T. A., et al. *Integr. Biol. Quant. Biosci. Nano Macro* 1, 371-381 (2009)).

Nucleic acid delivery has benefited greatly from the development of liposomal reagents over the past two decades. Cationic lipid formulations have enabled DNA and RNA transfection to become a routine technique in basic research and have even been used in clinical trials (Coelho, T. et al. *N. Engl. J. Med.* 369, 819-829 (2013)). The lipid bilayer of the vehicle protects encapsulated nucleic acids from degradation and can prevent neutralization by antibodies (Judge, A. D., et al. *Mol. Ther. J. Am. Soc. Gene Ther.* 13, 494-505 (2006)). Importantly, fusion of liposomes with the endosomal membrane during endosome maturation can enable the efficient endosomal escape of cationic lipid-delivered cargo (Basha, G. et al. *Mol. Ther. J. Am. Soc. Gene Ther.* 19, 2186-2200 (2011)). More advanced reversibly ionizable lipid nanoparticles enable efficient encapsulation and delivery of nucleic acids, while avoiding non-specific electrostatic interactions and sequestration (Semple, S. C. et al. *Nat. Biotechnol.* 28, 172-176 (2010)).

Because proteins, in contrast to nucleic acids, are chemically diverse with no dominant electrostatic property, no lipid formulation is likely to drive the efficient delivery of all proteins into mammalian cells. While proteins can be encapsulated non-specifically and delivered by rehydrated lipids in vitro (Boeckle, S., et al. *J. Control. Release Off. J. Control. Release Soc.* 112, 240-248 (2006); Allen, T. M. & Cullis, P. R. *Adv. Drug Deliv. Rev.* 65, 36-48 (2013)), the efficacy of encapsulation is dependent on protein concentration, is generally inefficient (Zelphati, O. et al. *J. Biol. Chem.* 276, 35103-35110 (2001)), and has not seen widespread application. Specialty commercial reagents developed specifically for protein delivery (Adrian, J. E. et al. *J.*

Control. Release Off. J. Control. Release Soc. 144, 341-349 (2010); Morris, M. C., et al. *Nat. Biotechnol.* 19, 1173-1176 (2001)) have also failed to garner popularity perhaps due to their low potency and unreliability with a variety protein cargoes (Colletier, J.-P., et al. *BMC Biotechnol.* 2, 9 (2002)).

SUMMARY

Embodiments of the invention are directed to compositions comprising therapeutically effective anionically charged molecules and compositions for their efficient and specific delivery in vitro and in vivo. Targeted cells include any cells associated with hearing, including neurons, stem cells, hair cells, supporting cells and the like.

In an embodiment, a method of treating deafness or disorders thereof, associated with a genetic mutation in a patient in need thereof, comprises administering to an inner ear of the patient a therapeutically effective amount of a chimeric molecule comprising at least one protein or peptide fused, complexed or linked to one or more one or more gene editing agents, transcriptional modulators, translational modulators, post-translational modulators, and/or modulators that regulate protein expression, function, activity or combinations thereof. The chimeric molecule targets one or more genetic loci associated with deafness in a patient and modulates replication, expression, function or activity of the genetic locus in inner ear cells comprising, strial vascularis, neurons, hair cells, stem cells, or supporting cells. The chimeric molecule comprises a supercharged protein or variants thereof, for example, the supercharged protein is green fluorescent protein (s-GFP), or variants thereof. The gene editing agents comprise: transcriptional activators, transcriptional repressors, recombinases, nucleases, DNA-binding proteins or nucleic acids, or combinations thereof. In some embodiments, the gene editing agents comprise: Cre recombinases, CRISPR/Cas molecules, TALE transcriptional activators, Cas9 nucleases, nickases, transcriptional regulators or combinations thereof.

In an embodiment, the supercharged protein further comprises a membrane destabilization protein, such, as for example, aurein, which is linked to the s-GFP or variants thereof.

In some embodiments the chimeric molecule is encapsulated in a cationic lipid formulation.

In embodiments, the chimeric molecules target different chromosomal abnormalities, such as, for example, deletion, insertion, duplication, inversion and the like. The chimeric molecules are suitable therapeutics where monogenic, bigenic or multigenic mutations contribute to hearing loss. Accordingly, in other embodiments, the chimeric molecules target multiple genes.

In another embodiment, a method of correcting, silencing or modifying a genetic mutation associated with deafness or disorders thereof, in a patient, comprises administering to a patient's inner ear, a cationic liposome encapsulating a therapeutically effective amount of a molecule comprising a supercharged protein or peptide fused, complexed or linked to one or more one or more gene editing agents, transcriptional modulators, translational modulators, post-translational modulators, and/or modulators that regulate gene expression, protein expression, function, activity or combinations thereof. The molecule targets one or more genetic loci having a mutation associated with deafness or disorders thereof, in a patient, wherein the molecule corrects, silences or modifies a genetic mutation inner ear cells comprising, strial vascularis, hair cells, stem cells, or supporting cells. For gene editing such as CRISPR, Cas9 (protein) is complexed with gRNA (guide RNA, nucleic acid) with/without a template by liposome. Such complex can then be delivered to inner ear for gene editing. For the disruption of mutation, only gRNA without template is needed; whereas for mutation repair, both a gRNA and a template are needed; in addition to Cas9.

In another embodiment, a method of correcting, silencing or modifying a genetic mutation in hair cells, stem cells, and/or supporting cells in vitro or in vivo, comprises contacting a hair cell or supporting cell or administering to a patient's inner ear, a therapeutically effective amount of a molecule comprising a supercharged protein or peptide fused, complexed or linked to one or more one or more gene editing agents, transcriptional modulators, translational modulators, post-translational modulators, and/or modulators that regulate protein expression, function, activity or combinations thereof. The molecule targets one or more genetic loci having a mutation associated with deafness or disorders thereof, in a patient, wherein the molecule corrects, silences or modifies a genetic mutation in hair cells and supporting cells of the inner ear.

In another embodiment, a method of delivering a therapeutic molecule to cells of an inner ear of a patient, comprises administering to the inner ear of a patient a chimeric molecule comprising at least one protein or peptide fused, complexed or linked to one or more anionic molecules. In an embodiment, the cells of the inner ear comprise hair cells, supporting cells, or combinations thereof. In an embodiment, the chimeric molecule comprises one or more gene editing agents, transcriptional modulators, translational modulators, post-translational modulators, and/or modulators that regulate gene expression, protein expression, function, activity or combinations thereof. The gene editing agents comprise: transcriptional activators, transcriptional repressors, recombinases, nucleases, DNA-binding proteins or nucleic acids, or combinations thereof. In an embodiment, the anionic molecules comprise: oligonucleotides, polynucleotides, proteins, peptides, peptide nucleic acids (PNA), synthetic molecules or combinations thereof. The oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof. In other embodiments, the chimeric molecule comprises a supercharged protein or variants thereof. An example of a supercharged protein is a fluorescent protein, or variants thereof. The chimeric molecule further comprises a membrane destabilizing protein, for example, aurein.

In some embodiments, the chimeric molecule is encapsulated in a cationic lipid formulation.

In some embodiments, a composition comprises a cationic lipid encapsulating one or more chimeric molecules comprising one or more proteins or peptides fused, complexed or linked to one or more anionic molecules. These one or more anionic molecules confer an overall net negative charge to the chimeric molecule and comprise one or more anionic domains or bind to an anionic nucleic acid domain. In some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof.

In embodiments, the one or more proteins or peptides are cationic, anionic or are neutrally charged. In some embodiments, the proteins or peptides comprise: enzymes, hormones, chemotherapeutic agents, immunotherapeutic agents, gene editing agents, synthetic molecules or combinations thereof. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

In other embodiments, methods of treatment comprises administering a therapeutically effective amount of a cationic lipid encapsulating one or more chimeric molecules comprising one or more proteins or peptides fused, complexed or linked to one or more anionic molecules.

Other aspects are described infra.

BRIEF DESCRIPTION OF THE DRAWINGS

FIG. 2 is a schematic representation showing a design of gRNA for Cas9:gRNA (SEQ ID NOS: 21-33) injection. Mutation 2765C→T was shown. Multiple gRNAs, some target the mutation and some target wildtype Pmca2 gene were designed for injection with Cas9.

FIG. 6A: Two months after injection, a majority of outer hair cells are seen in the base compared to a complete outer hair cell loss in the uninjected control ear. FIG. 6B: Cell count showed general preservation of outer hair cells across all frequencies after Cas9:gRNA injection two months later. In contrast to almost complete outer hair cell loss at high-frequencies 32 and 45.25 kHz, outer hair cell number in the injected inner ears was virtually intact.

FIGS. 7A, 7B is a color stain showing the preservation of ganglion neurites in the Cas9:gRNA injected cochlea. FIG. 7A: In the control uninjected inner ear of $Pmca2^{Obl/+}$ mice, TuJ labeling of neurites is largely absent in the region between outer hair cells (OHCs) and inner hair cells (IHCs) (Bracket demarcates the region). FIG. 7B: In the injected inner ear in contrast, preservation of neurites is seen by a large number of $TuJ^+$ fibers. Parv: parvalbumin that labels hair cells.

FIG. 8 is a series of graphs showing the hearing rescue by Cas9:gRNA in the Bth heterozygous mice. 4 weeks after injection, significant hearing improvement is observed in the middle frequencies of 11.32 to 32.64 kHz in the injected ears comparing to control uninjected inner ears. The DPOAE is similar with the exception at 11.32 kHz whereas injected ears showed elevated DPOAE threshold shift.

FIG. 10A: The scala media (cochlear duct) of P0 floxP-tdTomato mice (n=4) were injected with 0.3 µL of 23 µM (−30)GFP-Cre in 50% RNAiMAX or with RNAiMAX alone (control). After 5 days, tdTomato expression indicative of Cre-mediated recombination was visualized using immunohistology. Red=tdTomato; green=Myo7a; white=Sox2; blue=DAPI. Yellow brackets indicate the outer hair cell (OHC) region. FIG. 10B: Ten days after (−30)GFP-Cre delivery, intact espin (Esp)-expressing stereocilia of tdTomato-positive outer hair cells were present (arrow), similar to stereocilia in control cochlea. Red=tdTomato; green=Esp, white=Sox2; blue=DAPI, Scale bars: 10 µm.

FIG. 11A: At 5 µM, tdT labeling was mainly in some IHC and SC. FIG. 11B: At 22.5 µM, tdT labeling was in most IHC and OHC, and in some SC and spiral ganglion neurons (SPN). FIG. 11C: At 50 µM, tdT was seen in most IHC and OHC, as well as a large number of SC. IHC loss was seen under the condition. FIG. 11D: In mice injected with 50 µM (+36) GFP-Cre, very few IHC and HC were labeled with tdT. FIG. 11E: In Opti-MEM injected control mice no tdT labeling was detected in any inner ear cells. Scale bars: 10 µm.

FIG. 15A shows that the cytosolic Cre delivery results in recombination and tdTomato expression. The percentage of tdTomato positive cells was determined by flow cytometry. Protein fusions were delivered at 125 nM, 250 nM, 500 nM, and 1 µM. FIG. 15B shows the toxicity of aurein 1.2 and citropin 1.3 as determined by CELLTITERGLO (Promega) assay. Protein fusions were delivered at 125 nM, 250 nM, 500 nM, and 1 µM. The labeled concentration of +36 GFP-Cre was used as the no peptide control (NP), and addition of 100 µM chloroquine was used as the positive control (+). Cells were treated with 250 nM protein for 4 h in serum-free media. Cells were washed and supplanted with full DMEM and incubated for 48 h. Error bars represent the standard deviation of three independent biological replicates.

(FIG. 16B) Toxicity as determined by CELLTITERGLO (Promega) assay. 250 nM+36 GFP-Cre was used as the no peptide control (NP), and addition of 100 µM chloroquine was used as the positive control (+). Cells were treated with 250 nM protein for 4 h in serum-free DMEM. Cells were washed and supplanted with full DMEM and incubated for 48 h.

FIG. 17A shows images of HeLa cells expressing GR-mCherry treated in the presence and absence of 1 µM dexamethasone (Dex)-protein conjugates for 30 min at 37° C. FIG. 17B shows that nuclear-to-cytosol GR-mCherry fluorescence ratios (translocation ratios) of respective Dex-protein conjugates determined using CELLPROFILER®. FIG. 17C shows the GR-mCherry translocation ratios resulting from cells treated in the presence and absence of +36 GFP$^{Dex}$ and endocytic inhibitors. FIG. 17D shows the GR-mCherry translocation ratios resulting from cells treated in the presence and absence of aurein 1.2-+36 GFP$^{Dex}$ and endocytic inhibitors. Statistical significance is measured by P-value. ns=P>0.05, *=P≤0.05, =P≤0.01, *=P≤0.001. FIG. 17 discloses "Arg8" disclosed as SEQ ID NO: 102.

FIG. 18A: Five days after injection, cochlea were harvested. Inner hair cells (IHC), outer hair cells (OHC) and supporting cells in the sensory epithelium (SE) were imaged for the presence of tdTomato, which is only expressed following Cre-mediated recombination. Hair cells were labeled with antibodies against the hair-cell marker Myo7a. Gray/white=Myo7a, Red=tdTomato, Blue=DAPI. FIG. 18B: To evaluate cytotoxicity, the number of outer hair cells and inner hair cells were measured by counting DAPI-stained cells. FIG. 18C: The percentage of tdTomato positive cells, reflecting successful delivery of functional Cre recombinase, was determined by fluorescence imaging.

DETAILED DESCRIPTION

Figures 1A, 1B:
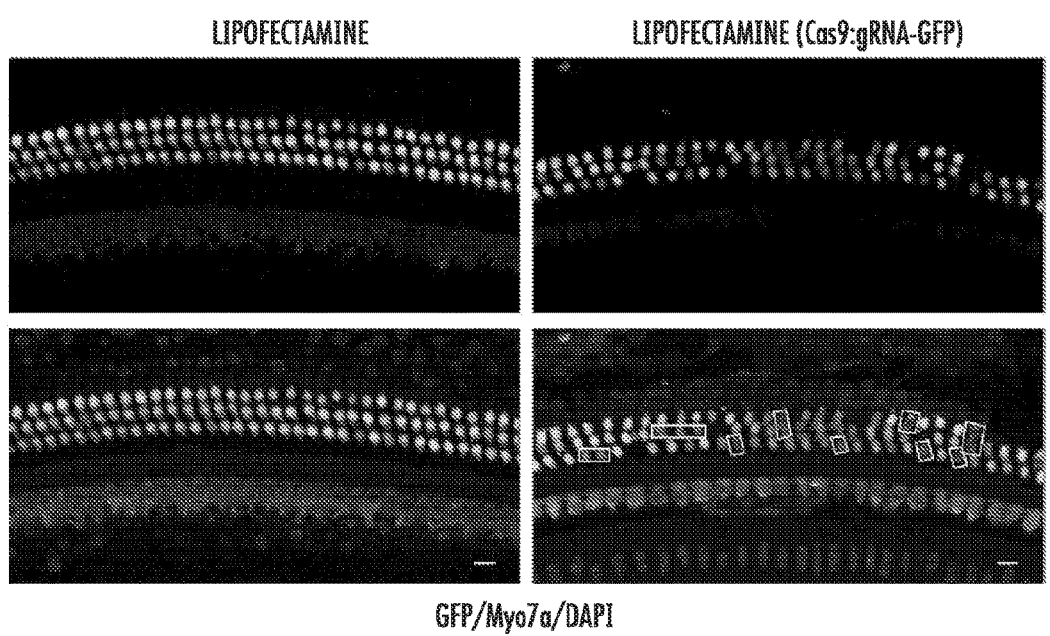
FIGS. 1A, 1B show that after microinjection with Cas9 protein and gRNA complexed with lipofectamine2000, OHCs labeled with Myo7a/DAPI without GFP were seen in the adult Atoh1-GFP transgenic cochlea, a demonstration of genome editing. The efficiency is ~15%. In control cochlea injected with saline, all cochlear OHCs were positive for GFP, a demonstration of specificity of Cas9:gRNA in genome editing in adult cochlea in vivo.

Embodiments of the invention are directed to compositions for the efficient intracellular delivery of proteins to the nucleus or cytoplasm. Conventional methods of protein delivery typically rely on cationic peptides or proteins to facilitate endocytosis, but suffer from low tolerance for serum proteins, poor endosomal escape, and limited in vivo efficacy. Herein, it is reported that cationic lipid reagents can potently deliver to hair cells and supporting cells, proteins that are fused to polynucleotides, oligonucleotides, negatively supercharged proteins, that contain natural anionic domains, or that natively bind to anionic nucleic acids.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

The following description of the preferred embodiments is merely exemplary in nature and is in no way intended to limit the invention, its application or uses. Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

"Optional" or "optionally" means that the subsequently described event or circumstance can or cannot occur, and that the description includes instances where the event or circumstance occurs and instances where it does not.

As used herein, a "chimeric" molecule is one which comprises one or more unrelated types of components or contain two or more chemically distinct regions or domains which can be conjugated to each other, fused, linked, translated, attached via a linker, chemically synthesized, expressed from a nucleic acid sequence, etc. For example, an antimicrobial or membrane destabilizing peptide and an unrelated peptide, a peptide and a nucleic acid sequence, a peptide and a detectable label, unrelated peptide sequences, unrelated nucleic acid sequence and the like.

The term "anionic" molecule is one which comprises one or more "anionic" domains which confer an overall net anionic charge to the molecule. Accordingly, the chimeric molecule can be an anionic molecule.

A "supercharged" molecule is a molecule e.g. peptide, having a positive or negative charge and when it is connected to another molecule confers an overall positive or negative charge to the entire molecule.

As used herein, a "membrane destabilizing domain" is one which disrupts a cellular membrane in vitro or in vivo, for example, aurein. The term encompasses proteins, peptides, polynucleotides, oligonucleotides, bacterial or viral molecules, antimicrobial peptides (AMP), antibacterial molecules, microtubules, synthetic or natural molecules. A chimeric molecule embodied herein, further comprises one or more membrane destabilizing domains.

As used herein, the terms "associated with," "conjugated," "linked," "attached," and "tethered," when used with respect to two or more moieties, means that the moieties or domains are physically associated or connected with one another, either directly or via one or more additional moieties that serves as a linking agent, to form a structure that is sufficiently stable so that the moieties remain physically associated under the conditions in which the structure is used, e.g., physiological conditions. The term "connected" will be used for the sake of brevity and is meant to include all possible methods of physically associating each domain of the chimeric molecule to each other. For example, a supercharged protein is typically associated with or connected to a nucleic acid by a mechanism that involves non-covalent binding (e.g., electrostatic interactions). In certain embodiments, a positively charged, supercharged protein is associated with a nucleic acid through electrostatic interactions to form a complex. In some embodiments, a sufficient number of weaker interactions can provide sufficient stability for moieties to remain physically associated under a variety of different conditions. In certain embodiments, the agent to be delivered is covalently bound to the supercharged protein.

As used herein, the term "green fluorescent protein" (GFP) refers to a protein originally isolated from the jellyfish *Aequorea victoria* that fluoresces green when exposed to blue light or a derivative of such a protein (e.g., a supercharged version of the protein). The amino acid sequence of wild type GFP is as follows: (SEQ ID NO: 20) MSKGEELFTG VVPILVELDG DVNGHKFSVS GEGEGDATYG KLTLKFICTT GKLPVPWPTL VTTFSYGVQC FSRYPDHMKQ HDFFKSAMPE GYVQERTIFF KDDGNYKTRA EVKFEGDTLV NRIELKGIDF KEDGNILGHK LEYNYNSHNV YIMADKQKNG IKVNFKIRHN IEDGSVQLAD HYQQNTPIGD GPVLLPDNHY LSTQSALSKD PNEKRDHMVL LEFVTAAGIT HGMDELYK.

Proteins that are at least 70%, at least 75%, at least 80%, at least 85%, at least 90%, at least 95%, at least 98% or at least 99% homologous are also considered to be green fluorescent proteins. In certain embodiments, the green fluorescent protein is supercharged. In certain embodiments, the green fluorescent protein is superpositively charged (e.g., +15 GFP, +25 GFP, and +36 GFP). In certain embodiments, the GFP may be modified to include a polyhistidine tag for ease in purification of the protein. In certain embodiments, the GFP may be fused with another protein or peptide (e.g., hemagglutinin 2 (HA2) peptide). In certain embodiments, the GFP may be further modified biologically or chemically (e.g., post-translational modifications, proteolysis, etc.).

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

As used herein, a "nucleic acid" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

The term "target nucleic acid" refers to a nucleic acid (often derived from a biological sample), to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA) whose expression level it is desired to detect. The difference in usage will be apparent from context.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-($C_3$-$C_6$)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature Biotechnology* 19:17-18 (2001); Manoharan M., *Biochemica et Biophysica Acta* 1489:117-139(1999); Freier S. M., Nucleic Acid Research, 25:4429-4443 (1997), Uhlman, E., *Drug Discovery & Development*, 3: 203-213 (2000), Herdewin P., *Antisense & Nucleic Acid Drug Dev.*, 10:297-310 (2000)); 2'-O, 3'-C-linked [3.2.0] bicycloarabinonucleosides (see e.g. N. K Christiensen., et al., *J. Am. Chem. Soc.*, 120: 5458-5463 (1998). Such analogs include synthetic nucleosides designed to enhance binding properties, e.g., duplex or triplex stability, specificity, or the like.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As defined herein, an "effective" amount of a compound or agent (i.e., an effective dosage) means an amount sufficient to produce a (e.g., clinically) desirable result.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

As used herein, the term "kit" refers to any delivery system for delivering materials. Inclusive of the term "kits" are kits for both research and clinical applications. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides or liposomes. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

General Techniques

For further elaboration of general techniques useful in the practice of this invention, the practitioner can refer to standard textbooks and reviews in cell biology, tissue culture, embryology, and physiology.

With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (M. V. Wiles, *Meth. Enzymol.* 225:900, 1993); Properties and uses of Embryonic Stem Cells: Prospects for Application to Human Biology and Gene Therapy (P. D. Rathjen et al., *Reprod. Fertil. Dev.* 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Supercharged Proteins

Supercharged proteins can be produced by changing non-conserved amino acids on the surface of a protein to more polar or charged amino acid residues. The amino acid residues to be modified may be hydrophobic, hydrophilic, charged, or a combination thereof. Supercharged proteins can also be produced by the attachment of charged moieties to the protein in order to supercharge the protein. Supercharged proteins frequently are resistant to aggregation, have an increased ability to refold, resist improper folding, have improved solubility, and are generally more stable under a wide range of conditions, including denaturing conditions such as heat or the presence of a detergent.

Any protein may be modified using the inventive system to produce a supercharged protein. Natural as well as unnatural proteins (e.g., engineered proteins) may be modified. Example of proteins that may be modified include receptors, membrane bound proteins, transmembrane proteins, enzymes, transcription factors, extracellular proteins, therapeutic proteins, cytokines, messenger proteins, DNA-binding proteins, RNA-binding proteins, proteins involved in signal transduction, structural proteins, cytoplasmic proteins, nuclear proteins, hydrophobic proteins, hydrophilic proteins, etc. A protein to be modified may be derived from any species of plant, animal, and/or microorganism. In certain embodiments, the protein is a mammalian protein. In certain embodiments, the protein is a human protein. In certain embodiments, the protein is derived from an organism typically used in research. For example, the protein to be modified may be from a primate (e.g., ape, monkey), rodent (e.g., rabbit, hamster, gerbil), pig, dog, cat, fish (e.g., *Danio rerio*), nematode (e.g., *C. elegans*), yeast (e.g., *Saccharomyces cerevisiae*), or bacteria (e.g., *E. coli*). In certain embodiments, the protein is non-immunogenic. In certain embodiments, the protein is non-antigenic. In certain embodiments, the protein does not have inherent biological activity or has been modified to have no biological activity. In certain embodiments, the protein is chosen based on its targeting ability. In certain embodiments, the protein is green fluorescent protein.

Compositions and Treatments

Disclosed herein are compositions for gene editing of cells of the inner ear, and any cell, damaged or otherwise, associated with hearing and hearing loss, such as, for example, stem cells, hair cells, supporting cells, neurites, strial vascularis and the like. In particular, the targeted cells are the hair cells and supporting cells. The compositions, embodied herein, edit mutations associated with deafness or disorders thereof, in hair cells and supporting cells. Hair cells are inner ear sensory cells, including inner hair cells, outer hair cells, and vestibular hair cells. Supporting cells include Deiters cells, Hensen cells, Pillar cells, inner phalangeal cells, inner border cells, Claudius cells, border cells, basal cells, interdental cells, inner sulcus, spiral limbus.

Hearing loss affects a large portion of population yet no treatment is available beyond hearing aids and cochlear implant, both of which provide limited benefits. In the US alone, over 30 millions of people suffer from hearing loss. The major cause of hearing loss in human is due to irreversible loss of the inner ear sensory cells, hair cells, which are responsible for detecting sounds and sensing balance. Further hearing loss can be caused by defective cell types in the inner ear such as strial vascularis and supporting cells, whose regeneration could lead to restoration of hearing.

Accordingly, embodiments are directed to protein-mediated delivery systems to deliver the biological proteins directly to inner ear cell types with functional consequences. With these methods, the proteins delivered have specific functions, and the effect is transient. Further delivery of native protein lessens any potential immune response. Such an approach would not only be valuable for inner ear delivery, but has far reaching effects on the delivery of proteins targeting different diseases, achieving specific effects in multiple organs and cell types.

For efficient protein delivery, proteins need to enter cells with sufficient amount, and are released from endosomes within cells and reach the targets. Improvement in the endosome release could have drastic effects on the amount of protein to reach the target with enhanced biological effect. Antimicrobial or membrane destabilizing peptides, for example, Aurein, in combination with s-GFP, can serve as an effective carrier to deliver functional proteins into mouse inner ear cell types with high efficiency.

High-efficiency delivery of functional proteins in the inner ear has tremendous advantage over conventional systems, including (1). It allows the delivery of unlimited combinations of proteins to mammalian inner ear without limitations on the size or localization of proteins delivered; (2). The effect will be specific; (3). The effect will be transient as delivered proteins will be degraded over time, which allows the modification of proteins (e.g., to reduce the response to degradation pathway) and controls the time length of function. The delivery system can be used to study protein functions, therapeutics for hearing recovery, hearing protection, and gene editing to correct genetic deafness by genome-editing proteins.

In an embodiment, a method of treating deafness or disorders thereof, associated with a genetic mutation in a patient in need thereof, comprises administering to an inner ear of the patient a therapeutically effective amount of a chimeric molecule comprising at least one membrane destabilizing domain and a protein or peptide fused, complexed or linked to one or more one or more gene editing agents, transcriptional modulators, translational modulators, post-translational modulators, and/or modulators that regulate protein expression, function, activity or combinations thereof. The chimeric molecule targets one or more genetic loci associated with deafness in a patient and modulates replication, expression, function or activity of the genetic locus in hair cells and supporting cells of the inner ear. The chimeric molecule comprises a supercharged protein or variants thereof, for example, the supercharged protein is green fluorescent protein (s-GFP), or variants thereof. The gene editing agents comprise: transcriptional activators, transcriptional repressors, recombinases, nucleases, DNA-binding proteins or nucleic acids, or combinations thereof. In some embodiments, the gene editing agents comprise: Cre recombinases, CRISPR/Cas molecules, TALE transcriptional activators, Cas9 nucleases, nickases, transcriptional regulators or combinations thereof.

In embodiments, the chimeric molecules target different chromosomal abnormalities, such as, for example, deletion, insertion, duplication, inversion and the like. The chimeric molecules are suitable therapeutics where bi-genic or multi-genic mutations contribute to hearing loss. CRISPR technology is well suited to target multiple genes.

In an embodiment, a membrane destabilizing domain comprises one or more of: antimicrobial or membrane destabilizing proteins or peptides, polynucleotides, oligonucleotides, bacterial or viral (e.g. reovirus outer capsid protein or peptide, µ1; papilloma virus capsid protein or peptide L2; etc.), antibacterial molecules, microtubules, lipids, synthetic or natural molecules. Membrane destabilization peptides are known in the art. See, for example, Fernandez, D. I. et al., *Biochim. Biophys. Acta,* 2009 August; 1788(8):1630-8. Antimicrobial peptides (AMPs) are a class of membrane-active peptides that penetrate microbial membranes to provide defense against bacteria, fungi, and viruses, often with high selectivity (Zasloff, M. *Nature* 2002, 415, 389).

In an embodiment, the supercharged protein further comprises a membrane destabilization protein, such as for example, aurein, which is linked to the s-GFP or variants thereof. Accordingly, in one embodiment the chimeric molecule comprises a supercharged molecule connected to a membrane destabilization domain which in turn is connected to one or more gene editing agents, transcriptional activators, transcriptional repressors, recombinases, nucleases, DNA-binding proteins or nucleic acids, or combinations thereof. In another embodiment the chimeric molecule comprises a supercharged molecule connected to a membrane destabilization domain which in turn is connected to a gene editing agent, transcriptional activators, transcriptional repressors, recombinases, nucleases, DNA-binding proteins or nucleic acids, or combinations thereof. In another embodiment the chimeric molecule comprises one or more membrane destabilization domains connected to one or more gene editing agents, transcriptional activators, transcriptional repressors, recombinases, nucleases, DNA-binding proteins or nucleic acids, or combinations thereof. In another embodiment, the chimeric molecule comprises a membrane destabilization domain connected to a supercharged molecule which in turn is connected to one or more gene editing agents, transcriptional activators, transcriptional repressors, recombinases, nucleases, DNA-binding proteins or nucleic acids, or combinations thereof. One of ordinary skill in the art would understand that there are a multitude of configurations which can be obtained. Accordingly if the letter "S" represents the supercharged domain, the letter "M" represents the antimicrobial or membrane destabilizing domain, and the letter "X" represents the therapeutic molecules responsible for correcting, silencing or modifying a genetic mutation, then the molecular structure of the molecule can be S-M-X, or M-X-X, or S-M-M-X, or S-S-M-M-X, etc. In those cases where there are two or more molecules that comprise a domain, these domains can comprise different molecules or they can be the same molecule. One of ordinary skill in the art would understand the possible configurations that can be possible.

In another embodiment, a chimeric molecule comprises any one or more sequences SEQ ID NOS: 1 to 95 linked to an antimicrobial or membrane destabilization domain. The antimicrobial or membrane destabilization domain can be connected to the supercharged domain on one end and to therapeutic molecules on the other end (e.g. upstream or downstream).

In some embodiments the chimeric molecule is encapsulated in a cationic lipid formulation.

In another embodiment, a chimeric molecule comprises any two or more proteins, peptides or variants thereof, said proteins, peptides or variants thereof comprising: a supercharged protein or peptide, antimicrobial or membrane destabilizing peptide, gene editing agents, transcriptional activators, transcriptional repressors, recombinases, nucleases, DNA-binding proteins or nucleic acids, or combinations thereof.

In another embodiment, a chimeric molecule comprises any two or more proteins, peptides or variants thereof, said proteins, peptides or variants thereof comprising: a supercharged protein or peptide and an antimicrobial or membrane destabilizing peptide and one or more gene editing agents, transcriptional activators, transcriptional repressors, recombinases, nucleases, DNA-binding proteins or nucleic acids, or combinations thereof.

In another embodiment, a chimeric molecule comprises any two or more proteins, peptides or variants thereof, said proteins, peptides or variants thereof comprising: an antimicrobial or membrane destabilizing domain and one or more supercharged proteins or peptides, gene editing agents, transcriptional activators, transcriptional repressors, recombinases, nucleases, DNA-binding proteins or nucleic acids, or combinations thereof.

In another embodiment, a chimeric nucleic acid molecule encoding any two or more proteins, peptides or variants thereof, said proteins, peptides or variants thereof comprising: a supercharged protein or peptide and an antimicrobial or membrane destabilizing peptide, and one or more gene editing agents, transcriptional activators, transcriptional repressors, recombinases, nucleases, DNA-binding proteins or nucleic acids, or combinations thereof.

In some embodiments, the gene editing agents comprise: Cre recombinases, CRISPR/Cas molecules, TALE transcriptional activators, Cas9 nucleases, nickases, transcriptional regulators or combinations thereof.

In another embodiment, a chimeric molecule comprises a supercharged protein or peptide and an antimicrobial or membrane destabilizing peptide and one or more gene editing agents, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In another embodiment, a chimeric nucleic acid molecule encoding any two or more proteins, peptides or variants thereof, said proteins, peptides or variants thereof comprises a supercharged protein or peptide, antimicrobial or membrane destabilizing domain, gene editing agents, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In another embodiment, a chimeric molecule comprises a nucleic acid molecule encoding a supercharged protein or peptide and an antimicrobial or membrane destabilizing domain and one or more gene editing agents, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In one embodiment, the nucleic acids are gRNA's. See, for example, FIG. 2, SEQ ID NOS: 21-33 and SEQ ID NOS: 90-95. In one embodiment, the gRNA is SEQ ID NO: 26 (FIG. 2; PMCA2-4mut). In another embodiment, the gRNA comprises SEQ ID NOS: 90-95.

Other examples of chimeric molecules comprising gRNA are

```
TMC1-1 WT (SEQ ID NO: 90):
GGGACAGAACATCCCCAGGAGTTTTAGAGCTAGAAATAGCAAGTTAAAAT

AAGGCTAGTCCGTTATCAACTTGAAAAAGTGGCACCGAGTCGGTGCTTTT

TTT

TMC1-2 WT (SEQ ID NO: 91):
GGTGGGACAGAACATCCCCAGGGTTTTAGAGCTAGAAATAGCAAGTTAAA

ATAAGGCTAGTCCGTTATCAACTTGAAAAAGTGGCACCGAGTCGGTGCTT

TTTTT

TMC1-3 WT (SEQ ID NO: 92):
GGGTGGGACAGAACATCCCGTTTTAGAGCTAGAAATAGCAAGTTAAAAT

AAGGCTAGTCCGTTATCAACTTGAAAAAGTGGCACCGAGTCGGTGCTTTT

TTT

TMC1-1 MUT (SEQ ID NO: 93):
GGGACAGAACTTCCCCAGGAGTTTTAGAGCTAGAAATAGCAAGTTAAAAT

AAGGCTAGTCCGTTATCAACTTGAAAAAGTGGCACCGAGTCGGTGCTTTT

TTT

TMC1-2 MUT (SEQ ID NO: 94):
GGTGGGACAGAACTTCCCCAGGGTTTTAGAGCTAGAAATAGCAAGTTAAA

ATAAGGCTAGTCCGTTATCAACTTGAAAAAGTGGCACCGAGTCGGTGCTT

TTTTT

TMC1-3 MUT (SEQ ID NO: 95):
GGGTGGGACAGAACTTCCCCGTTTTAGAGCTAGAAATAGCAAGTTAAAAT

AAGGCTAGTCCGTTATCAACTTGAAAAAGTGGCACCGAGTCGGTGCTTTT

TTT
```

In another embodiment, the chimeric molecule comprises nucleic acid sequences comprising SEQ ID NOS: 21-33, 90-95 or combinations thereof. In another embodiment, the chimeric molecule comprises SEQ ID NOS: 26, 94, 95 or combinations thereof.

In another embodiment, a method of correcting, silencing or modifying a genetic mutation associated with deafness or disorders thereof, in a patient, comprises administering to a patient's inner ear, a cationic liposome encapsulating a therapeutically effective amount of a molecule comprising a supercharged protein or peptide fused, complexed or linked to one or more one or more gene editing agents, transcriptional modulators, translational modulators, post-translational modulators, and/or modulators that regulate protein expression, function, activity or combinations thereof. The molecule targets one or more genetic loci having a mutation associated with deafness or disorders thereof, in a patient, wherein the molecule corrects, silences or modifies a genetic mutation in hair cells and supporting cells of the inner ear.

In another embodiment, a method of correcting, silencing or modifying a genetic mutation associated with deafness or disorders thereof, in a patient, comprises administering to a patient's inner ear, a cationic liposome encapsulating a therapeutically effective amount of a molecule comprising a supercharged protein or peptide and an antimicrobial or membrane destabilizing domain fused, complexed or linked to one or more one or more gene editing agents, transcriptional modulators, translational modulators, post-translational modulators, and/or modulators that regulate protein expression, function, activity or combinations thereof. The molecule targets one or more genetic loci having a mutation associated with deafness or disorders thereof, in a patient, wherein the molecule corrects, silences or modifies a genetic mutation in hair cells and supporting cells of the inner ear.

In another embodiment, a method of correcting, silencing or modifying a genetic mutation in hair cells and/or supporting cells in vitro or in vivo, comprising: contacting a hair cell or supporting cell or administering to a patient's inner ear, a therapeutically effective amount of a molecule comprising an antimicrobial or membrane destabilizing domain, a supercharged protein or peptide fused, complexed or linked to one or more one or more gene editing agents, transcriptional modulators, translational modulators, post-translational modulators, and/or modulators that regulate protein expression, function, activity or combinations thereof. The molecule targets one or more genetic loci having a mutation associated with deafness or disorders thereof, in a patient, wherein the molecule corrects, silences or modifies a genetic mutation in hair cells and supporting cells of the inner ear. For gene editing such as CRISPR, Cas9 (protein) is complexed with gRNA (guide RNA, nucleic acid) with/without a template by liposome. Such complex can then be delivered to inner ear for gene editing. For the disruption of mutation, only gRNA without template is needed; whereas for mutation repair, both a gRNA and a template are needed; in addition to Cas9.

In another embodiment, a method of delivering a therapeutic molecule to cells of an inner ear of a patient, comprises administering to the inner ear of a patient a chimeric molecule comprising at least one protein or peptide fused, complexed or linked to one or more anionic molecules. In an embodiment, the cells of the inner ear comprise hair cells, supporting cells, or combinations thereof. In an embodiment, the chimeric molecule comprises one or more gene editing agents, transcriptional modulators, translational modulators, post-translational modulators, and/or modulators that regulate protein expression, function, activity or combinations thereof. The gene editing agents comprise: transcriptional activators, transcriptional repressors, recombinases, nucleases, DNA-binding proteins or nucleic acids, or combinations thereof. In an embodiment, the anionic molecules comprise: oligonucleotides, polynucleotides, proteins, peptides, peptide nucleic acids (PNA), synthetic molecules or combinations thereof. The oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof. In other embodiments, the chimeric molecule comprises a supercharged protein or variants thereof. An example of a supercharged protein is a fluorescent protein, or variants thereof. The chimeric molecule further comprises a membrane destabilizing protein, for example, aurein.

In some embodiments, a composition comprises a cationic lipid encapsulating one or more chimeric molecules. These chimeric molecules comprise one or more proteins or peptides fused, complexed or linked to one or more anionic molecules. The anionic molecules can vary as long as they comprise one or more anionic domains or bind to an anionic nucleic acid domain. It is preferred that the anionic molecules confer an overall net negative charge to the chimeric molecule. Without wishing to be bound by theory, it was hypothesized that proteins that are engineered to be highly negatively charged or that are naturally highly anionic may be able to take advantage of the same electrostatics-driven complexation and encapsulation used by cationic liposomal reagents for nucleic acid delivery. While few proteins natively possess the density of negative charges found in the phosphate backbone of nucleic acids, it was speculated that translational fusion to, or non-covalent complexation with, a polyanionic molecule may render the resulting protein or protein complex sufficiently anionic to be efficiently complexed by common cationic lipid reagents. The results for the work, described in the Examples section which follows, showed that delivery efficiency depends on the net charge of the fusion protein, and natively anionic peptide tags such as 3×FLAG and VP64 can also enable lipid-mediated protein delivery.

Accordingly, in some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof.

In embodiments, the one or more proteins or peptides of the chimeric or anionic molecule can possess any charge as long as the overall net charge of the chimeric molecule is anionic. Accordingly, in embodiments, the proteins or peptides are cationic, anionic or are neutrally charged. Examples of proteins or peptides of the chimeric molecule which can be complexed or linked to the polyanionic molecule or domain comprise: enzymes, hormones, chemotherapeutic agents, immunotherapeutic agents, gene editing agents, synthetic molecules or combinations thereof.

In some embodiments, the protein or peptide is a therapeutic agent for delivery to a specific target. The target can be any desired intracellular target. In some embodiments, the target is a nucleic acid sequence or gene. In embodiments where it is desired to manipulate, modulate or edit a gene, the protein or peptide is a gene or genome editing agent. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. In some embodiments, the target is a protein or peptide. Accordingly, in some embodiments, the chimeric or anionic molecule comprises one or more gene editing agents, transcriptional modulators, translational modulators, post-translational modulators, and/or modulators that regulate protein expression, function, activity or combinations thereof.

In other embodiments, the chimeric molecule further comprises one or more detectable labels, anions, radiolabels, tags, targeting agents, negatively charged proteins or peptides, or combinations thereof. These molecules can be selected based on the user's desired goal, e.g. for diagnostic or research purposes, or to increase the anionic charge, targeting signals and the like. Accordingly, a liposomal formulation for complexing protein and nucleic acid (e.g. transcription factors with their target binding region as oligonucleotides) for inner ear cell types delivery in vivo, is used to treat deafness or associated disorders thereof as the chimeric molecule can be tailored for regeneration (e.g. hair cell and auditory neuron regeneration), repair (e.g. re-establishment of connections between hair cells and neurons for hearing recovery) and prevention.

In other embodiments, a chimeric molecule comprises at least one protein or peptide fused, complexed or linked to one or more anionic molecules. Preferably, the one or more anionic molecules comprise one or more anionic domains or bind to an anionic nucleic acid domain. In embodiments, the chimeric molecule comprises an overall net negative charge. In some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof. The chimeric molecule also comprises one or more proteins or peptides which are cationic, anionic or are neutrally charged. Examples of proteins include without limitation: enzymes, hormones, chemotherapeutic agents, immunotherapeutic agents, genome or gene editing agents, synthetic molecules or combinations thereof. The gene or genome editing agents comprise: transcriptional activators, transcriptional repressors, recombinases, nucleases, DNA-binding proteins or nucleic acids, or combinations thereof. In other embodiments, the chimeric molecule optionally comprises one or more detectable labels, radiolabels, tags, anions, targeting agents or combinations thereof.

In other embodiments, a cationic liposome encapsulates an anionic molecule comprising a protein or peptide complexed, fused or linked to a negatively charged molecule. In some embodiments, the negatively charged molecule comprises oligonucleotides, polynucleotides, proteins, peptides, peptide nucleic acids (PNA), synthetic molecules or combinations thereof. In other embodiments, the polynucleotide or oligonucleotide is a guide RNA. In some embodiments, the protein or peptide is a negatively charged protein. In yet other embodiments, the one or more proteins or peptides are cationic, anionic or are neutrally charged. In yet another embodiment, the negatively charged protein is fused or linked to one or more proteins or peptides. In some embodiments, the protein or peptide comprises: enzymes, hormones, chemotherapeutic agents, immunotherapeutic agents, gene editing agents, synthetic molecules or combinations thereof. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. Examples of these gene editing agents comprise: Cre recombinases, CRISPR/Cas molecules, TALE transcriptional activators, Cas9 nucleases, nickases, transcriptional regulators or combinations thereof. The anionic molecule optionally comprises one or more detectable labels, radiolabels, tags, negatively charged proteins or peptides, anions, targeting agents or combinations thereof.

In some embodiments, a molecule comprises any one or more sequences comprising SEQ ID NOS: 1 to 95. In another embodiment, a molecule comprises any one or more sequences comprising SEQ ID NOS: 1 to 95, wherein each sequence further comprises one or more antimicrobial or membrane destabilizing domains, for example, aurein or fragments thereof.

In other embodiments, the liposome comprises one or more cationic lipids, modified lipids or combinations thereof.

In some embodiments, a liposome encapsulating one or more molecules embodied herein comprises a liposome, a nanoliposome, a niosome, a microsphere, a nanosphere, a nanoparticle, a micelle, or an archaeosome.

Modified Proteins or Peptides:

Hybrid proteins comprising a polypeptide or fragment thereof may be linked to other types of polypeptides, for example, a negatively supercharged protein, e.g. green fluorescent protein in addition to a reporter polypeptide, or in lieu of a reporter polypeptide. These additional polypeptides may be any amino acid sequence useful for the purification, identification, overall charge of the protein or peptide, and/or therapeutic or prophylactic application of the peptide. In addition, the additional polypeptide can be a signal peptide, or targeting peptide, etc.

In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

Modified Oligonucleotides:

Examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2-NH-O-CH_2$, CH, $-N(CH_3)-O-CH_2$ [known as a methylene(methylimino) or MMI backbone], $CH_2-O-N(CH_3)-CH_2$, $CH_2-N(CH_3)-N(CH_3)-CH_2$ and $O-N(CH_3)-CH_2-CH_2$ backbones, wherein the native phosphodiester backbone is represented as $O-P-O-CH_2$,). The amide backbones disclosed by De Mesmaeker et al. *Acc. Chem. Res.* 1995, 28:366-374) are also embodied herein. In some embodiments, the oligonucleotides having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also comprise one or more substituted sugar moieties. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci.* USA 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

Labeled Molecules:

In another preferred embodiment, the chimeric molecules can be labeled. Uses include therapeutic and imaging for diagnostic and prognostic purposes. The label may be a radioactive atom, an enzyme, or a chromophore moiety. Methods for labeling antibodies have been described, for example, by Hunter and Greenwood, *Nature,* 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc. Natl. Acad. Sci.* USA (1983) 80:4045; Renz and Kurz, *Nucl. Acids Res.* (1984) 12:3435; Richardson and Gumport, *Nucl. Acids Res.* (1983) 11:6167; Smith et al. *Nucl. Acids Res.* (1985) 13:2399; and Meinkoth and Wahl, *Anal. Biochem.* (1984) 138:267.

The label may be radioactive. Some examples of useful radioactive labels include $^{32}P$, $^{125}I$, $^{131}I$, and $^{3}H$. Use of radioactive labels has been described in U.K. 2,034,323, U.S. Pat. No. 4,358,535, and U.S. Pat. No. 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, *Proc. Natl. Acad. Sci.* USA, 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the chimeric molecule by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

In another preferred embodiment, the chimeric fusion molecules of the invention can be used for imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$P can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Reporter genes useful in the present invention include acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Methods of Treatment

The compositions and molecules embodied herein are useful in those diseases and conditions that would benefit from protein therapeutics. In some embodiments, a method of treatment comprises administering to a patient an effective amount of cationic liposome encapsulating a chimeric molecule embodied herein. In other embodiments, the molecule comprises one or more sequences set forth as SEQ ID NOS: 1 to 32.

In another embodiment, a method of treatment comprises administering to a patient a therapeutically effective amount of a chimeric molecule comprising any two or more proteins, peptides or variants thereof, said proteins, peptides or variants thereof comprising: a supercharged protein or peptide, antimicrobial or membrane destabilizing peptide, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In another embodiment, a method of treatment comprises administering to a patient a therapeutically effective amount of a chimeric molecule comprising any two or more proteins, peptides or variants thereof, said proteins, peptides or variants thereof comprising: a supercharged protein or peptide and an antimicrobial or membrane destabilizing peptide and one or more transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In another embodiment, a method of treatment comprises administering to a patient a therapeutically effective amount of a chimeric molecule comprising any two or more proteins, peptides or variants thereof, said proteins, peptides or variants thereof comprising: an antimicrobial or membrane destabilizing domain and one or more supercharged proteins or peptides, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In another embodiment, a method of treatment comprises administering to a patient a therapeutically effective amount of a chimeric molecule comprising an antimicrobial or membrane destabilizing domain, one or more supercharged proteins or peptides, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In another embodiment, a method of treatment comprises administering to a patient a therapeutically effective amount of a chimeric nucleic acid molecule encoding any two or more proteins, peptides or variants thereof, said proteins, peptides or variants thereof comprising: a supercharged protein or peptide, antimicrobial or membrane destabilizing domain, transcriptional activators, transcriptional repressors, recombinases, nucleases, DNA-binding proteins or nucleic acids, or combinations thereof. In embodiments, the gene editing agents comprise: Cre recombinases, CRISPR/Cas molecules, TALE transcriptional activators, Cas9 nucleases, nickases, transcriptional regulators or combinations thereof.

In other embodiments, the method of treating hearing loss or deafness using the liposomal formulation for complexing protein and nucleic acid embodied herein (e.g. transcription factors with their target binding region as oligonucleotides) for inner ear cell type delivery in vivo, comprises regeneration (e.g. hair cell and auditory neuron regeneration), repair (e.g. re-establishment of connections between hair cells and neurons for hearing recovery) and prevention.

Hearing Loss or Deafness and Associated Disorders:

One in 1000 newborns suffers from genetic deafness. Over 80 deafness genes have been identified, and additional 200-300 deafness genes remain to be discovered. Despite the tremendous progress, there is no treatment for any genetic deafness. Thus there are urgent needs to develop treatment that targets different types of genetic deafness.

There two main categories of genetic deafness: recessive deafness that is generally congenital; and dominant deafness that is mainly progressive. For recessive deafness, delivery and continuous expression of a normal copy of mutant gene could compensate for lost function for hearing recovery. Adeno-associated virus (AAV) based gene therapy has been the choice to be developed as treatment for recessive deafness, due to its long-term expression pattern and good safety record. AAV vectors however can only accommodate inserts less than 4.5 kb, whereas many deafness genes are much larger in size, thus severely limiting usefulness of AAV. For dominant deafness gene delivery will unlikely work.

Non-inherited abnormalities of the inner ear, such as the Mondini malformation, account for roughly 20% of congenital sensorineural deafness. The bulk of the remaining (genetic) deafness is non-syndromic, meaning that it does not have any obvious distinguishing features.

Most non-syndromic hearing losses are caused by connexin gene mutations. In the mammals, at least 20 connexin subtypes have been identified in mouse and human genomics. Connexin genes encode gap junctional channels, which connect two adjacent cells allowing passage of cytoplasmic ions and small molecules up to 1.2 kDa. In the mammalian inner ear, connexin26 (Cx26) and Cx30 are predominant isoforms. Cx26 mutation can induce a high incidence of hearing loss, responsible for 70 to 80 percent of nonsyndromic hearing loss in children.

Non-Syndromic Deafness:

Nonsyndromic means that deafness occurs in isolation, without other associated disorders. About 80% of genetic hearing loss is non-syndromic. Between 1992 and 2001, 38 loci for autosomal dominant non-syndromic deafness have been mapped and 11 genes have been identified. Autosomal dominant loci are called DFNA, autosomal recessive as DFNB, and X-linked as DFN.

Non-syndromic deafness is highly heterogeneous, but mutations in the connexin-26 molecule (gap junction protein, gene GJB2) account for about 49% of patients with non-syndromic deafness and about 37% of sporadic cases. About 1 in 31 individuals of European extraction are likely carriers.

Autosomal Dominant (DFNA):

Autosomal dominant deafness is passed directly through generations. It is often possible to identify an autosomal dominant pattern through simple inspection of the family tree. Examples of autosomal dominant deafness are missense mutation in COL11A2 (DFNA13) and in the TMC1 gene. COL11A2 encodes a chain of type XI collagen whereas TMC1 encodes a hair cell channel protein.

Autosomal Recessive (DFNB):

Autosomal recessive disorders require a gene from both the mother and father.

Syndromic Deafness:

Syndromic deafness, which accounts for the remaining 20% of congenital deafness, comprises an immensely complicated interlinked set of disorders. The descriptions here are only to give the general flavor of the diseases and are not meant to include all features of the disorders. In most cases, an Online Mendelian Inheritance in Man (OMIM) database link to the main type of the genetic disorder is provided. This database is a catalog of human genes and genetic disorders.

Alport Syndrome:

Alport syndrome is caused by mutations in COL4A3, COL4A4 or COL4A5. The classic phenotype is renal failure and progressive sensorineural deafness.

Branchio-Oto-Renal Syndrome:

Branchio-oto-renal syndrome is caused by mutations in EYA1, a gene of 16 exons within a genomic interval of 156 kB. This syndrome is characterized by hearing disturbances and cataract, branchial cleft fistulae, and preauricular pits. Mondini malformations and related dysplasias may occur.

X-Linked Charcot Marie Tooth (CMT):

The dominantly form of X-linked CMT is caused by a mutation in the connexin 32 gene mapped to the Xq13 locus. Usual clinical signs consist of a peripheral neuropathy combined with foot problems and "champagne bottle" calves.

As noted above, the connexin gene is also associated with a large percentage of cases of non-syndromic deafness. There are several other associated neuropathies and deafness syndromes. Autosomal recessive demyelinating neuropathy, autosomal dominant hereditary neuropathies type I and II, and X-linked hereditary axonal neuropathies with mental retardation are all associated with deafness.

Goldenhar's Syndrome:

Oculoauriculovertebral dysplasia (OAVD) or Goldenhar's syndrome was originally described in 1881. It includes a complex of features including hemifacial microtia, otomandibular dysostosis, epibulbar lipodermoids, coloboma, and vertebral anomalies that stem from developmental vascular and genetic field aberrations. It has diverse etiologies and is not attributed to a single genetic locus. The incidence is roughly 1 in 45,000.

Jervell and Lange-Nielsen Syndrome:

Jervell and Lange-Nielsen Syndrome is associated with cardiac arrhythmias. There is, by prolongation of the QT interval, torsade de Pointe arrhythmias (turning of the points, in reference to the apparent alternating positive and negative QRS complexes), sudden syncopal episodes, and severe to profound sensorineural hearing loss.

Mohr-Tranebjaerg Syndrome (DFN-1):

Mohr-Tranebjaerg syndrome (DFN-1) is an X-linked recessive syndromic hearing loss characterized by postlingual sensorineural deafness in childhood, followed by progressive dystonia, spasticity, dysphagia and optic atrophy. The syndrome is caused by a mutation thought to result in mitochondrial dysfunction. It resembles a spinocerebellar degeneration called Fredreich's ataxia which also may exhibit sensorineural hearing loss, ataxia and optic atrophy. The cardiomyopathy characteristic of Freidreich's ataxia is not seen in Mohr-Tranebjaerg syndrome.

Norrie Disease:

Classic features of Norrie Disease include specific ocular symptoms (pseudotumor of the retina, retinal hyperplasia, hypoplasia and necrosis of the inner layer of the retina, cataracts, phthisis bulbi), progressive sensorineural hearing loss, and mental disturbance, although less than one-half of patients are hearing impaired or mentally retarded.

Pendred Syndrome:

Pendred Syndrome is deafness associated with thyroid disease (goiter).

Stickler Syndrome:

Stickler syndrome is caused by mutations in COL11. It is characterized by hearing impairment, midface hypoplasia, progressive myopia in the first year of life, and arthropathy.

Treacher Collins Syndrome:

Treacher Collins syndrome (OMIM entry TCOF1) is characterized by coloboma of the lower eyelid (the upper eyelid is involved in Goldenhar syndrome), micrognathia, microtia, hypoplasia of the zygomatic arches, macrostomia, and inferior displacement of the lateral canthi with respect to the medial canthi.

Waardenburg Syndrome:

The clinical symptoms of Waardenburg Syndrome (WS) type I and II include lateral displacement of the inner canthus of each eye, pigmentary abnormalities of hair, iris, and skin (often white forelock and heterochromia iridis), and sensorineural deafness. The combination of WS type I characteristics with upper limb abnormalities has been called Klein-Waardenburg syndrome or WS type III. The combination of recessively inherited WS type II characteristics with Hirschsprung disease has been called Waardenburg-Shah syndrome or WS type IV.

Usher Syndrome:

Usher syndrome is characterized by hearing impairment and retinitis pigmentosa. Usher syndrome can be classified into three different types on the basis of clinical findings. In type I, there is both hearing impairment and vestibular impairment. In type II, there is hearing impairment without vestibular impairment. In type III, there are variable amounts of vestibular impairment.

Mitochondrial Disorders:

Hearing loss is common in mitochondrial disorders including MELAS (mitochondrial encephalomyopathy, lactic acidosis, and stroke like episodes), Kearns-Sayre syndrome and MERRF (myoclonic epilepsy with ragged red fibers). These disorders are caused by mutations in mitochondrial DNA, and are characterized by muscular weakness, an abnormal muscle biopsy with "ragged red" fibers, and a variety of other findings that define the specific clinical phenotype. In MELAS, it was reported that the hearing loss is caused by cochlear damage. It resembles presbyacusis in that it is generally symmetrical, gradual, and affects the higher frequencies first. Others have also reported hearing loss associated with mitochondrial mutations. Mitochondrial DNA mutations accumulate naturally during life and are presently implicated as an important cause of normal aging. Mitochondrial defects have been reported to cause both unusual sensitivity to aminoglycosides as well as non-syndromic sensorineural deafness.

Non-Inherited Congenital Deafness:

These types of abnormalities account for roughly 20% of congenital deafness, the remainder being genetic in origin.

Mondini Dysplasia:

The normal cochlea has two and one-half turns. A cochlear malformation consists of a membranous abnormality, a bony abnormality, or a combination of these two. If cochlear development is arrested in the embryo, a common cavity may occur instead of the snail like cochlea. This is called the Mondini dysplasia or malformation.

Often accompanying the Mondini dysplasia is abnormal communication between the endolymphatic and perilymphatic spaces of the inner ear and subarachnoid space. It is usually caused by a defect in the cribiform area of the lateral end of the internal auditory canal, presumably because of this abnormal channel, perilymphatic fistulae are more common in this disorder.

A related anomaly and more severe syndrome, the CHARGE association, consists of coloboma, heart disease, choanal atresia, retarded development, genital hypoplasia, ear anomalies including hypoplasia of the external ear and hearing loss. These individuals have a Mondini type deformity and absence of semicircular canals.

Enlarged Vestibular Aqueduct Syndrome:

Enlarged Vestibular Aqueduct Syndrome is defined on the CT scan as a diameter greater than or equal to 1.5 mm measured midway between the operculum and the common crus.

Recently CRISPR (Clustered Regularly Interspaced Short Palindromic Repeats) endonuclease gene editing has been developed with potential to revolutionize genetic therapy. CRISPR uses Cas9 and guide RNA to target any genomic sequence for specific cleavage, resulting disruption or repair of any gene. The process applies to mutant genes regardless the nature of mutations (recessive or dominant), with permanent correction to restore normal gene function.

Conventional approaches with CRSIP involve the use of viral vehicle to deliver Cas9 and guide RNAs (sgRNA, a template homologous to the target genomic region of 20-29 bp) to cells for gene editing. However the viral genome will remain permanently inside cells (for inner ear it means the whole life) with uncertain consequences (e.g. immunogenic response, potential recombination). In addition the efficiency of CRISPR mediated targeted cleavage in vivo has been relatively low (less than 5%).

A major improvement over previous methods is to directly deliver protein and nucleic acid complex into cells for the CRISPR mediated gene editing. This approach would allow transient delivery of proteins and nucleic acids, which will be degraded after their function, thus limiting possible adverse effect due to long-term presence of both in cells. Delivery of the combination of proteins with nucleic acids has not been achieved in vivo or in vitro.

Nucleic acid deliveries based on cationic lipid formulations have been used widely with high efficiency. The lipid bilayer of liposome protects the encapsulated nucleic acids from degradation and can prevent neutralization by antibodies. Significantly, fusion of liposomes with the endosomal membrane during endosome maturation can enable the efficient endosomal escape of cationic lipid-delivered cargo. As some natural proteins or proteins with modifications can be highly negative (anionic), it is possible to use liposomes based vehicles to deliver proteins into cells directly with high efficiency. It is further possible to combine the delivery of anionic proteins and nucleic acids (which is anionic) together with liposomes.

Accordingly, in some embodiments, a method of treating deafness associated with a genetic mutation in a patient in need thereof, comprises administering to the patient a therapeutically effective amount of a chimeric molecule comprising at least one protein or peptide fused, complexed or linked to one or more anionic molecules. The chimeric molecule targets one or more genetic loci associated with deafness in a patient and modulates replication, expression, function or activity of the genetic locus. The genotypic variations that can confer abnormal phenotypes, e.g. deafness, comprise: mutations, insertions, deletions, substitutions or combinations thereof wherein the abnormal gene is expressed. In embodiments, the chimeric molecule comprises one or more gene editing agents for repression of the genetic locus associated with deafness in a patient. These gene editing agents comprise: transcriptional activators, transcriptional repressors, recombinases, nucleases, DNA-binding proteins or nucleic acids, or combinations thereof.

In embodiments, the anionic molecules comprise: oligonucleotides, polynucleotides, proteins, peptides, peptide nucleic acids (PNA), synthetic molecules or combinations thereof. Examples of oligonucleotides or polynucleotides include: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof.

In embodiments, the chimeric molecule is encapsulated in a cationic liposome and is administered to a patient's inner ear.

In another embodiment, a method of treating a patient suffering from deafness due to a genetic mutation comprises: administering to a patient's inner ear, a cationic liposome encapsulating a therapeutically effective amount of an anionic molecule comprising a protein or peptide complexed, fused or linked to a negatively charged molecule. In these embodiments, the chimeric molecule targets one or more genetic loci associated with deafness in a patient and modulates replication, expression, function or activity of the genetic locus. These genetic loci associated with deafness comprise: mutations, insertions, deletions, substitutions or combinations thereof. The anionic molecule comprises one or more gene editing agents for repression of a genetic locus associated with deafness in a patient. Examples of these gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

Non-exhaustive examples of mutations in genes that cause, for example, nonsyndromic deafness, include, without limitation, mutations in the ACTG1, CDH23, CLDN14, COCH, COL11A2, DFNA5, ESPN, EYA4, GJB2, GJB6, GRXCR1, KCNQ4, MYO3A, MYO15A, MYO6, MYO7A, OTOF, OTOA, PCDH15, POU3F4, RDX, SLC26A4, STRC, TECTA, TMC1, TMIE, TMPRSS3, USH1C, WFS1 and WHRN genes cause nonsyndromic deafness, with weaker evidence currently implicating genes CCDC50, DIAPH1, DSPP, ESRRB, GJB3, GRHL2, GRXCR1, HGF, LHFPL5, LOXHD1, LRTOMT, MARVELD2, MIR96, MYH14, MYH9, MYO1A, MYO3A, OTOA, PJVK, POU4F3, PRPS1, PTPRQ, RDX, SERPINB6, SIX1, SLC17A8, TPRN, TRIOBP, and WHRN.

Accordingly, any one or more genes or genetic loci associated with deafness can be targeted. In other embodiments, the molecules embodied herein are administered to treat patients suffering from diseases or disorders associated with deafness. Examples of these diseases or disorders include: tinnitus, hyperscusis, ADHD.

In some embodiments, the gene editing agents comprise: Cre recombinases, CRISPR/Cas molecules, TALE transcriptional activators, Cas9 nucleases, nickases, transcriptional regulators or combinations thereof.

In other embodiments, the anionic molecule comprises any one or more sequences having a sequence identity of at least about 75% to sequences set forth as SEQ ID NOS: 1 to 95. In another embodiment, the anionic molecule comprises one or more antimicrobial or membrane destabilizing domains.

In another embodiment, the one or more sequences are set forth as SEQ ID NOS: 1 to 95. In another embodiment, the one or more sequences comprise SEQ ID NOS: 1 to 95 linked, fused, complexed with one or more antimicrobial or membrane destabilizing domains.

In other embodiments, the chimeric molecules or the encapsulated chimeric or anionic molecules are administered in a pharmaceutical composition.

Pharmaceutical Compositions:

The types and amounts of chimeric molecules for use as therapeutic compounds may be believed to have therapeutic activity on the basis of any information available to the artisan. For example, a prototype compound may be believed to have therapeutic activity on the basis of information contained in the Physician's Desk Reference. In addition, by way of non-limiting example, a therapeutic compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases.

A therapeutically-active compound is a compound that has therapeutic activity, including for example, the ability of a compound to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder that would benefit from dissociation of a tissue or mass of cells, for example. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

In some embodiments, a pharmaceutical composition comprises a cationic lipid encapsulating a chimeric molecule embodied herein. In other embodiments, the molecule comprises one or more sequences set forth as SEQ ID NOS: 1 to 95. In another embodiment, the one or more sequences comprise SEQ ID NOS: 1 to 95 linked, fused, complexed with one or more antimicrobial or membrane destabilizing domains.

Formulations, Administration:

The compositions embodied herein, are formulated for administration by any suitable method, for example, as described in Remington: The Science And Practice Of Pharmacy (21st ed., Lippincott Williams & Wilkins). Exemplary routes of administration include, but are not limited to parenteral, oral, subcutaneous, topical, intramuscular, transdermal, transmucosal, sublingual, intranasal, transvascular, subcutaneous, orbital, or combinations thereof.

Kits: In yet another aspect, the invention provides kits for targeting nucleic acid sequences of cells and molecules associated with modulation of the target molecule. For example, the kits can be used to target any desired nucleic sequence and as such, have many applications.

In one embodiment, a kit comprises: (a) a cationic lipid, and a chimeric molecule or an encapsulated chimeric molecule, or a protein and a separate polyanionic molecule, or any combinations thereof, and (b) instructions to administer to cells or an individual a therapeutically effective amount of the composition. In some embodiments, the kit may comprise pharmaceutically acceptable salts or solutions for administering the composition. Optionally, the kit can further comprise instructions for suitable operational parameters in the form of a label or a separate insert. For example, the kit may have standard instructions informing a physician or laboratory technician to prepare a dose of chimeric molecule.

Optionally, the kit may further comprise a standard or control information so that a patient sample can be compared with the control information standard to determine if the test amount of chimeric molecule is a therapeutic amount consistent with for example, treating deafness in a patient.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Efficient Delivery of Genome Editing Proteins In Vitro and In Vivo

Construction of Cas9, Cre, and TALE Fusion and sgRNA Expression Plasmids.

Sequences of all constructs used are listed below. All protein constructs were generated from previously reported plasmids for protein of interest cloned into a pET29a expression plasmid.

Expression and Purification of S. pyogenes Cas9 and Other Proteins.

E. coli BL21 STAR (DE3) competent cells (Life Technologies) were transformed with pMJ806 (Pattanayak, V. et al. Nat. Biotechnol. 31, 839-843 (2013)) encoding the S. pyogenes Cas9 fused to an N-terminal 10×His-tag (SEQ ID NO: 97)/maltose binding protein. The resulting expression strain was inoculated in Luria-Bertani (LB) broth containing 100 μg/mL of ampicillin at 37° C. overnight. The cells were diluted 1:100 into the same growth medium and grown at 37° C. to $OD_{600}$=~0.6. The culture was incubated at 20° C. for 30 min, and isopropyl β-D-1-thiogalactopyranoside (IPTG) was added at 0.5 mM to induce Cas9 expression. After ~16 h, the cells were collected by centrifugation at 8,000 g and resuspended in lysis buffer (50 mM tris(hydroxymethyl)-aminomethane (Tris)-HCl, pH 8.0, 1 M NaCl, 20% glycerol, 10 mM tris(2-carboxyethyl)phosphine (TCEP)). The cells were lysed by sonication (1 sec pulse-on, 1 sec pulse-off for 15 min total at 6 W output) and the soluble lysate was obtained by centrifugation at 20,000 g for 30 min.

The cell lysate was incubated with His-Pur nickel-nitrilo-acetic acid (nickel-NTA) resin (Thermo Scientific) at 4° C. for 30 min to capture His-tagged Cas9. The resin was transferred to a 20-mL column and washed with 20 column volumes of lysis buffer. Cas9 was eluted in 50 mM Tris-HCl (pH 8), 0.1 M NaCl, 20% glycerol, 10 mM TCEP, and 300 mM imidazole, and concentrated by Amicon ultra centrifugal filter (Millipore, 100-kDa molecular weight cut-off) to ~50 mg/mL. The 6×His tag (SEQ ID NO: 98) and maltose-binding protein were removed by TEV protease treatment at 4° C. for 20 hours and captured by a second Ni-affinity purification step. The eluent, containing Cas9, was injected into a HiTrap SP HP column (GE Healthcare) in purification buffer containing 50 mM Tris-HCl (pH 8), 0.1 M NaCl, 20% glycerol, and 10 mM TCEP. Cas9 was eluted with purification buffer containing a linear NaCl gradient from 0.1 M to 1 M over five column volumes. The eluted fractions containing Cas9 were concentrated down to a concentration of 200 μM as quantified by bicinchoninic acid assay (BCA) (Pierce Biotechnology), snap-frozen in liquid nitrogen, and stored in aliquots at −80° C. All other proteins were purified by this method but without TEV cleavage step and proteins containing (−30) GFP were purified by anion exchange using a Hi-Trap Q HP anion exchange column (GE Healthcare) using the same purification protocol.

In Vitro Transcription of sgRNAs.

Linear DNA fragments containing the T7 promoter binding site followed by the 20-bp sgRNA target sequence were transcribed in vitro using the T7 High Yield RNA Synthesis Kit (NEB) according to the manufacturer's instructions. In vitro transcribed RNA was precipitated with ethanol and purified by gel electrophoresis on a Criterion 10% polyacrylamide TBE-Urea gel (Bio-Rad). Excised gel fragments were extracted in 420 μL of 300 mM NaCl overnight on a rocking surface at 4° C. Gel-purified sgRNA was precipitated with ethanol and redissolved in water and sgRNA concentration was finally quantified by UV absorbance and snap-frozen at −80° C.

Plasmid Transfection.

Plasmid DNA was transfected using Lipofectamine 2000 (Life Technologies) according the manufacturer's protocol. For TALE activator plasmids, 300 ng of DNA was transfected, and for the activator synergy experiments 60 ng of each of five plasmids was pooled and transfected. For Cas9 nuclease delivery experiments, linear DNA PCR products expressing sgRNAs were used in transfection experiments targeting genomic sites in CLTA, EMX, VEGF, and GFP (sgRNA GFP g1, GFP g3, GFP g5, and GFP g7 for nickase studies). Linear DNA PCR products were generated using plasmid containing the U6 promoter as template and forward primers bearing the U6 promoter upstream sequence and reverse primers containing U6 downstream sequence followed by the sgRNA sequence (20-bp sequence unique to each target plus constant sgRNA backbone architecture sequence). sgRNAs expressed from linear DNA templates contained at least two 5' guanosines to match in vitro transcribed sgRNAs that required these bases for T7 transcription. Primer sequences and PCR conditions are referred to herein. For dCas9 activator experiments, 700 ng of Cas9 or dCas9-VP64 plasmid DNA was co-transfected with 250 ng of the appropriate sgRNA expression plasmid. For activator synergy experiments 50 ng of DNA from each of the six sgRNA was pooled and co-transfected with 700 ng of dCas9-VP64 plasmid.

Delivery of Transcription Factor Proteins Complexed with Cationic Lipids in Cell Culture.

Briefly, cultured cells were plated in 48-well format (250 μL volume) in Dulbecco's Modified Eagle's Media plus GLUTAMAX (Life Technologies, Carlsbad, Calif.) with 10% FBS ("full serum media") and antibiotics at a cell density necessary to reach ~70% confluence the next day. Full serum media was replaced with the same media but containing no antibiotics at least one hour before delivery. Delivery of Cre and TALE proteins was performed by combining 1 nM to 1 μM protein (in 275 μL final volume) with 0.5-1.5 μL of commercially available cationic lipids in 25 μL OPTIMEM media (Life Technologies, Carlsbad, Calif.) according to the manufacturer's protocol for normal plasmid transfection, including incubation time. For Cas9 delivery in vitro, transcribed sgRNA was incubated with Cas9 protein for 5 min before complexing with the cationic lipid reagent. 25 μL lipid complexes in OPTIMEM media were added to cells and media was replaced 12-16 hours later fresh media unless otherwise noted. Cells were assayed for recombination 48 hours after delivery, for gene activation either 4 or 16 hours after delivery, and for gene modification 48 hours after delivery.

T7 Endonuclease I Assay to Detect Genomic Modifications.

U2OS-EGFP cells or HEK293T cells were transfected with Cas9 expression and sgRNA expression plasmids or linear DNA PCR products as described above or treated with only Cas9 protein, only in vitro transcribed sgRNA, or only RNAiMAX. Genomic DNA was isolated from cells 2 days after transfection using the DNAdvance Kit (Agencourt) following the manufacturer's instructions. 200 ng of genomic DNA was used as template in PCR reactions to amplify the targeted genomic loci with flanking survey primer pairs specified herein. PCR products were purified with a QIAquick PCR Purification Kit (Qiagen) and quantified with QUANT-IT™ PICOGREEN® dsDNA Kit (Life Technologies). 250 ng of purified PCR DNA was combined with 2 µL of NEBuffer 2 (NEB) in a total volume of 19 µL and denatured then re-annealed with thermocycling at 95° C. for 5 min, 95 to 85° C. at 2° C./s; 85 to 20° C. at 0.2° C./s. The re-annealed DNA was incubated with 1 µl of T7 Endonuclease I (10 U/µl, NEB) at 37° C. for 15 min. 10 µL of 50% glycerol was added to the T7 Endonuclease reaction and 12 µL was analyzed on a 5% TBE 18-well Criterion PAGE gel (Bio-Rad) electrophoresed for 30 min at 200 V, then stained with 1×SYBR Gold (Life Technologies) for 30 min. Cas9-induced cleavage bands and the uncleaved band were visualized on an AlphaImager HP (Alpha Innotech) and quantified using ImageJ software (Schneider, C. A., et al. *Nat. Methods* 9, 671-675 (2012)). The peak intensities of the cleaved bands were divided by the total intensity of all bands (uncleaved+cleaved bands) to determine the fraction cleaved which was used to estimate gene modification levels as previously described (Guilinger, J. P., et al., *Nat. Biotechnol.* 32, 577-582 (2014)). For each sample, transfections and subsequent modification measurements were performed in triplicate on different days.

Stem Cell Culture and Delivery.

Mouse embryonic stem cell (ES) line Tau-GFP (courtesy of Dr. A. Edge, Massachusetts Eye & Ear Infirmary, Boston) containing a permanent GFP gene insertion was cultured in DMEM with 10% FBS (Gibco), 100 mM MEM nonessential amino acids (Gibco), 0.55 mM 2-mercaptoethanol, and leukemia inhibitory factor (1,000 units/ml; Chemicon). After 3 days floating spheres were formed that exhibited GFP fluorescence. Complexes of Cas9:sgRNA and Lipofectamine 2000 were added to the culture containing the floating spheres for 16 hours. After Cas9:sgRNA treatment, the cells were cultured in the above media for 3 days. The floating spheres were treated with trypsin for 5 min then passed through a 70 µm filter to collect single cells. The cells were cultured on laminin-coated slides in DMEM/F12 (1:1) supplemented with 1×N2, 1×B27, penicillin-streptomycin (100 µg/mL) and 10% FBS for two days before labeling. Immunohistochemistry was performed using an anti-GFP antibody (#ab13970, Abcam) to assess GFP expression. To quantify the number of GFP-negative cells, the total number of GFP-positive and GFP-negative cells from three representative visual fields at 20× magnification were counted, and the average efficiency was calculated. Three independent experiments were performed for each condition.

Microinjection of Proteins to Mouse Inner Ear.

P1 floxP-tdTomato mice (The Jackson Laboratory) were used for (−30)GFP-Cre injection and P2 Atoh1-GFP mice (Dr. J Johnson, Southwestern Medical Center, University of Texas) were used for Cas9:sgRNA injection. Animals were used under protocols approved by the Massachusetts Eye & Ear Infirmary ALCUC committee. Mice were anesthetized by lowering their temperature on ice. Cochleostomies were performed by making an incision behind the ear to expose the cochlea. Glass micropipettes held by a micromanipulator were used to deliver the complex into the scala media, which allows access to inner ear hair cells. For delivery of (−30) GFP-Cre, 3 µL of 45 µM protein was mixed with 3 µL of either RNAiMAX or Lipofectamine 2000 and incubated at room temperature for 30 minutes prior to injection. Four mice were injected per treatment group. For delivery of Cas9:sgRNA complexes, 1 µL of 200 µM Cas9 protein was mixed with 2 µL of 100 µM sgRNA and incubated for 5 minutes at room temperature before mixing with 3 µL of either RNAiMAX or Lipofectamine 2000 and incubating for an additional 30 minutes prior to injection. Three mice were injected per treatment group. The total delivery volume for every injection was 0.3 µL per cochlea and the release was controlled by a micromanipulator at the speed of 32 nL/sec.

Immunohistochemistry and Quantification.

5-10 days after injection, the mice were sacrificed and cochlea were harvested by standard protocols. For immunohistochemistry, antibodies against hair-cell markers (Myo7a and Esp) and supporting cells (Sox2) were used following a previously described protocol (Sage, C. et al. *Science* 307, 1114-1118 (2005)). To quantify the number of tdTomato positive cells after (−30)GFP-Cre or GFP negative cells after Cas9:sgRNA delivery, the total number of outer hair cells were counted in a region spanning 200 µm around the site of injection in the base turn of the cochlea. The efficiency of (−30)GFP-Cre-induced recombination or Cas9:sgRNA-induced genome modification was calculated as the percentage of outer hair cells that expressed tdTomato or that lost GFP expression.

High-Throughput DNA Sequencing of Genome Modifications.

HEK293T cells were either transfected with Cas9 and sgRNA expression plasmids or linear DNA PCR products or treated with 50 nM Cas9 protein, 250 nM purified sgRNA, and cationic lipids as described earlier for Cas9 protein delivery to U2OS-EGFP reporter cells. For plasmid-based transfection experiments, 700 ng of Cas9 expression plasmid plus 250 ng of sgRNA plasmid or 50 ng of a linear DNA PCR product expressing sgRNA for targeting either the EMX1, CLTA2, or VEGF locus were transfected with Lipofectamine 2000 (Life Technologies) and cells were isolated 2 days later. For protein delivery experiments in vivo, ~30 mg of mouse tissue was isolated from anesthetized mice and genomic DNA was extracted using the Agencourt DNAAdvance Genomic DNA Isolation Kit (Beckman Coulter). For cell culture experiments genomic DNA was isolated as described above. 150 ng of genomic DNA was used as template to amplify by PCR the on-target and off-target genomic sites with flanking HTS primer pairs specified herein. Relative amounts of crude PCR products were quantified by gel electrophoresis and samples treated with different sgRNA pairs or Cas9 nuclease types were separately pooled in equimolar concentrations before purification with the QIAquick PCR Purification Kit (Qiagen). ~150 ng of pooled DNA was electrophoresed using a 5% TBE 18-well Criterion PAGE gel (BioRad) for 30 min at 200 V and DNAs ~125 bp to ~300 bp in length were isolated and purified by QIAquick PCR Purification Kit (Qiagen). Purified DNA was amplified by PCR with primers containing sequencing adapters, purified, and sequenced on a MiSeq high-throughput DNA sequencer (Illumina) as previously described (Pattanayak, V. et al. *Nat. Biotechnol.* 31, 839-843 (2013)).

Quantification of Cas9 Protein Uptake.

Alexa Fluor 647 C2 Maleimide (Life Technologies, Carlsbad Calif.) was used to fluorescently label Cas9 protein on surface cysteines. A 10 mM stock solution of Alexa647 was prepared in anhydrous DMSO. In a 0.4 mL reaction, 10 nmol of purified Cas9 protein and 200 nmol of Alexa647 maleimide were combined in buffer conditions used for Cas9 protein storage. The labeling reaction was incubated at 4° C. for 16 hours. At the end of the reaction, excess unconjugated Alexa647 was removed by re-purifying the labeled Cas9 protein by cation exchange chromatography as described above. To measure the amount of protein delivered into treated cells, 20,000 cells were plated in the wells of a 48-well plate 1 day prior to treatment. On the day of treatment, 50 nM of Alexa647-labeled Cas9 (Cas9-Alexa647) and 100 nM of EGFP1 sgRNA were prepared for delivery using 0.8 µL of Lipofectamine 2000 as described above, and applied to the cells. After 4 hours, Cas9-Alexa647:sgRNA Lipofectamine-containing media was removed, and cells were washed three times with 500 µL of PBS containing 20 U/mL heparin.

The cells were trypsinized and prepared for counting and flow cytometry as described above. Cas9-Alexa647 uptake was measured by flow cytometry, while 10,000 cells of the treated population were transferred to a black, flat-bottomed, opaque 96-well plate. Standard curves of Cas9-Alexa647 were prepared by complexing 50 pmol of the Cas9-Alexa647 protein with Lipofectamine 2000 exactly as described for Cas9-Alexa647 delivery, followed by serial 2-fold dilutions in DMEM with 10% FBS containing 10,000 U2OS cells per well in the 96-well plate. The effect of U2OS cells or complexation with Lipofectamine 2000 on Alexa647 fluorescence was determined by preparing three additional Cas9-Alexa647 standard curves: (i) with Lipofectamine 2000 in media lacking U2OS cells, (ii) without Lipofectamine 2000 in media containing U2OS cells, and (iii) without Lipofectamine 2000 in media lacking U2OS cells.

Data Analysis.

Illumina sequencing reads were filtered and parsed with scripts written in Unix Bash. DNA sequences will be deposited in NCBI's Sequencing Reads Archive (SRA) and source code can be found in Supplementary Software. Sample sizes for sequencing experiments were maximized (within practical experimental considerations) to ensure greatest power to detect effects. Statistical analyses for Cas9-modified genomic sites (Table 2) were performed as previously described (Sander, J. D. et al. *Nucleic Acids Res.* 41, e181 (2013)).

Amino acid sequences of proteins used in this study

```
(+36)GFP-Cre-6xHis (SEQ ID NO: 1):
MGASKGERLFRGKVPILVELKGDVNGHKFSVRGKGKGDATRGKLTLKFICTTGKLPVP

WPTLVTTLTYGVQCFSRYPKHMKRHDFFKSAMPKGYVQERTISFKKDGKYKTRAEVKF

EGRTLVNRIKLKGRDFKEKGNILGHKLRYNFNSHKVYITADKRKNGIKAKFKIRHNVKD

GSVQLADHYQQNTPIGRGPVLLPRNHYLSTRSKLSKDPKEKRDHMVLLEFVTAAGIKHG

RDERYKTGGSGGSGGSGGSGGSGGSGGSGGSGGTASNLLTVHQNLPALPVDATSDEVR

KNLMDMFRDRQAFSEHTWKMLLSVCRSWAAWCKLNNRKWFPAEPEDVRDYLLYLQA

RGLAVKTIQQHLGQLNMLHRRSGLPRPSDSNAVSLVMRRIRKENVDAGERAKQALAFE

RTDFDQVRSLMENSDRCQDIRNLAFLGIAYNTLLRIAEIARIRVKDISRTDGGRMLIHIGR

TKTLVSTAGVEKALSLGVTKLVERWISVSGVADDPNNYLFCRVRKNGVAAPSATSQLS

TRALEGIFEATHRLIYGAKDDSGQRYLAWSGHSARVGAARDMARAGVSIPEIMQAGGW

TNVNIVMNYIRNLDSETGAMVRLLEDGDGGSHHHHHH (-7)GFP-Cre-6xHis (SEQ ID NO: 2):
MGASKGEELFTGVVPILVELDGDVNGHKFSVRGEGEGDATNGKLTLKFICTTGKLPVPW

PTLVTTLTYGVQCFSRYPDHMKQHDFFKSAMPEGYVQERTISFKDDGTYKTRAEVKFE

GDTLVNRIELKGIDFKEDGNILGHKLEYNFNSHNVYITADKQKNGIKANFKIRHNVEDGS

VQLADHYQQNTPIGDGPVLLPDNHYLSTQSALSKDPNEKRDHMVLLEFVTAAGITHGM

DELYKTGGSGGSGGSGGSGGSGGSGGSGGTASNLLTVHQNLPALPVDATSDEVRK

NLMDMFRDRQAFSEHTWKMLLSVCRSWAAWCKLNNRKWFPAEPEDVRDYLLYLQAR

GLAVKTIQQHLGQLNMLHRRSGLPRPSDSNAVSLVMRRIRKENVDAGERAKQALAFER

TDFDQVRSLMENSDRCQDIRNLAFLGIAYNTLLRIAEIARIRVKDISRTDGGRMLIHIGRT

KTLVSTAGVEKALSLGVTKLVERWISVSGVADDPNNYLFCRVRKNGVAAPSATSQLST

RALEGIFEATHRLIYGAKDDSGQRYLAWSGHSARVGAARDMARAGVSIPEIMQAGGWT

NVNIVMNYIRNLDSETGAMVRLLEDGDGGSHHHHHH (-20)GFP-Cre-6xHis (SEQ ID NO: 3):
MGASKGEELFTGVVPILVELDGDVNGHKFSVRGEGEGDATNGKLTLKFICTTGKLPVPW

PTLVTTLTYGVQCFSRYPDHMQHDFFKSAMPEGYVQERTISFKDDGTYKTRAEVKFE
```

-continued

GDTLVNRIELKGIDFKEDGNILGHKLEYNFNSHDVYITADKQENGIKAEFEIRHNVEDGS

VQLADHYQQNTPIGDGPVLLPDDHYLSTESALSKDPNEDRDHMVLLEFVTAAGIDHGM

DELYKTGGSGGSGGSGGSGGSGGSGGSGGTASNLLTVHQNLPALPVDATSDEVRK

NLMDMFRDRQAFSEHTWKMLLSVCRSWAAWCKLNNRKWFPAEPEDVRDYLLYLQAR

GLAVKTIQQHLGQLNMLHRRSGLPRPSDSNAVSLVMRRIRKENVDAGERAKQALAFER

TDFDQVRSLMENSDRCQDIRNLAFLGIAYNTLLRIAEIARIRVKDISRTDGGRMLIHIGRT

KTLVSTAGVEKALSLGVTKLVERWISVSGVADDPNNYLFCRVRKNGVAAPSATSQLST

RALEGIFEATHRLIYGAKDDSGQRYLAWSGHSARVGAARDMARAGVSIPEIMQAGGWT

NVNIVMNYIRNLDSETGAMVRLLEDGDGGSHHHHHH (-30)GFP-Cre-6xHis (SEQ ID NO: 4):
MGASKGEELFDGVVPILVELDGDVNGHEFSVRGEGEGDATEGELTLKFICTTGELPVPW

PTLVTTLTYGVQCFSDYPDHMDQHDFFKSAMPEGYVQERTISFKDDGTYKTRAEVKFE

GDTLVNRIELKGIDFKEDGNILGHKLEYNFNSHDVYITADKQENGIKAEFEIRHNVEDGS

VQLADHYQQNTPIGDGPVLLPDDHYLSTESALSKDPNEDRDHMVLLEFVTAAGIDHGM

DELYKTGGSGGSGGSGGSGGSGGSGGSGGTASNLLTVHQNLPALPVDATSDEVRK

NLMDMFRDRQAFSEHTWKMLLSVCRSWAAWCKLNNRKWFPAEPEDVRDYLLYLQAR

GLAVKTIQQHLGQLNMLHRRSGLPRPSDSNAVSLVMRRIRKENVDAGERAKQALAFER

TDFDQVRSLMENSDRCQDIRNLAFLGIAYNTLLRIAEIARIRVKDISRTDGGRMLIHIGRT

KTLVSTAGVEKALSLGVTKLVERWISVSGVADDPNNYLFCRVRKNGVAAPSATSQLST

RALEGIFEATHRLIYGAKDDSGQRYLAWSGHSARVGAARDMARAGVSIPEIMQAGGWT

NVNIVMNYIRNLDSETGAMVRLLEDGDGGSHHHHHH

Cre-6xHis (SEQ ID NO: 5):
MASNLLTVHQNLPALPVDATSDEVRKNLMDMFRDRQAFSEHTWKMLLSVCRSWAAW

CKLNNRKWFPAEPEDVRDYLLYLQARGLAVKTIQQHLGQLNMLHRRSGLPRPSDSNAV

SLVMRRIRKENVDAGERAKQALAFERTDFDQVRSLMENSDRCQDIRNLAFLGIAYNTLL

RIAEIARIRVKDISRTDGGRMLIHIGRTKTLVSTAGVEKALSLGVTKLVERWISVSGVAD

DPNNYLFCRVRKNGVAAPSATSQLSTRALEGIFEATHRLIYGAKDDSGQRYLAWSGHSA

RVGAARDMARAGVSIPEIMQAGGWTNVNIVMNYIRNLDSETGAMVRLLEDGDGGSHH

HHHH

Cas9 (SEQ ID NO: 6):
MDKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKNGY

AGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

-continued

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD

Cas9-6xHis (SEQ ID NO: 7):
MDKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKNGY

AGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGDHH

HHHH

NLS-Cas9-6xHis (SEQ ID NO: 8):
MPKKKRKVMDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHRLEESFLVEED

KKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLP

GEKKNGLFGNLIALSLGLTPNFKSNFDLAEDAKLQLSKDTYDDDLDNLLAQIGDQYADL

-continued

FLAAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNGSI

PHQIHLGELHAILRRQEDFYPFLKDNREKIEKILTFRIPYYVGPLARGNSRFAWMTRKSEE

TITPWNFEEVVDKGASAQSFIERMTNFDKNLPNEKVLPKHSLLYEYFTVYNELTKVKYV

TEGMRKPAFLSGEQKKAIVDLLFKTNRKVTVKQLKEDYFKKIECFDSVEISGVEDRFNA

SLGTYHDLLKIIKDKDFLDNEENEDILEDIVLTLTLFEDREMIEERLKTYAHLFDDKVMK

QLKRRRYTGWGRLSRKLINGIRDKQSGKTILDFLKSDGFANRNFMQLIHDDSLTFKEDIQ

KAQVSGQGDSLHEHIANLAGSPAIKKGILQTVKVVDELVKVMGRHKPENIVIEMARENQ

TTQKGQKNSRERMKRIEEGIKELGSQILKEHPVENTQLQNEKLYLYYLQNGRDMYVDQ

ELDINRLSDYDVDHIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKYP

KLESEFVYGDYKVYDVRKMIAKSEQEIGKATAKYFFYSNIMNFFKTEITLANGEIRKRPL

IETNGETGEIVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSSFEKNPIDF

LEAKGYKEVKKDLIIKLPKYSLFELENGRKRMLASAGELQKGNELALPSKYVNFLYLAS

HYEKLKGSPEDNEQKQLFVEQHKHYLDEIIEQISEFSKRVILADANLDKVLSAYNKHRD

KPIREQAENIIHLFTLTNLGAPAAFKYFDTTIDRKRYTSTKEVLDATLIHQSITGLYETRID

LSQLGGDHHHHHH

Cas9-NLS-6xHis (SEQ ID NO: 9):
MDKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKNGY

AGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLyETRIDLSQLGGDPK

KKRKVMDKHHHHHH (+36)dGFP-NLS-Cas9-6xHis (Y67S) (SEQ ID NO: 10):
MGASKGERLFRGKVPILVELKGDVNGHKFSVRGKGKGDATRGKLTLKFICTTGKLPVP

WPTLVTTLTSGVQCFSRYPKHMKRHDFFKSAMPKGYVQERTISFKKDGKYKTRAEVKF

EGRTLVNRIKLKGRDFKEKGNILGHKLRYNFNSHKVYITADKRKNGIKAKFKIRHNVKD

GSVQLADHYQQNTPIGRGPVLLPRNHYLSTRSKLSKDPKEKRDHMVLLEFVTAAGIKHG

RDERYKTGGSGGSGGSGGSGGSGGSGGSGGSGGTALALPKKKRKVMDKKYSIGLDIGT

NSVGWAVITDEYKVPSKKFKVLGNTDRHSIKKNLIGALLFDSGETAEATRLKRTARRRY

TRRKNRICYLQEIFSNEMAKVDDSFFHRLEESFLVEEDKKHERHPIFGNIVDEVAYHEKY

PTIYHLRKKLVDSTDKADLRLIYLALAHMIKFRGHFLIEGDLNPDNSDVDKLFIQLVQTY

NQLFEENPINASGVDAKAILSARLSKSRRLENLIAQLPGEKKNGLFGNLIALSLGLTPNFK

SNFDLAEDAKLQLSKDTYDDDLDNLLAQIGDQYADLFLAAKNLSDAILLSDILRVNTEIT

KAPLSASMIKRYDEHHQDLTLLKALVRQQLPEKYKEIFFDQSKNGYAGYIDGGASQEEF

YKFIKPILEKMDGTEELLVKLNREDLLRKQRTFDNGSIPHQIHLGELHAILRRQEDFYPFL

KDNREKIEKILTFRIPYYVGPLARGNSRFAWMTRKSEETITPWNFEEVVDKGASAQSFIE

RMTNFDKNLPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKIIKDKDFLDNEE

NEDILEDIVLTLTLFEDREMIEERLKTYAHLFDDKVMKQLKRRRYTGWGRLSRKLINGIR

DKQSGKTILDFLKSDGFANRNFMQLIHDDSLTFKEDIQKAQVSGQGDSLHEHIANLAGSP

AIKKGILQTVKVVDELVKVMGRHKPENIVIEMARENQTTQKGQKNSRERMKRIEEGIKE

LGSQILKEHPVENTQLQNEKLYLYYLQNGRDMYVDQELDINRLSDYDVDHIVPQSFLKD

DSIDNKVLTRSDKNRGKSDNVPSEEVVKKMKNYWRQLLNAKLITQRKFDNLTKAERGG

LSELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMIAKS

EQEIGKATAKYFFYSNIMNFFKTEITLANGEIRKRPLIETNGETGEIVWDKGRDFATVRK

VLSMPQVNIVKKTEVQTGGFSKESILPKRNSDKLIARKKDWDPKKYGGFDSPTVAYSVL

VVAKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQHK

HYLDEIIEQISEFSKRVILADANLDKVLSAYNKHRDKPIREQAENIIHLFTLTNLGAPAAFK

YFDTTIDRKRYTSTKEVLDATLIHQSITGLYETRIDLSQLGGDHHHHHH (-30)dGFP-NLS-Cas9-6xHis (Y67S) (SEQ ID NO: 11):
MGASKGEELFDGVVPILVELDGDVNGHEFSVRGEGEGDATEGELTLKFICTTGELPVPW

PTLVTTLTSGVQCFSDYPDHMDQHDFFKSAMPEGYVQERTISFKDDGTYKTRAEVKFEG

DTLVNRIELKGIDFKEDGNILGHKLEYNFNSHDVYITADKQENGIKAEFEIRHNVEDGSV

QLADHYQQNTPIGDGPVLLPDDHYLSTESALSKDPNEDRDHMVLLEFVTAAGIDHGMD

ELYKTGGSGGSGGSGGSGGSGGSGGSGGTALALPKKKRKVMDKKYSIGLDIGTNS

VGWAVITDEYKVPSKKFKVLGNTDRHSIKKNLIGALLFDSGETAEATRLKRTARRRYTR

RKNRICYLQEIFSNEMAKVDDSFFHRLEESFLVEEDKKHERHPIFGNIVDEVAYHEKYPTI

YHLRKKLVDSTDKADLRLIYLALAHMIKFRGHFLIEGDLNPDNSDVDKLFIQLVQTYNQ

-continued

LFEENPINASGVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDILRVNTEITKA

PLSASMIKRYDEHHQDLTLLKALVRQQLPEKYKEIFFDQSKNGYAGYIDGGASQEEFYK

FIKPILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFIERM

TNFDKNLPNEKVLPKHSLLYEYFTVYNELTKVKYVTEGMRKPAFLSGEQKKAIVDLLFK

TNRKVTVKQLKEDYFKKIECFDSVEISGVEDRFNASLGTYHDLLKIIKDKDFLDNEENED

ILEDIVLTLTLFEDREMIEERLKTYAHLFDDKVMKQLKRRRYTGWGRLSRKLINGIRDKQ

SGKTILDFLKSDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRIEEGIKELGS

QILKEHPVENTQLQNEKLYLYYLQNGRDMYVDQELDINRLSDYDVDHIVPQSFLKDDSI

DNKVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHKH

YLDEIIEQISEFSKRVILADANLDKVLSAYNKHRDKPIREQAENIIHLFTLTNLGAPAAFKY

FDTTIDRKRYTSTKEVLDATLIHQSITGLYETRIDLSQLGGDHHHHHH dCas9-VP64-6xHis (D10A and H840A) (SEQ ID NO: 12):
MDKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKNGY

AGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

-continued

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGDGS

PKKKRKVSSDYKDHDGDYKDHDIDYKDDDDKAAGGGGSGRADALDDFDLDMLGSDA

LDDFDLDMLGSDALDDFDLDMLGSDALDDFDLDMLHHHHHH

Cas9 nickase (D10A) (SEQ ID NO: 13):
MDKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKNGY

AGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGDHH

HHHH (-30)GFP-Cre-6xHis (SEQ ID NO: 14):
ATGGGTGCTAGCAAAGGTGAAGAGCTGTTTGACGGTGTAGTACCGATCTTAGTGGA

ATTAGACGGCGACGTGAACGGTCACGAATTTAGCGTGCGCGGCGAGGGCGAAGGTG

ACGCTACCGAGGGTGAATTGACCCTGAAGTTTATTTGCACAACAGGCGAATTACCCG

TTCCGTGGCCCACCTTAGTGACCACCCTGACCTATGGCGTTCAGTGCTTCAGTGATTA

CCCAGATCATATGGATCAACACGATTTTTTCAAATCAGCCATGCCTGAAGGATATGT

TCAAGAGCGTACAATCAGCTTCAAGGACGATGGCACCTATAAAACGCGTGCGGAAG

TGAAATTTGAAGGCGACACATTAGTAAACCGTATCGAACTGAAAGGTATCGACTTC

AAAGAAGACGGCAACATTTTAGGCCATAAGCTGGAATATAACTTTAATTCTCATGAC

GTGTATATTACGGCCGATAAACAGGAAAACGGTATCAAGGCAGAATTTGAAATTCG

CCATAACGTGGAGGACGGCAGCGTTCAATTAGCGGATCATTATCAACAAAACACGC

CGATTGGTGATGGGCCTGTACTGTTACCTGACGATCACTACCTGAGCACGGAGTCAG

-continued

```
CCCTGAGCAAAGATCCGAACGAAGACCGCGATCACATGGTTCTGTTAGAATTCGTG

ACCGCTGCAGGCATTGATCATGGAATGGACGAGCTGTACAAGACCGGTGGTAGCGG

TGGTTCTGGTGGTTCTGGTGGTAGCGGCGGTAGCGGTGGTAGCGGTGGTAGCGGTGG

CAGCGGCGGTACCGCGAGCAATTTACTGACCGTACACCAAAATTTGCCTGCATTGCC

GGTCGATGCAACGAGTGATGAGGTTCGCAAGAACCTGATGGACATGTTCAGGGATC

GCCAGGCGTTTTCTGAGCATACCTGGAAAATGCTTCTGTCCGTTTGCCGGTCGTGGG

CGGCATGGTGCAAGTTGAATAACCGGAAATGGTTTCCCGCAGAACCTGAAGATGTT

CGCGATTATCTTCTATATCTTCAGGCGCGCGGTCTGGCAGTAAAAACTATCCAGCAA

CATTTGGGCCAGCTAAACATGCTTCATCGTCGGTCCGGGCTGCCACGACCAAGTGAC

AGCAATGCTGTTTCACTGGTTATGCGGCGTATCCGAAAAGAAAACGTTGATGCCGGT

GAACGTGCAAAACAGGCTCTAGCGTTCGAACGCACTGATTTCGACCAGGTTCGTTCA

CTCATGGAAAATAGCGATCGCTGCCAGGATATACGTAATCTGGCATTTCTGGGGATT

GCTTATAACACCCTGTTACGTATAGCCGAAATTGCCAGGATCAGGGTTAAAGATATC

TCACGTACTGACGGTGGGAGAATGTTAATCCATATTGGCAGAACGAAAACGCTGGT

TAGCACCGCAGGTGTAGAGAAGGCACTTAGCCTGGGGGTAACTAAACTGGTCGAGC

GATGGATTTCCGTCTCTGGTGTAGCTGATGATCCGAATAACTACCTGTTTTGCCGGGT

CAGAAAAAATGGTGTTGCCGCGCCATCTGCCACCAGCCAGCTATCAACTCGCGCCCT

GGAAGGGATTTTTGAAGCAACTCATCGATTGATTTACGGCGCTAAGGATGACTCTGG

TCAGAGATACCTGGCCTGGTCTGGACACAGTGCCCGTGTCGGAGCCGCGCGAGATA

TGGCCCGCGCTGGAGTTTCAATACCGGAGATCATGCAAGCTGGTGGCTGGACCAAT

GTAAATATTGTCATGAACTATATCCGTAACCTGGATAGTGAAACAGGGGCAATGGT

GCGCCTGCTGGAAGATGGCGACGGCGGATCCCATCACCACCACCATCAC

Cre-6xHis (SEQ ID NO: 15):
ATGGCGAGCAATTTACTGACCGTACACCAAAATTTGCCTGCATTGCCGGTCGATGCA

ACGAGTGATGAGGTTCGCAAGAACCTGATGGACATGTTCAGGGATCGCCAGGCGTT

TTCTGAGCATACCTGGAAAATGCTTCTGTCCGTTTGCCGGTCGTGGGCGGCATGGTG

CAAGTTGAATAACCGGAAATGGTTTCCCGCAGAACCTGAAGATGTTCGCGATTATCT

TCTATATCTTCAGGCGCGCGGTCTGGCAGTAAAAACTATCCAGCAACATTTGGGCCA

GCTAAACATGCTTCATCGTCGGTCCGGGCTGCCACGACCAAGTGACAGCAATGCTGT

TTCACTGGTTATGCGGCGTATCCGAAAAGAAAACGTTGATGCCGGTGAACGTGCAA

AACAGGCTCTAGCGTTCGAACGCACTGATTTCGACCAGGTTCGTTCACTCATGGAAA

ATAGCGATCGCTGCCAGGATATACGTAATCTGGCATTTCTGGGGATTGCTTATAACA

CCCTGTTACGTATAGCCGAAATTGCCAGGATCAGGGTTAAAGATATCTCACGTACTG

ACGGTGGGAGAATGTTAATCCATATTGGCAGAACGAAAACGCTGGTTAGCACCGCA

GGTGTAGAGAAGGCACTTAGCCTGGGGGTAACTAAACTGGTCGAGCGATGGATTTC

CGTCTCTGGTGTAGCTGATGATCCGAATAACTACCTGTTTTGCCGGGTCAGAAAAAA

TGGTGTTGCCGCGCCATCTGCCACCAGCCAGCTATCAACTCGCGCCCTGGAAGGGAT

TTTTGAAGCAACTCATCGATTGATTTACGGCGCTAAGGATGACTCTGGTCAGAGATA

CCTGGCCTGGTCTGGACACAGTGCCCGTGTCGGAGCCGCGCGAGATATGGCCCGCG
```

```
CTGGAGTTTCAATACCGGAGATCATGCAAGCTGGTGGCTGGACCAATGTAAATATTG

TCATGAACTATATCCGTAACCTGGATAGTGAAACAGGGGCAATGGTGCGCCTGCTG

GAAGATGGCGACGGCGGATCCCATCACCACCACCATCAC (-30)dGFP-NLS-Cas9-6xHis (SEQ ID NO: 16):
ATGGGTGCTAGCAAAGGTGAAGAGCTGTTTGACGGTGTAGTACCGATCTTAGTGGA

ATTAGACGGCGACGTGAACGGTCACGAATTTAGCGTGCGCGGCGAGGGCGAAGGTG

ACGCTACCGAGGGTGAATTGACCCTGAAGTTTATTTGCACAACAGGCGAATTACCCG

TTCCGTGGCCCACCTTAGTGACCACCCTGACCTATGGCGTTCAGTGCTTCAGTGATTA

CCCAGATCATATGGATCAACACGATTTTTTCAAATCAGCCATGCCTGAAGGATATGT

TCAAGAGCGTACAATCAGCTTCAAGGACGATGGCACCTATAAAACGCGTGCGGAAG

TGAAATTTGAAGGCGACACATTAGTAAACCGTATCGAACTGAAAGGTATCGACTTC

AAAGAAGACGGCAACATTTTAGGCCATAAGCTGGAATATAACTTTAATTCTCATGAC

GTGTATATTACGGCCGATAAACAGGAAAACGGTATCAAGGCAGAATTTGAAATTCG

CCATAACGTGGAGGACGGCAGCGTTCAATTAGCGGATCATTATCAACAAAACACGC

CGATTGGTGATGGGCCTGTACTGTTACCTGACGATCACTACCTGAGCACGGAGTCAG

CCCTGAGCAAAGATCCGAACGAAGACCGCGATCACATGGTTCTGTTAGAATTCGTG

ACCGCTGCAGGCATTGATCATGGAATGGACGAGCTGTACAAGACCGGTGGTAGCGG

TGGTTCTGGTGGTTCTGGTGGTAGCGGCGGTAGCGGTGGTAGCGGTGGTAGCGGTGG

CAGCGGCGGTACCGCGCTCGCGCTGCCCAAGAAGAAGAGGAAGGTGATGGATAAG

AAATACTCAATAGGCTTAGATATCGGCACAAATAGCGTCGGATGGGCGGTGATCAC

TGATGAATATAAGGTTCCGTCTAAAAAGTTCAAGGTTCTGGGAAATACAGACCGCC

ACAGTATCAAAAAAAATCTTATAGGGGCTCTTTTATTTGACAGTGGAGAGACAGCG

GAAGCGACTCGTCTCAAACGGACAGCTCGTAGAAGGTATACACGTCGGAAGAATCG

TATTTGTTATCTACAGGAGATTTTTTCAAATGAGATGGCGAAAGTAGATGATAGTTT

CTTTCATCGACTTGAAGAGTCTTTTTTGGTGGAAGAAGACAAGAAGCATGAACGTCA

TCCTATTTTTGGAAATATAGTAGATGAAGTTGCTTATCATGAGAAATATCCAACTAT

CTATCATCTGCGAAAAAAATTGGTAGATTCTACTGATAAAGCGGATTTGCGCTTAAT

CTATTTGGCCTTAGCGCATATGATTAAGTTTCGTGGTCATTTTTTGATTGAGGGAGAT

TTAAATCCTGATAATAGTGATGTGGACAAACTATTTATCCAGTTGGTACAAACCTAC

AATCAATTATTTGAAGAAACCCTATTAACGCAAGTGGAGTAGATGCTAAAGCGAT

TCTTTCTGCACGATTGAGTAAATCAAGACGATTAGAAAATCTCATTGCTCAGCTCCC

CGGTGAGAAGAAAAATGGCTTATTTGGGAATCTCATTGCTTTGTCATTGGGTTTGAC

CCCTAATTTTAAATCAAATTTTGATTTGGCAGAAGATGCTAAATTACAGCTTTCAAA

AGATACTTACGATGATGATTTAGATAATTTATTGGCGCAAATTGGAGATCAATATGC

TGATTTGTTTTTGGCAGCTAAGAATTTATCAGATGCTATTTTACTTTCAGATATCCTA

AGAGTAAATACTGAAATAACTAAGGCTCCCCTATCAGCTTCAATGATTAAACGCTAC

GATGAACATCATCAAGACTTGACTCTTTTAAAAGCTTTAGTTCGACAACAACTTCCA

GAAAAGTATAAAGAAATCTTTTTTGATCAATCAAAAAACGGATATGCAGGTTATATT

GATGGGGGAGCTAGCCAAGAAGAATTTTATAAATTTATCAAACCAATTTTAGAAAA

AATGGATGGTACTGAGGAATTATTGGTGAAACTAAATCGTGAAGATTTGCTGCGCA

AGCAACGGACCTTTGACAACGGCTCTATTCCCCATCAAATTCACTTGGGTGAGCTGC
```

-continued

```
ATGCTATTTTGAGAAGACAAGAAGACTTTTATCCATTTTTAAAAGACAATCGTGAGA
AGATTGAAAAAATCTTGACTTTTCGAATTCCTTATTATGTTGGTCCATTGGCGCGTGG
CAATAGTCGTTTTGCATGGATGACTCGGAAGTCTGAAGAAACAATTACCCCATGGAA
TTTTGAAGAAGTTGTCGATAAAGGTGCTTCAGCTCAATCATTTATTGAACGCATGAC
AAACTTTGATAAAAATCTTCCAAATGAAAAGTACTACCAAAACATAGTTTGCTTTA
TGAGTATTTTACGGTTTATAACGAATTGACAAAGGTCAAATATGTTACTGAAGGAAT
GCGAAAACCAGCATTTCTTTCAGGTGAACAGAAGAAAGCCATTGTTGATTTACTCTT
CAAAACAAATCGAAAGTAACCGTTAAGCAATTAAAAGAAGATTATTTCAAAAAAA
TAGAATGTTTTGATAGTGTTGAAATTTCAGGAGTTGAAGATAGATTTAATGCTTCAT
TAGGTACCTACCATGATTTGCTAAAAATTATTAAAGATAAAGATTTTTTGGATAATG
AAGAAAATGAAGATATCTTAGAGGATATTGTTTTAACATTGACCTTATTTGAAGATA
GGGAGATGATTGAGGAAAGACTTAAAACATATGCTCACCTCTTTGATGATAAGGTG
ATGAAACAGCTTAAACGTCGCCGTTATACTGGTTGGGGACGTTTGTCTCGAAAATTG
ATTAATGGTATTAGGGATAAGCAATCTGGCAAAACAATATTAGATTTTTTGAAATCA
GATGGTTTTGCCAATCGCAATTTTATGCAGCTGATCCATGATGATAGTTTGACATTTA
AAGAAGACATTCAAAAAGCACAAGTGTCTGGACAAGGCGATAGTTTACATGAACAT
ATTGCAAATTTAGCTGGTAGCCCTGCTATTAAAAAAGGTATTTTACAGACTGTAAAA
GTTGTTGATGAATTGGTCAAAGTAATGGGGCGGCATAAGCCAGAAAATATCGTTATT
GAAATGGCACGTGAAAATCAGACAACTCAAAAGGGCCAGAAAAATTCGCGAGAGC
GTATGAAACGAATCGAAGAAGGTATCAAAGAATTAGGAAGTCAGATTCTTAAAGAG
CATCCTGTTGAAAATACTCAATTGCAAATGAAAAGCTCTATCTCTATTATCTCCAA
AATGGAAGAGACATGTATGTGGACCAAGAATTAGATATTAATCGTTTAAGTGATTAT
GATGTCGATCACATTGTTCCACAAAGTTTCCTTAAAGACGATTCAATAGACAATAAG
GTCTTAACGCGTTCTGATAAAAATCGTGGTAAATCGGATAACGTTCCAAGTGAAGAA
GTAGTCAAAAAGATGAAAAACTATTGGAGACAACTTCTAAACGCCAAGTTAATCAC
TCAACGTAAGTTTGATAATTTAACGAAAGCTGAACGTGGAGGTTTGAGTGAACTTGA
TAAAGCTGGTTTTATCAAACGCCAATTGGTTGAAACTCGCCAAATCACTAAGCATGT
GGCACAAATTTTGGATAGTCGCATGAATACTAAATACGATGAAAATGATAAACTTAT
TCGAGAGGTTAAAGTGATTACCTTAAAAATCTAAATTAGTTTCTGACTTCCGAAAAGA
TTTCCAATTCTATAAAGTACGTGAGATTAACAATTACCATCATGCCCATGATGCGTA
TCTAAATGCCGTCGTTGGAACTGCTTTGATTAAGAAATATCCAAAACTTGAATCGGA
GTTTGTCTATGGTGATTATAAAGTTTATGATGTTCGTAAAATGATTGCTAAGTCTGAG
CAAGAAATAGGCAAAGCAACCGCAAAATATTTCTTTTACTCTAATATCATGAACTTC
TTCAAAACAGAAATTACACTTGCAAATGGAGAGATTCGCAAACGCCCTCTAATCGA
AACTAATGGGGAAACTGGAGAAATTGTCTGGGATAAAGGGCGAGATTTTGCCACAG
TGCGCAAAGTATTGTCCATGCCCCAAGTCAATATTGTCAAGAAAACAGAAGTACAG
ACAGGCGGATTCTCCAAGGAGTCAATTTTACCAAAAAGAAATTCGGACAAGCTTATT
GCTCGTAAAAAAGACTGGGATCCAAAAAAATATGGTGGTTTTGATAGTCCAACGGT
AGCTTATTCAGTCCTAGTGGTTGCTAAGGTGGAAAAAGGGAAATCGAAGAAGTTAA
AATCCGTTAAAGAGTTACTAGGGATCACAATTATGGAAAGAAGTTCCTTTGAAAAA
AATCCGATTGACTTTTTAGAAGCTAAAGGATATAAGGAAGTTAAAAAAGACTTAAT
```

```
CATTAAACTACCTAAATATAGTCTTTTTGAGTTAGAAAACGGTCGTAAACGGATGCT

GGCTAGTGCCGGAGAATTACAAAAAGGAAATGAGCTGGCTCTGCCAAGCAAATATG

TGAATTTTTTATATTTAGCTAGTCATTATGAAAAGTTGAAGGGTAGTCCAGAAGATA

ACGAACAAAAACAATTGTTTGTGGAGCAGCATAAGCATTATTTAGATGAGATTATTG

AGCAAATCAGTGAATTTTCTAAGCGTGTTATTTTAGCAGATGCCAATTTAGATAAAG

TTCTTAGTGCATATAACAAACATAGAGACAAACCAATACGTGAACAAGCAGAAAAT

ATTATTCATTTATTTACGTTGACGAATCTTGGAGCTCCCGCTGCTTTTAAATATTTTG

ATACAACAATTGATCGTAAACGATATACGTCTACAAAAGAAGTTTTAGATGCCACTC

TTATCCATCAATCCATCACTGGTCTTTATGAAACACGCATTGATTTGAGTCAGCTAG

GAGGTGACCATCACCACCACCATCAC
```

(+36)dGFP-NLS-Cas9 (SEQ ID NO: 17):

```
ATGGGTGCTAGCAAAGGTGAACGTCTGTTTCGTGGTAAAGTACCGATCTTAGTGGAA

TTAAAGGGCGACGTGAACGGTCATAAATTTAGCGTGCGCGGCAAAGGCAAAGGTGA

CGCTACCCGTGGTAAATTGACCCTGAAGTTTATTTGCACAACAGGCAAATTACCCGT

TCCGTGGCCCACCTTAGTGACCACCCTGACCTATGGCGTTCAGTGCTTCAGTCGTTA

CCCTAAACATATGAAACGTCACGATTTTTTCAAATCAGCCATGCCTAAAGGATATGT

TCAAGAGCGTACAATCAGCTTCAAGAAGGATGGCAAATATAAAACGCGTGCGGAAG

TGAAATTTGAAGGCCGCACATTAGTAAATCGTATCAAACTGAAAGGTCGTGACTTCA

AAGAAAAAGGCAACATTTTAGGCCATAAACTGCGTTATAACTTTAATTCTCATAAGG

TGTATATTACGGCCGATAAACGCAAGAATGGTATCAAGGCAAAATTCAAAATTCGC

CATAACGTGAAAGACGGCAGCGTTCAATTAGCGGATCATTATCAACAAAACACGCC

GATTGGTCGCGGGCCTGTACTGTTACCTCGCAACCACTACCTGAGCACCCGTTCTAA

ACTGAGCAAAGATCCGAAAGAAAAACGCGATCACATGGTTCTGTTAGAATTCGTGA

CCGCTGCAGGCATTAAGCACGGACGCGACGAACGCTACAAGACCGGTGGTAGCGGT

GGTTCTGGTGGTTCTGGTGGTAGCGGCGGTAGCGGTGGTAGCGGTGGTAGCGGTGG

CAGCGGCGGTACCGCGCTCGCGCTGCCCAAGAAGAAGAGGAAGGTGATGGATAAG

AAATACTCAATAGGCTTAGATATCGGCACAAATAGCGTCGGATGGGCGGTGATCAC

TGATGAATATAAGGTTCCGTCTAAAAAGTTCAAGGTTCTGGGAAATACAGACCGCC

ACAGTATCAAAAAAATCTTATAGGGGCTCTTTTATTTGACAGTGGAGAGACAGCG

GAAGCGACTCGTCTCAAACGGACAGCTCGTAGAAGGTATACACGTCGGAAGAATCG

TATTTGTTATCTACAGGAGATTTTTTCAAATGAGATGGCGAAAGTAGATGATAGTTT

CTTTCATCGACTTGAAGAGTCTTTTTTGGTGGAAGAAGACAAGAAGCATGAACGTCA

TCCTATTTTTGGAAATATAGTAGATGAAGTTGCTTATCATGAGAAATATCCAACTAT

CTATCATCTGCGAAAAAATTGGTAGATTCTACTGATAAAGCGGATTTGCGCTTAAT

CTATTTGGCCTTAGCGCATATGATTAAGTTTCGTGGTCATTTTTTGATTGAGGGAGAT

TTAAATCCTGATAATAGTGATGTGGACAAACTATTTATCCAGTTGGTACAAACCTAC

AATCAATTATTTGAAGAAACCCTATTAACGCAAGTGGAGTAGATGCTAAAGCGAT

TCTTTCTGCACGATTGAGTAAATCAAGACGATTAGAAAATCTCATTGCTCAGCTCCC

CGGTGAGAAGAAAAATGGCTTATTTGGGAATCTCATTGCTTTGTCATTGGGTTTGAC

CCCTAATTTTAAATCAAATTTTGATTTGGCAGAAGATGCTAAATTACAGCTTTCAAA

AGATACTTACGATGATGATTTAGATAATTTATTGGCGCAAATTGGAGATCAATATGC
```

-continued

```
TGATTTGTTTTTGGCAGCTAAGAATTTATCAGATGCTATTTTACTTTCAGATATCCTA

AGAGTAAATACTGAAATAACTAAGGCTCCCCTATCAGCTTCAATGATTAAACGCTAC

GATGAACATCATCAAGACTTGACTCTTTTAAAAGCTTTAGTTCGACAACAACTTCCA

GAAAAGTATAAAGAAATCTTTTTTGATCAATCAAAAAACGGATATGCAGGTTATATT

GATGGGGAGCTAGCCAAGAAGAATTTTATAAATTTATCAAACCAATTTTAGAAAA

AATGGATGGTACTGAGGAATTATTGGTGAAACTAAATCGTGAAGATTTGCTGCGCA

AGCAACGGACCTTTGACAACGGCTCTATTCCCCATCAAATTCACTTGGGTGAGCTGC

ATGCTATTTTGAGAAGACAAGAAGACTTTTATCCATTTTTAAAAGACAATCGTGAGA

AGATTGAAAAAATCTTGACTTTTCGAATTCCTTATTATGTTGGTCCATTGGCGCGTGG

CAATAGTCGTTTTGCATGGATGACTCGGAAGTCTGAAGAAACAATTACCCCATGGAA

TTTTGAAGAAGTTGTCGATAAAGGTGCTTCAGCTCAATCATTTATTGAACGCATGAC

AAACTTTGATAAAAATCTTCCAAATGAAAAGTACTACCAAAACATAGTTTGCTTTA

TGAGTATTTTACGGTTTATAACGAATTGACAAAGGTCAAATATGTTACTGAAGGAAT

GCGAAAACCAGCATTTCTTTCAGGTGAACAGAAGAAAGCCATTGTTGATTTACTCTT

CAAAACAAATCGAAAAGTAACCGTTAAGCAATTAAAAGAAGATTATTTCAAAAAAA

TAGAATGTTTTGATAGTGTTGAAATTTCAGGAGTTGAAGATAGATTTAATGCTTCAT

TAGGTACCTACCATGATTTGCTAAAAATTATTAAAGATAAAGATTTTTTGGATAATG

AAGAAAATGAAGATATCTTAGAGGATATTGTTTTAACATTGACCTTATTTGAAGATA

GGGAGATGATTGAGGAAAGACTTAAAACATATGCTCACCTCTTTGATGATAAGGTG

ATGAAACAGCTTAAACGTCGCCGTTATACTGGTTGGGGACGTTTGTCTCGAAAATTG

ATTAATGGTATTAGGGATAAGCAATCTGGCAAAACAATATTAGATTTTTTGAAATCA

GATGGTTTTGCCAATCGCAATTTTATGCAGCTGATCCATGATGATAGTTTGACATTTA

AAGAAGACATTCAAAAAGCACAAGTGTCTGGACAAGGCGATAGTTTACATGAACAT

ATTGCAAATTTAGCTGGTAGCCCTGCTATTAAAAAAGGTATTTTACAGACTGTAAAA

GTTGTTGATGAATTGGTCAAAGTAATGGGGCGGCATAAGCCAGAAAATATCGTTATT

GAAATGGCACGTGAAAATCAGACAACTCAAAAGGGCCAGAAAAATTCGCGAGAGC

GTATGAAACGAATCGAAGAAGGTATCAAAGAATTAGGAAGTCAGATTCTTAAAGAG

CATCCTGTTGAAAATACTCAATTGCAAATGAAAAGCTCTATCTCTATTATCTCCAA

AATGGAAGAGACATGTATGTGGACCAAGAATTAGATATTAATCGTTTAAGTGATTAT

GATGTCGATCACATTGTTCCACAAAGTTTCCTTAAAGACGATTCAATAGACAATAAG

GTCTTAACGCGTTCTGATAAAAATCGTGGTAAATCGGATAACGTTCCAAGTGAAGAA

GTAGTCAAAAAGATGAAAAACTATTGGAGACAACTTCTAAACGCCAAGTTAATCAC

TCAACGTAAGTTTGATAATTTAACGAAAGCTGAACGTGGAGGTTTGAGTGAACTTGA

TAAAGCTGGTTTTATCAAACGCCAATTGGTTGAAACTCGCCAAATCACTAAGCATGT

GGCACAAATTTTGGATAGTCGCATGAATACTAAATACGATGAAAATGATAAACTTAT

TCGAGAGGTTAAAGTGATTACCTTAAAATCTAAATTAGTTTCTGACTTCCGAAAGA

TTTCCAATTCTATAAAGTACGTGAGATTAACAATTACCATCATGCCCATGATGCGTA

TCTAAATGCCGTCGTTGGAACTGCTTTGATTAAGAAATATCCAAAACTTGAATCGGA

GTTTGTCTATGGTGATTATAAAGTTTATGATGTTCGTAAAATGATTGCTAAGTCTGAG

CAAGAAATAGGCAAAGCAACCGCAAAATATTTCTTTTACTCTAATATCATGAACTTC
```

-continued

TTCAAAACAGAAATTACACTTGCAAATGGAGAGATTCGCAAACGCCCTCTAATCGA

AACTAATGGGGAAACTGGAGAAATTGTCTGGGATAAAGGGCGAGATTTTGCCACAG

TGCGCAAAGTATTGTCCATGCCCCAAGTCAATATTGTCAAGAAAACAGAAGTACAG

ACAGGCGGATTCTCCAAGGAGTCAATTTTACCAAAAAGAAATTCGGACAAGCTTATT

GCTCGTAAAAAAGACTGGGATCCAAAAAAATATGGTGGTTTTGATAGTCCAACGGT

AGCTTATTCAGTCCTAGTGGTTGCTAAGGTGGAAAAAGGGAAATCGAAGAAGTTAA

AATCCGTTAAAGAGTTACTAGGGATCACAATTATGGAAAGAAGTTCCTTTGAAAAA

AATCCGATTGACTTTTTAGAAGCTAAAGGATATAAGGAAGTTAAAAAAGACTTAAT

CATTAAACTACCTAAATATAGTCTTTTTGAGTTAGAAAACGGTCGTAAACGGATGCT

GGCTAGTGCCGGAGAATTACAAAAAGGAAATGAGCTGGCTCTGCCAAGCAAATATG

TGAATTTTTTATATTTAGCTAGTCATTATGAAAAGTTGAAGGGTAGTCCAGAAGATA

ACGAACAAAAACAATTGTTTGTGGAGCAGCATAAGCATTATTTAGATGAGATTATTG

AGCAAATCAGTGAATTTTCTAAGCGTGTTATTTTAGCAGATGCCAATTTAGATAAAG

TTCTTAGTGCATATAACAAACATAGAGACAAACCAATACGTGAACAAGCAGAAAAT

ATTATTCATTTATTTACGTTGACGAATCTTGGAGCTCCCGCTGCTTTTAAATATTTG

ATACAACAATTGATCGTAAACGATATACGTCTACAAAAGAAGTTTTAGATGCCACTC

TTATCCATCAATCCATCACTGGTCTTTATGAAACACGCATTGATTTGAGTCAGCTAG

GAGGTGACCATCACCACCACCATCAC

Cas9-NLS-6xHis (SEQ ID NO: 18):
ATGGATAAGAAATACTCAATAGGCTTAGATATCGGCACAAATAGCGTCGGATGGGC

GGTGATCACTGATGAATATAAGGTTCCGTCTAAAAAGTTCAAGGTTCTGGGAAATAC

AGACCGCCACAGTATCAAAAAAAATCTTATAGGGGCTCTTTTATTTGACAGTGGAGA

GACAGCGGAAGCGACTCGTCTCAAACGGACAGCTCGTAGAAGGTATACACGTCGGA

AGAATCGTATTTGTTATCTACAGGAGATTTTTTCAAATGAGATGGCGAAAGTAGATG

ATAGTTTCTTTCATCGACTTGAAGAGTCTTTTTTGGTGGAAGAAGACAAGAAGCATG

AACGTCATCCTATTTTTGGAAATATAGTAGATGAAGTTGCTTATCATGAGAAATATC

CAACTATCTATCATCTGCGAAAAAAATTGGTAGATTCTACTGATAAAGCGGATTTGC

GCTTAATCTATTTGGCCTTAGCGCATATGATTAAGTTTCGTGGTCATTTTTTGATTGA

GGGAGATTTAAATCCTGATAATAGTGATGTGGACAAACTATTTATCCAGTTGGTACA

AACCTACAATCAATTATTTGAAGAAACCCTATTAACGCAAGTGGAGTAGATGCTA

AAGCGATTCTTTCTGCACGATTGAGTAAATCAAGACGATTAGAAAATCTCATTGCTC

AGCTCCCCGGTGAGAAGAAAAATGGCTTATTTGGGAATCTCATTGCTTTGTCATTGG

GTTTGACCCCTAATTTTAAATCAAATTTTGATTTGGCAGAAGATGCTAAATTACAGC

TTTCAAAAGATACTTACGATGATGATTTAGATAATTTATTGGCGCAAATTGGAGATC

AATATGCTGATTTGTTTTTGGCAGCTAAGAATTTATCAGATGCTATTTTACTTTCAGA

TATCCTAAGAGTAAATACTGAAATAACTAAGGCTCCCCTATCAGCTTCAATGATTAA

ACGCTACGATGAACATCATCAAGACTTGACTCTTTTAAAAGCTTTAGTTCGACAACA

ACTTCCAGAAAAGTATAAAGAAATCTTTTTTGATCAATCAAAAAACGGATATGCAG

GTTATATTGATGGGGGAGCTAGCCAAGAAGAATTTTATAAATTTATCAAACCAATTT

TAGAAAAAATGGATGGTACTGAGGAATTATTGGTGAAACTAAATCGTGAAGATTTG

CTGCGCAAGCAACGGACCTTTGACAACGGCTCTATTCCCCATCAAATTCACTTGGGT

-continued

```
GAGCTGCATGCTATTTTGAGAAGACAAGAAGACTTTTATCCATTTTTAAAAGACAAT
CGTGAGAAGATTGAAAAAATCTTGACTTTTCGAATTCCTTATTATGTTGGTCCATTGG
CGCGTGGCAATAGTCGTTTTGCATGGATGACTCGGAAGTCTGAAGAAACAATTACCC
CATGGAATTTTGAAGAAGTTGTCGATAAAGGTGCTTCAGCTCAATCATTTATTGAAC
GCATGACAAACTTTGATAAAAATCTTCCAAATGAAAAGTACTACCAAACATAGT
TTGCTTTATGAGTATTTTACGGTTTATAACGAATTGACAAAGGTCAAATATGTTACTG
AAGGAATGCGAAAACCAGCATTTCTTTCAGGTGAACAGAAGAAAGCCATTGTTGAT
TTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAAT
GCTTCATTAGGTACCTACCATGATTTGCTAAAAATTATTAAAGATAAAGATTTTTTG
GATAATGAAGAAAATGAAGATATCTTAGAGGATATTGTTTTAACATTGACCTTATTT
GAAGATAGGGAGATGATTGAGGAAAGACTTAAAACATATGCTCACCTCTTTGATGA
TAAGGTGATGAAACAGCTTAAACGTCGCCGTTATACTGGTTGGGGACGTTTGTCTCG
AAAATTGATTAATGGTATTAGGGATAAGCAATCTGGCAAAACAATATTAGATTTTTT
GAAATCAGATGGTTTTGCCAATCGCAATTTTATGCAGCTGATCCATGATGATAGTTT
GACATTTAAAGAAGACATTCAAAAAGCACAAGTGTCTGGACAAGGCGATAGTTTAC
ATGAACATATTGCAAATTTAGCTGGTAGCCCTGCTATTAAAAAAGGTATTTTACAGA
CTGTAAAAGTTGTTGATGAATTGGTCAAAGTAATGGGGCGGCATAAGCCAGAAAAT
ATCGTTATTGAAATGGCACGTGAAAATCAGACAACTCAAAAGGGCCAGAAAAATTC
GCGAGAGCGTATGAAACGAATCGAAGAAGGTATCAAAGAATTAGGAAGTCAGATTC
TTAAAGAGCATCCTGTTGAAAATACTCAATTGCAAAATGAAAAGCTCTATCTCTATT
ATCTCCAAAATGGAAGAGACATGTATGTGGACCAAGAATTAGATATTAATCGTTTAA
GTGATTATGATGTCGATCACATTGTTCCACAAAGTTTCCTTAAAGACGATTCAATAG
ACAATAAGGTCTTAACGCGTTCTGATAAAAATCGTGGTAAATCGGATAACGTTCCAA
GTGAAGAAGTAGTCAAAAAGATGAAAAACTATTGGAGACAACTTCTAAACGCCAAG
TTAATCACTCAACGTAAGTTTGATAATTTAACGAAAGCTGAACGTGGAGGTTTGAGT
GAACTTGATAAAGCTGGTTTTATCAAACGCCAATTGGTTGAAACTCGCCAAATCACT
AAGCATGTGGCACAAATTTTGGATAGTCGCATGAATACTAAATACGATGAAAATGA
TAAACTTATTCGAGAGGTTAAAGTGATTACCTTAAAATCTAAATTAGTTTCTGACTTC
CGAAAAGATTTCCAATTCTATAAAGTACGTGAGATTAACAATTACCATCATGCCCAT
GATGCGTATCTAAATGCCGTCGTTGGAACTGCTTTGATTAAGAAATATCCAAAACTT
GAATCGGAGTTTGTCTATGGTGATTATAAAGTTTATGATGTTCGTAAAATGATTGCT
AAGTCTGAGCAAGAAATAGGCAAAGCAACCGCAAAATATTTCTTTTACTCTAATATC
ATGAACTTCTTCAAAACAGAAATTACACTTGCAAATGGAGAGATTCGCAAACGCCCT
CTAATCGAAACTAATGGGGAAACTGGAGAAATTGTCTGGGATAAAGGGCGAGATTT
TGCCACAGTGCGCAAAGTATTGTCCATGCCCCAAGTCAATATTGTCAAGAAAACAG
AAGTACAGACAGGCGGATTCTCCAAGGAGTCAATTTTACCAAAAAGAAATTCGGAC
AAGCTTATTGCTCGTAAAAAAGACTGGGATCCAAAAAAATATGGTGGTTTTGATAGT
CCAACGGTAGCTTATTCAGTCCTAGTGGTTGCTAAGGTGGAAAAAGGGAAATCGAA
GAAGTTAAAATCCGTTAAAGAGTTACTAGGGATCACAATTATGGAAAGAAGTTCCTT
TGAAAAAAATCCGATTGACTTTTTAGAAGCTAAAGGATATAAGGAAGTTAAAAAAG
```

ACTTAATCATTAAACTACCTAAATATAGTCTTTTTGAGTTAGAAAACGGTCGTAAAC

GGATGCTGGCTAGTGCCGGAGAATTACAAAAAGGAAATGAGCTGGCTCTGCCAAGC

AAATATGTGAATTTTTTATATTTAGCTAGTCATTATGAAAAGTTGAAGGGTAGTCCA

GAAGATAACGAACAAAAACAATTGTTTGTGGAGCAGCATAAGCATTATTTAGATGA

GATTATTGAGCAAATCAGTGAATTTTCTAAGCGTGTTATTTTAGCAGATGCCAATTT

AGATAAAGTTCTTAGTGCATATAACAAACATAGAGACAAACCAATACGTGAACAAG

CAGAAAATATTATTCATTTATTTACGTTGACGAATCTTGGAGCTCCCGCTGCTTTTAA

ATATTTTGATACAACAATTGATCGTAAACGATATACGTCTACAAAAGAAGTTTTAGA

TGCCACTCTTATCCATCAATCCATCACTGGTCTTTATGAAACACGCATTGATTTGAGT

CAGCTAGGAGGTGACCCCAAGAAGAAGAGGAAGGTGATGGATAAGCATCACCACC

ACCATCAC dCas9-VP64-6xHis (SEQ ID NO: 19):
ATGGATAAGAAATACTCAATAGGCTTAGCTATCGGCACAAATAGCGTCGGATGGGC

GGTGATCACTGATGAATATAAGGTTCCGTCTAAAAAGTTCAAGGTTCTGGGAAATAC

AGACCGCCACAGTATCAAAAAAAATCTTATAGGGGCTCTTTTATTTGACAGTGGAGA

GACAGCGGAAGCGACTCGTCTCAAACGGACAGCTCGTAGAAGGTATACACGTCGGA

AGAATCGTATTTGTTATCTACAGGAGATTTTTTCAAATGAGATGGCGAAAGTAGATG

ATAGTTTCTTTCATCGACTTGAAGAGTCTTTTTTGGTGGAAGAAGACAAGAAGCATG

AACGTCATCCTATTTTTGGAAATATAGTAGATGAAGTTGCTTATCATGAGAAATATC

CAACTATCTATCATCTGCGAAAAAAATTGGTAGATTCTACTGATAAAGCGGATTTGC

GCTTAATCTATTTGGCCTTAGCGCATATGATTAAGTTTCGTGGTCATTTTTTGATTGA

GGGAGATTTAAATCCTGATAATAGTGATGTGGACAAACTATTTATCCAGTTGGTACA

AACCTACAATCAATTATTTGAAGAAAACCCTATTAACGCAAGTGGAGTAGATGCTA

AAGCGATTCTTTCTGCACGATTGAGTAAATCAAGACGATTAGAAAATCTCATTGCTC

AGCTCCCCGGTGAGAAGAAAAATGGCTTATTTGGGAATCTCATTGCTTTGTCATTGG

GTTTGACCCCTAATTTTAAATCAAATTTTGATTTGGCAGAAGATGCTAAATTACAGC

TTTCAAAAGATACTTACGATGATGATTTAGATAATTTATTGGCGCAAATTGGAGATC

AATATGCTGATTTGTTTTTGGCAGCTAAGAATTTATCAGATGCTATTTTACTTTCAGA

TATCCTAAGAGTAAATACTGAAATAACTAAGGCTCCCCTATCAGCTTCAATGATTAA

ACGCTACGATGAACATCATCAAGACTTGACTCTTTTAAAAGCTTTAGTTCGACAACA

ACTTCCAGAAAAGTATAAAGAAATCTTTTTTGATCAATCAAAAAACGGATATGCAG

GTTATATTGATGGGGGAGCTAGCCAAGAAGAATTTTATAAATTTATCAAACCAATTT

TAGAAAAAATGGATGGTACTGAGGAATTATTGGTGAAACTAAATCGTGAAGATTTG

CTGCGCAAGCAACGGACCTTTGACAACGGCTCTATTCCCCATCAAATTCACTTGGGT

GAGCTGCATGCTATTTTGAGAAGACAAGAAGACTTTTATCCATTTTTAAAAGACAAT

CGTGAGAAGATTGAAAAAATCTTGACTTTTCGAATTCCTTATTATGTTGGTCCATTGG

CGCGTGGCAATAGTCGTTTTGCATGGATGACTCGGAAGTCTGAAGAAACAATTACCC

CATGGAATTTTGAAGAAGTTGTCGATAAAGGTGCTTCAGCTCAATCATTTATTGAAC

GCATGACAAACTTTGATAAAAATCTTCCAAATGAAAAAGTACTACCAAAACATAGT

TTGCTTTATGAGTATTTTACGGTTTATAACGAATTGACAAAGGTCAAATATGTTACTG

AAGGAATGCGAAAACCAGCATTTCTTTCAGGTGAACAGAAGAAAGCCATTGTTGAT

-continued

```
TTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAAT
GCTTCATTAGGTACCTACCATGATTTGCTAAAAATTATTAAAGATAAAGATTTTTTG
GATAATGAAGAAAATGAAGATATCTTAGAGGATATTGTTTTAACATTGACCTTATTT
GAAGATAGGGAGATGATTGAGGAAAGACTTAAAACATATGCTCACCTCTTTGATGA
TAAGGTGATGAAACAGCTTAAACGTCGCCGTTATACTGGTTGGGGACGTTTGTCTCG
AAAATTGATTAATGGTATTAGGGATAAGCAATCTGGCAAAACAATATTAGATTTTTT
GAAATCAGATGGTTTTGCCAATCGCAATTTTATGCAGCTGATCCATGATGATAGTTT
GACATTTAAAGAAGACATTCAAAAAGCACAAGTGTCTGGACAAGGCGATAGTTTAC
ATGAACATATTGCAAATTTAGCTGGTAGCCCTGCTATTAAAAAAGGTATTTTACAGA
CTGTAAAAGTTGTTGATGAATTGGTCAAAGTAATGGGGCGGCATAAGCCAGAAAAT
ATCGTTATTGAAATGGCACGTGAAAATCAGACAACTCAAAAGGGCCAGAAAAATTC
GCGAGAGCGTATGAAACGAATCGAAGAAGGTATCAAAGAATTAGGAAGTCAGATTC
TTAAAGAGCATCCTGTTGAAAATACTCAATTGCAAAATGAAAAGCTCTATCTCTATT
ATCTCCAAAATGGAAGAGACATGTATGTGGACCAAGAATTAGATATTAATCGTTTAA
GTGATTATGATGTCGATGCCATTGTTCCACAAAGTTTCCTTAAAGACGATTCAATAG
ACAATAAGGTCTTAACGCGTTCTGATAAAAATCGTGGTAAATCGGATAACGTTCCAA
GTGAAGAAGTAGTCAAAAAGATGAAAAACTATTGGAGACAACTTCTAAACGCCAAG
TTAATCACTCAACGTAAGTTTGATAATTTAACGAAAGCTGAACGTGGAGGTTTGAGT
GAACTTGATAAAGCTGGTTTTATCAAACGCCAATTGGTTGAAACTCGCCAAATCACT
AAGCATGTGGCACAAATTTTGGATAGTCGCATGAATACTAAATACGATGAAAATGA
TAAACTTATTCGAGAGGTTAAAGTGATTACCTTAAAATCTAAATTAGTTTCTGACTTC
CGAAAAGATTTCCAATTCTATAAAGTACGTGAGATTAACAATTACCATCATGCCCAT
GATGCGTATCTAAATGCCGTCGTTGGAACTGCTTTGATTAAGAAATATCCAAAACTT
GAATCGGAGTTTGTCTATGGTGATTATAAAGTTTATGATGTTCGTAAAATGATTGCT
AAGTCTGAGCAAGAAATAGGCAAAGCAACCGCAAAATATTTCTTTTACTCTAATATC
ATGAACTTCTTCAAAACAGAAATTACACTTGCAAATGGAGAGATTCGCAAACGCCCT
CTAATCGAAACTAATGGGGAAACTGGAGAAATTGTCTGGGATAAAGGGCGAGATTT
TGCCACAGTGCGCAAAGTATTGTCCATGCCCCAAGTCAATATTGTCAAGAAAACAG
AAGTACAGACAGGCGGATTCTCCAAGGAGTCAATTTTACCAAAAAGAAATTCGGAC
AAGCTTATTGCTCGTAAAAAAGACTGGGATCCAAAAAAATATGGTGGTTTTGATAGT
CCAACGGTAGCTTATTCAGTCCTAGTGGTTGCTAAGGTGGAAAAAGGGAAATCGAA
GAAGTTAAAATCCGTTAAAGAGTTACTAGGGATCACAATTATGGAAAGAAGTTCCTT
TGAAAAAAATCCGATTGACTTTTTAGAAGCTAAAGGATATAAGGAAGTTAAAAAAG
ACTTAATCATTAAACTACCTAAATATAGTCTTTTTGAGTTAGAAAACGGTCGTAAAC
GGATGCTGGCTAGTGCCGGAGAATTACAAAAAGGAAATGAGCTGGCTCTGCCAAGC
AAATATGTGAATTTTTTATATTTAGCTAGTCATTATGAAAAGTTGAAGGGTAGTCCA
GAAGATAACGAACAAAAACAATTGTTTGTGGAGCAGCATAAGCATTATTTAGATGA
GATTATTGAGCAAATCAGTGAATTTTCTAAGCGTGTTATTTTAGCAGATGCCAATTT
AGATAAAGTTCTTAGTGCATATAACAAACATAGAGACAAACCAATACGTGAACAAG
```

```
-continued
CAGAAAATATTATTCATTTATTTACGTTGACGAATCTTGGAGCTCCCGCTGCTTTTAA

ATATTTTGATACAACAATTGATCGTAAACGATATACGTCTACAAAAGAAGTTTTAGA

TGCCACTCTTATCCATCAATCCATCACTGGTCTTTATGAAACACGCATTGATTTGAGT

CAGCTAGGAGGTGACGGTTCTCCCAAGAAGAAGAGGAAAGTCTCGAGCGACTACAA

AGACCATGACGGTGATTATAAAGATCATGACATCGATTACAAGGATGACGATGACA

AGGCTGCAGGAGGCGGTGGAAGCGGGCGCGCCGACGCGCTGGACGATTTCGATCTC

GACATGCTGGGTTCTGATGCCCTCGATGACTTTGACCTGGATATGTTGGGAAGCGAC

GCATTGGATGACTTTGATCTGGACATGCTCGGCTCCGATGCTCTGGACGATTTCGAT

CTCGATATGTTACATCACCACCACCATCAC
```

Example 2: Delivery of Cas9:gRNA in Adult Cochlea In Vivo

To study if Cas9 protein with gRNA can be delivered to adult cochlea in vivo, Cas9:gRNA-GFP complexed with lipofectamine2000 was microinjected in 1-month-old Atoh1-GFP mouse cochlea. Two weeks after injection disappearance of GFP signals in some outer hair cells (FIG. 1B, OHC in brackets) was observed whereas in control saline injected inner ear all OHCs have GFP signal (FIGS. 1A, 1B). OHCs without GFP could still be co-labeled with DAPI and Myo7a, a demonstration of survival of OHCs.

Cas9:gRNA Mediated Genome Editing in Pmca2 Mutant Mouse with Restoration of Hearing:

Mutation in Pmca2 gene (2765C→T) causes hereditary hearing loss in transgenic mouse (Oblivion, Obl) (Spiden et al., 2008; Street, McKee-Johnson, Fonseca, Tempel, & Noben-Trauth, 1998). To study if Cas9:gRNA can be used to disrupt the mutation to restore hearing, a set of gRNAs were designed, that target the mutation for Cas9:gRNA injection into neonatal Obl heterozygous (Pmca2$^{Obl/+}$) mouse inner ear at postnatal day 1 (P1) (FIG. 2; SEQ ID NOS: 21-32). A hearing study (ABR and DPOAE) was performed on the injected and uninjected inner ears, one, two and three months after injection.

Figure 3:
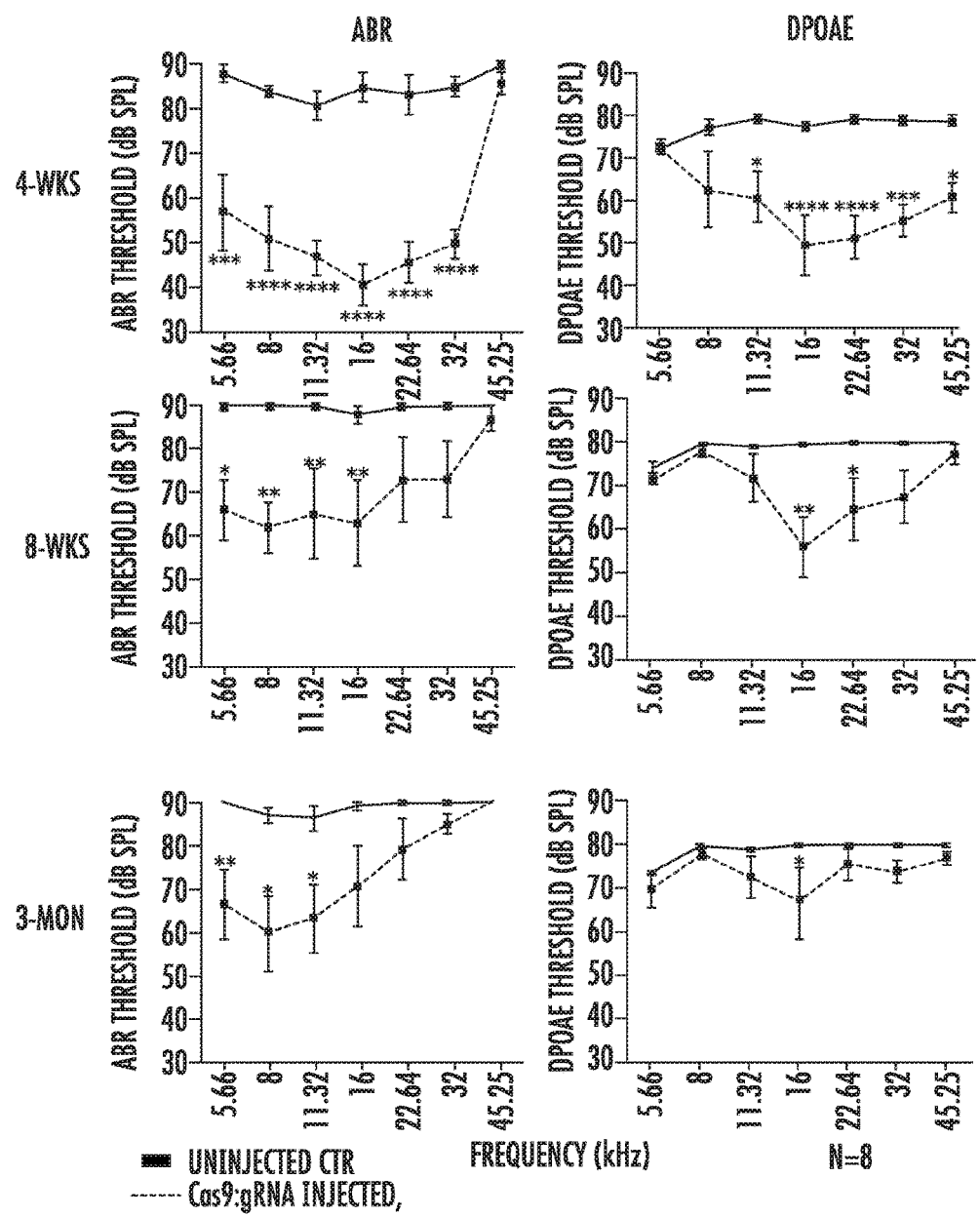
FIG. 3 is a series of graphs showing that Cas9:gRNA injection restored hearing in the Obl heterozygous mice. In the uninjected inner ears, profound hearing loss was shown by the complete lack of ABR and DPOAE across all frequencies at the highest sound pressure level (SPL) from 4 weeks to three months. In the injected inner ear, significant hearing recovery was achieved across most frequencies (except for 45.25 kHz) by ABR as well as by DPOAE. In the middle frequencies 11.32 to 22.64 kHz, the recovery was over 50 dB, a demonstration of restoration of hearing to near normal levels. At 8 weeks and three months of age, hearing recovery was largely maintained shown by ABR and DPOAE. Deterioration in high frequency was seen at later stages.
Figure 4:
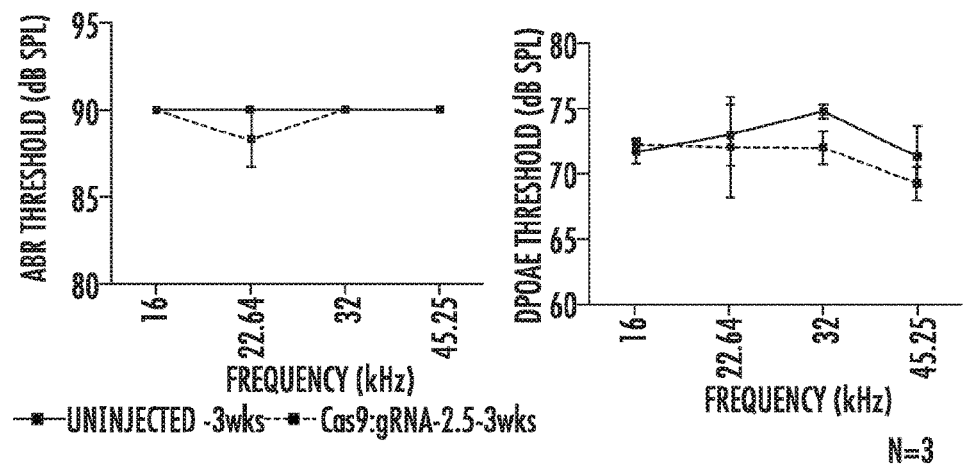
FIG. 4 are graphs showing that hearing recovery is gRNA specific. An example of a gRNA-2.5-mut with different sequence did not result in hearing improvement after injection with Cas9. gRNAs against wildtype Pmca2 did not improve hearing either.
Figure 5:
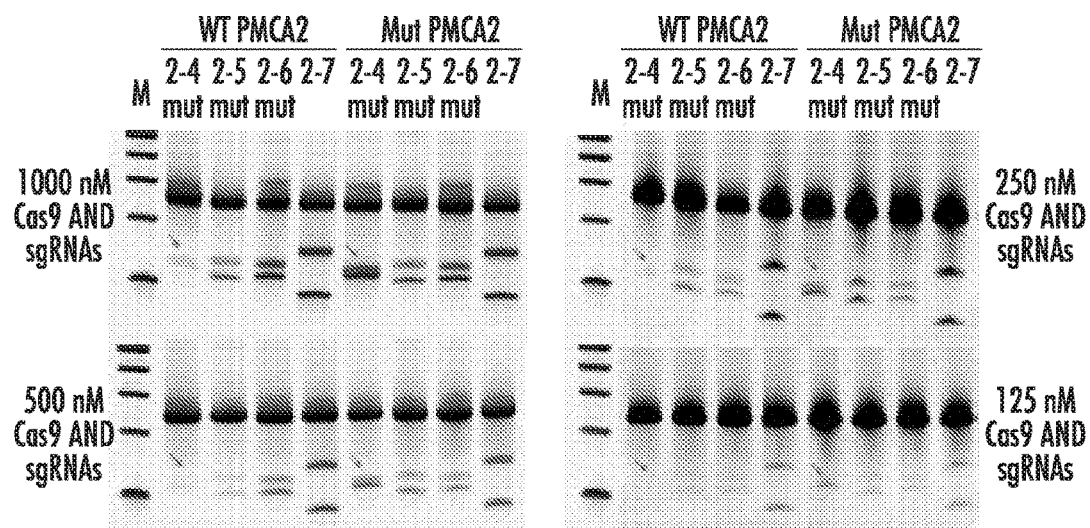
FIG. 5 shows the high-efficiency cleavage by specific gRNA-2.4-mut. Different concentrations of Cas9 protein and gRNAs were tested for DNA cleavage in vitro. Only gRNA-2.4-mut showed cleavage in mutant but not in wildtype Pmca2 genomic region at 125 nM. Whereas other gRNAs showed cleavages in both mutant and wildtype genomic DNA.

In the uninjected cochlea, the hearing test showed profound hearing loss and the lack of DPOAE at the highest sound level used (90 dB) across all frequencies at one month of age, and hearing loss persisted throughout the rest of study (FIG. 3). In the injected mouse cochlea, drastic hearing improvement was observed, shown by ABR and DPOAE in all frequencies except for the highest frequency of 45.25 kHz. Hearing restoration was maintained in two and three month old cochleas injected with Cas9:gRNA (FIG. 3). Of all the gRNAs that targeted the mutation, only one (2.4-mut) showed hearing recovery, strongly supporting the importance in selecting gRNA with the specific effect (FIG. 4). To further evaluate the specificity of the study, gRNAs were designed against wildtype Pmca2 gene for inner ear injection (FIG. 2; SEQ ID NOS: 21-32). With wildtype gRNAs hearing improvement was not detected in the Pmca2$^{Obl/+}$ cochlea injected animals. T7EI endonuclease assay was performed and showed that in vitro Cas9:gRNA cleaved mutant DNA (FIG. 5) at 125 nM. High-throughput sequencing (HTS) was performed to confirm that the strategy induces indels (insertions and deletions) in the injected inner ear, to provide molecular proof of genome editing.

Figure 6A:
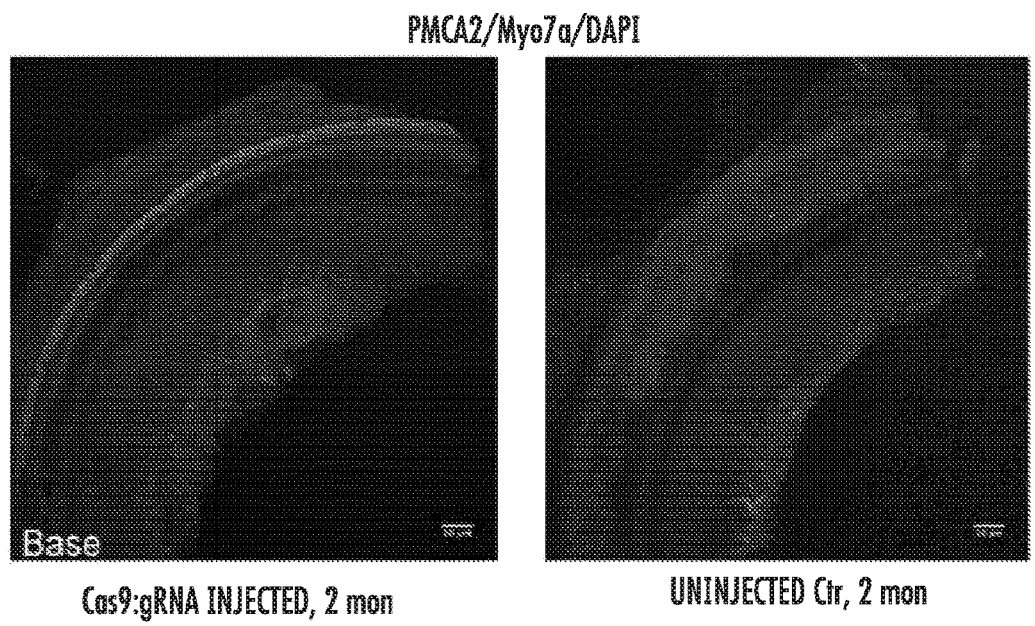
FIG. 6A, 6B show that Cas9:gRNA injection promotes outer hair cell survival.
Figure 6B:
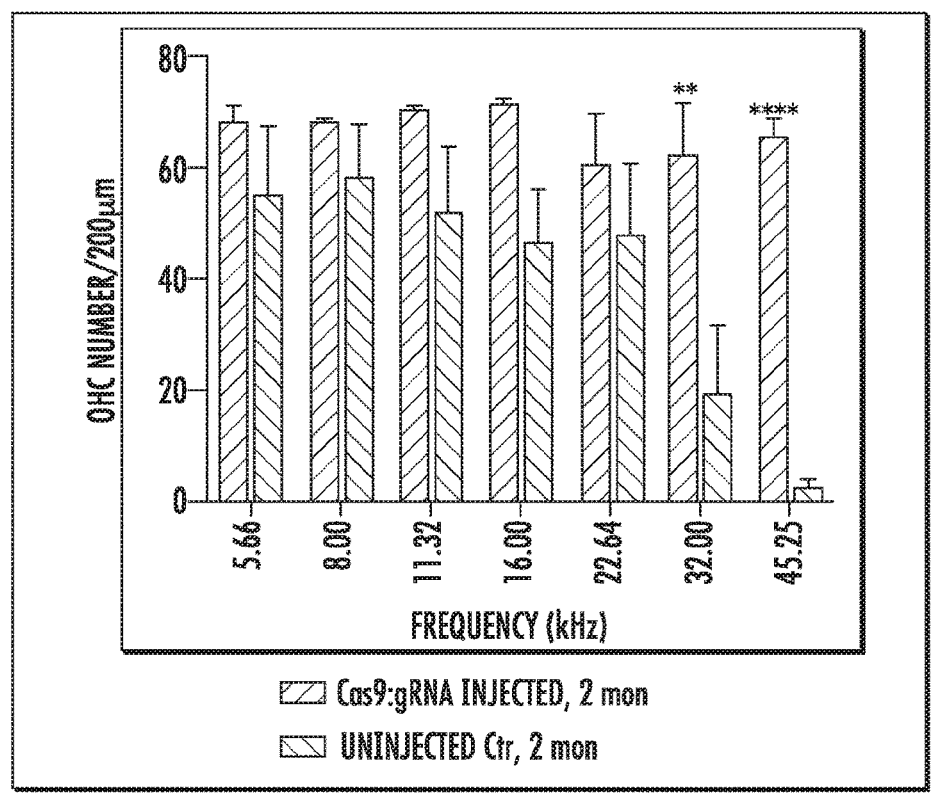

To further correlate hearing recovery with hair cell status, injected and control inner ears were examined. By immunolabeling it was found that a majority of outer hair cells survived after injection whereas in control inner ear a majority of outer hair cells died especially in the base to middle turn (FIGS. 6A, 6B). In comparison to control, the injected inner ear maintained a large number neurites of spiral ganglion neurons (FIGS. 7A, 7B). Thus Cas9:gRNA mediated genome editing leads to outer hair cell survival and maintain their connection with neurons, resulting hearing recovery.

As mutations in PMCA2 gene are involved in human genetic deafness (Schultz, J. M. et al., 2005, N Engl J Med. 352(15), 1557-1564) this approach would lead to intervention in those patients. While this study is focused on the disruption of dominant mutation, it is highly feasible that a similar approach can be applied to recessive mutations when efficient for homology-directed repair (HDR) is improved.

An additional mechanism for hearing recovery in the injected inner ear could be due to interference of Cas9:gRNA that blocks of Pmca2 mutant transcription. Such interference has been previously reported (LRussa & Qi, 2015, Mol Cell Biol. doi.org/10.1128/MCB.00512-15). Interference by Cas9:gRNA to disrupt mutant gene that leads to functional recovery of hearing is a new mechanism that can be applied to other dominant hearing loss and genetic diseases in general.

Hearing Restoration in Tmc1 Beethoven (Bth) Genetic Hearing Loss Mouse Model:

To further study the generality of the Cas9:gRNA approach in restoring hearing, a Tmc1 mouse mutant (Bth) was used due to a dominant mutation (1235T→A that leads to M412K) (Vreugde, S., et al., (2002). Nat Genet, 30(3), 257-258), using the same procedure as outlined in Pmca2 study. A series of gRNA against the mutation as well as wildtype Tmc1 gene were designed. Tmc1 heterozygous mouse inner ear were injected with Cas9:gRNA at P1 and their hearing was assessed at 4 weeks of age. The uninjected inner ears served as control.

By ABR, a generally improved hearing was found across all frequencies with significant improvements at the frequencies of 11.32, 16 and 22.64 kHz. Over 20 dB improvements were seen in the latter two frequencies. For the Bth mice DPOAE were present. The injected ears had DPOAE similar to the uninjected inner ears with a slight elevation from 8 to 16 kHz (FIG. 8). In the Bth mice, hearing loss was largely due to dysfunctional inner hair cells, in contrast to Pmca2 mice where outer hair cells are affected. Combining Pmca2 and Tmc1 studies, it was demonstrated that this approach is suitable to both inner and outer hair cell related hearing loss. In human the same Tmc1 mutation (M412K) has been reported in a multi-generation family (Zhao Y. et al. PLoS ONE, 9(5), e97064. http://doi.org/10.1371/journal- .pone.0097064). This study has potential to be developed as a treatment to be applied to those patients as a new therapy.

Example 3: Rescue of Hearing Loss by Cas9/gRNA Delivery In Vivo and CRISPR Mediated Gene Editing in a Genetic Deaf Mouse Model To use liposomal formulation that complexes Cas9 with gRNA for CRISPR mediated gene editing as a potential treatment for genetic deafness, a rescue effect on Pmca2 deafness mouse mutant was studied. Pmca2 is a plasma membrane $Ca^{2+}$ pump that is highly expressed in the inner ear hair cells, with the function that actively pumps out $Ca^{2+}$ that enters hair cells during signal mechanoelectrical transduction during hearing and vestibular function. PMCA2 mutation has been shown to increase hearing loss severity human (M Schultz et al., "Modification of Human Hearing Loss by Plasma-Membrane Calcium Pump PMCA2," *N Engl J Med* 352, no. 15 (Apr. 14, 2005): 1557-64, doi: 10.1056/NEJMoa043899). In the mouse mutant (Oblivion) with a point mutation (S877F), severe to profound (i.e. complete) hearing loss is observed in heterozygous and homozygous mice (Spiden et al., *PLoS Genetics* 4, e1000238-e1000238.2008). This mouse mutant thus serves as an excellent model to determine if the Cas9/gRNA approach can be used to disrupt the Pmca2 mutation in heterozygous mice for hearing recovery, with implication to reduce hearing loss in human.

To study the hearing rescue effect, 12 guide RNAs were designed, 4 of which targeted the mutation. Following lipofectamine 2000 formulation that complexes Cas9 with each gRNA, the complex was injected into postnatal day 3 (P3) mouse cochleas. Both mouse mutants and wildtype control mice were injected. For each mouse right ear was injected and the left ear was uninjected. Three weeks or four weeks after injection, acoustic Auditory brainstem response (ABR) and distortion product otoacoustic emissions (DPOAE) tests were performed.

For ABR and DPOAE tests, injected mice of either sex were anesthetized with xylazine (10 mg/kg, i.p.) and ketamine (100 mg/kg, i.p.). ABR and DPOAE were performed as previously described (Huang et al., 2013). ABR measures the auditory pathway from hair cells to brain; whereas DPOAE measures primarily outer hair cell function. By their combination it could be inferred if the hearing defects are of hair cells or central pathway deficiency.

At three weeks after injection, in the heterozygous Pmca2 mice, uninjected inner ears had profound hearing loss as shown by ABR and DPOAE. In the Cas9/gRNA-Pmca-2.4 (with the guide RNA 2.4) injected ears, significant hearing recovery in frequencies of 16, 22.64, 32 and 45.24 kHz by ABR was observed. By DPOAE, significant recovery in frequencies from 16 to 45.24 kHz was detected in the Cas9/gRNA-Pmca-2.4 injected inner ear, corresponding to ABR recovery. Recovery of DPOAE is an indication of restoration of hair cell function. To study long-term effect of hearing recovery, a hearing study was performed four weeks after injection and observed similar hearing recovery. The hearing study is continued at 6, 12 and 26 weeks after injection. In addition to the uninjected control ears, Pmca2 heterozygous mice injected with Cas9 complexed with other Pmca2 guide RNAs were also studied. No hearing recover was detected either by ABR or DPOAE (data not shown). Thus guide RNA Pmca2-2.4 complexed with Cas9 induced sequence specific gene editing of Pmca2 mutation, leading to significant improvement of hearing.

To study potential toxicity associated with Cas9/gRNA delivery, Cas9/gRNA-Pmca-2.4 was injected into P3 wildtype (WT) mice and performed hearing study 3 weeks after injection. Slight elevation was observed in ABR and DPOAE at the highest frequency (45.24 kHz), but not in any other frequencies. Thus Cas9/gRNA-Pmca-2.4 complex does not cause additional damage to healthy hair cells or inner ear function. All together the study demonstrates that Cas9/gRNA that targets Pmca2 mutation in hair cells restores hearing in otherwise complete deaf mouse mutants. The similar strategy thus can be applied to human deaf patients with Pmca2 mutations to improve or restore hearing.

Figure 9:
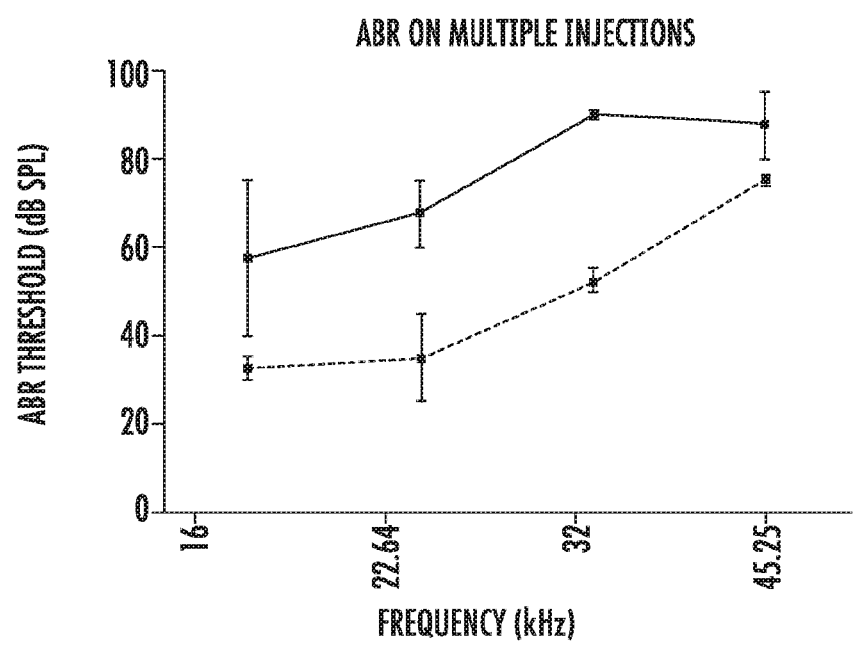
FIG. 9 is a graph showing that in four weeks after multiple injections, ABR in the Cas9/gRNA-Pmca2-2.4 injected inner ears show dramatic hearing restoration at 16, 22.64, 32 and 45.24 kHz comparing to the uninjected control ears. Hearing restoration at 16, 22.64 and 32 kHz are improved by 40 dB.

The hearing recovery in the Cas9/gRNA-Pmca-2.4 injected ear was not uniform across all frequencies (e.g. no recovery in 8 kHz). Further the recovery was uneven as better recovery was seen at the highest frequency of 45.24 kHz. This is likely due to the surgical procedure used only allowed for access to primarily the base of the cochlea, which is responsible for high-frequency hearing. The lack of recovery at the low frequency is likely due to the insufficient diffusion of Cas9/gRNA complex to the apical region of the cochlea. To test the hypothesis, additional experiments by multiple injections were performed in the Pmca2 mice over 6 days. By four weeks much greater hearing recovery was observed (40 dB) covering a majority of frequencies from 16 to 45.24 kHz (FIG. 9). The mouse inner ear is extremely small in size, about 1/50th of the size of human inner ear. While the mouse inner ear presents a surgical challenge in protein delivery, it is anticipated that in human inner ear the delivery would be considerably easier. Thus multiple injections result in greatly improved hearing restoration across most frequencies.

One of the most important applications of the technology is the ability to deliver the Cas9/gRNA complex in mature mammalian inner ear. The first set of experiments were conducted and showed that when injected into P9 mouse cochlea, a similar hearing rescue effect was observed (data not shown).

The work demonstrates the utility of direct Cas9/gRNA delivery into mammalian inner ear hair cells in vivo in disruption of mutations that leads to functional recovery of hearing. As 20% of genetic deafness is due to dominant mutations, this method can be tailored to target those mutations to restore hearing.

The most common form of deafness is recessive, for which repair of mutations will be needed for hearing restoration. One of the most common forms of deafness in human is age-related hearing loss (ARHL) or presbycusis, affecting over hundreds of millions of people worldwide. While the major mechanisms underlying ARHL is unknown, it is likely that genes will be identified with mutations or polymorphisms that make hair cells vulnerable to aging. Under this condition, the Cas9/gRNA could be applied to disrupt or repair the mutations/polymorphisms, to restore or slow down the progression of hearing loss. While the method currently targets hair cells, modifications will be made so that the method can be used to target inner ear cell types such as supporting cells, strial vascular and neurons, in which similar gene editing can be achieved for functional recovery of hearing. Finally many recessive genetic deafness is congenital, by the time of birth, simple gene editing may not be sufficient to restore cell function or hearing due to degeneration of the cell types. However it is possible to combine regeneration of the cell types with gene editing, to produce new cells while correcting mutations. These combinations can be applied to restore hearing in patients suffering from hearing loss due to different causes.

Example 4: Protein Delivery into the Inner Ear

The goal of this study was to use protein-mediated delivery system to deliver the biological proteins directly inner ear cell types with functional consequences. With this method, the proteins delivered have specific functions, and the effect is transient. Further, delivery of native protein lessens any potential immune response.

As cell surface is cationic (positively charged), it has been demonstrated that, by changing amino acids, GFP (green fluorescent protein) can be modified to be highly charged (both positively and negatively, named supercharged protein), which enables the supercharged GFP to enter cells. As a result, the super-charged GFP (s-GFP) can be used as vehicle to link and deliver other proteins into cells with biological effect in vitro and in vivo. This has been demonstrated in mouse retina in which s-GFP carrying Cre recombinase (s-GFP-Cre) was delivered that resulted in expression of reporter gene in retinal cells. The s-GFP used as (−30)-GFP, a negatively charged GFP protein.

Figure 10A:
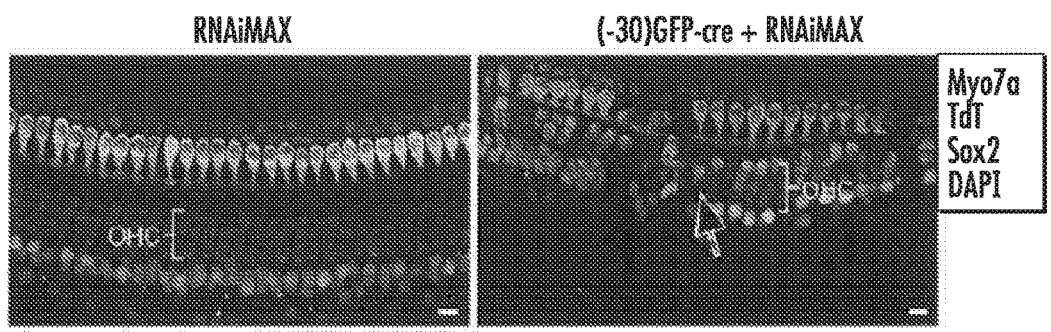
FIGS. 10A and 10B show the in vivo delivery of Cre recombinase to hair cells in the mouse inner ear.
Figure 10B:
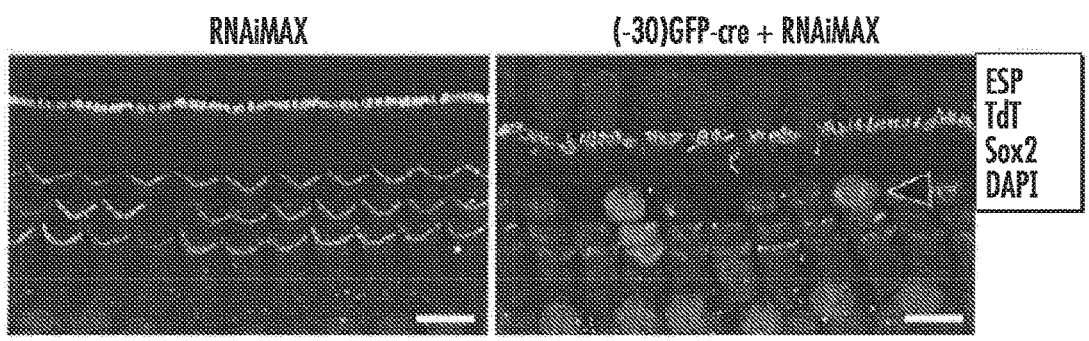
Figure 11A:
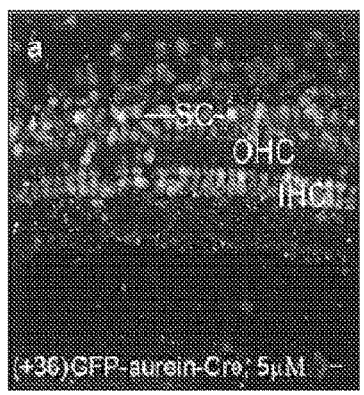
FIGS. 11A-11E show the high efficiency of protein delivery mediated by aurein in the inner ear in vivo. Injection of (+36)GFP-aurein-Cre with different concentrations to Rosa-tdTf$^f$ mouse cochlea resulted in tdT labeling in cochlear cell types with different efficiencies.
Figure 11B:
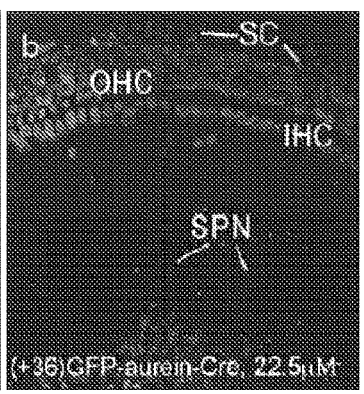
Figure 11C:
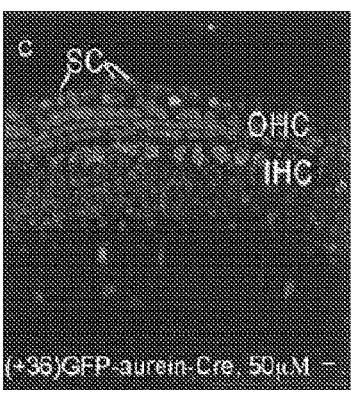
Figure 11D:
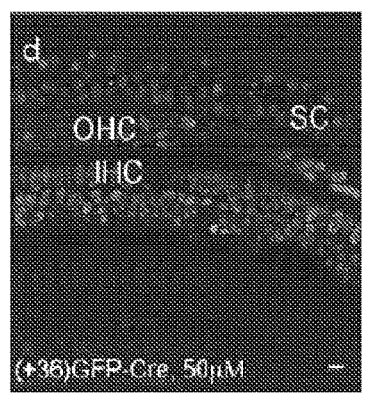
Figure 11E:
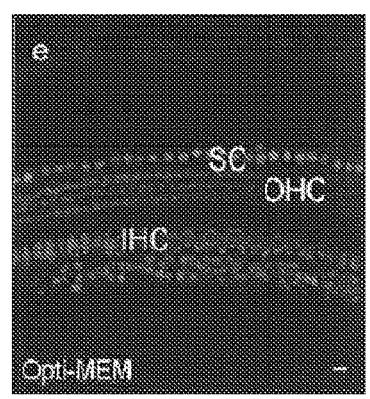
Figure 12:
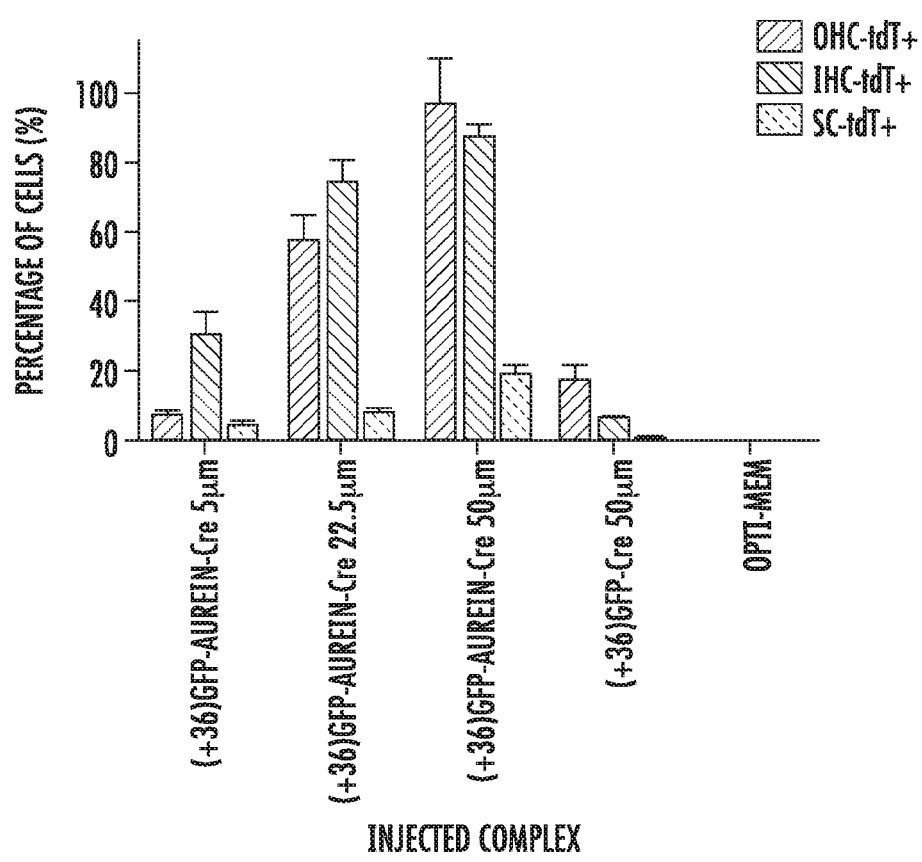
FIG. 12 shows the high efficiency of aurein mediated protein delivery in the mammalian inner ear. Comparison between different concentrations of (+36)GFP-aurein-Cre and control reveled that extremely high-efficient delivery of functional protein (Cre) with the aurein at 22.5 and 50 µM, respectively.

The use of (−30)-GFP protein and a new positively charged (+36)-GFP protein to carry Cre, (−30)-GFP-Cre and (+36)-GFP-Cre, was tested for injection into mouse cochlea in vivo. The mouse used was Rosa-tdTomato$^{f/f}$ in which functional Cre activity in the nuclei results in cells being labeled with tdT (red). It was shown that both (−30)-GFP-Cre and (+36)-GFP-Cre injections led to tdT expression in the cochlear hair cells. Near the injection site (base turn of cochlea), ~30% of hair cells became tdT-labeled (FIGS. 10A, 10B), The study demonstrated that supercharged GFP proteins can be used to delivery protein directly into inner ear hair cells with biological effect in nuclei.

It was next tested whether Aurein, an antimicrobial peptide, in combination with s-GFP, can serve as an effective carrier to deliver functional proteins into mouse inner ear cell types with high efficiency. (+36)-GFP-aurein-Cre was injected with different concentrations into P3 Rosa-tdT mouse inner ear by cochleostomy in vivo. The tissues were harvested 5 days later for immunolabeling to identify tdT$^+$ inner ear cell types. Overall it was found that cochlear hair cells were primarily labeled with tdT, with additional tdT labeling in supporting cells and in spiral ganglion neurons. At low concentrations of 5 µM, few IHC and some supporting cells (SC) were tdT$^+$. At 22.5 µM, 58% of OHC and 75% of IHC, as well as 8% of SC were tdT$^+$. At the highest 50 µM, 96% of OHC, 88% of IHC and 19% of SC were tdT$^+$. Some spiral ganglion neurons were also tdT at 22.5 and 50 µM (FIGS. 11A-11E and FIG. 12). There was slight cell toxicity associated with the highest concentration of 50 µM. It was found that 20% of IHC loss 8% of OHC in the injected animals, whereas at lower concentrations of 5 and 22.5 µM no cell loss was detected.

The study demonstrated that functional proteins including nuclear proteins can be conjugated with supercharged protein (+36)GFP fused with aurein. The protein complex was directly injected into mammalian inner ear that leads to uptake by a wide range of inner ear cell types. The protein delivered was properly localized in the nuclei and had the specific biological function in cleaving floxP sites on the DNA sequence, to activate tdTomato in the inner ear cells with high efficiency.

The delivery system can be used to study protein functions, inner ear regeneration for hearing recovery, hearing protection, and gene editing to correct genetic deafness by genome-editing proteins.

Example 5: Characterization of a Peptide that Enhances Endosomal Escape of Delivered Proteins In Vitro and In Vivo In this study, aurein 1.2 (GLFDIIKKIAESF; SEQ ID NO: 34) was discovered as a peptide that enhances the endosomal escape of a variety of cargo fused to +36 GFP. The structure-function relationships were elucidated within aurein 1.2 using alanine scanning and mutational analysis. Results from three independent delivery assays confirmed that treatment of mammalian cells with cargo proteins fused to aurein 1.2-+36 GFP result in more efficient cytosolic delivery than the same proteins fused to +36 GFP alone. The ability of aurein 1.2 to enhance non-endosomal protein delivery in vivo is also described. Cre recombinase enzyme was delivered into hair cells in the cochlea (inner ear) of live mice with much greater (>20-fold) potency when fused with aurein 1.2 than in the absence of the peptide. These results together provide a simple molecular strategy for enhancing the cytosolic delivery of proteins in cell culture and in vivo that is genetically encoded, localized to cargo molecules, and does not require global treatment with cytotoxic small molecules.

Materials and Methods

Expression and Purification of Proteins.

*E. coli* BL21 STAR (DE3) competent cells (Life Technologies) were transformed with pET29a expression plasmids. Colonies from the resulting expression strain was directly inoculated in 1 L of Luria-Bertani (LB) broth containing 100 µg/mL of ampicillin at 37° C. to OD$_{600}$=~1.0. Isopropyl β-D-1-thiogalactopyranoside (IPTG) was added at 0.5 mM to induce expression and the culture was moved to 20° C. After ~16 h, the cells were collected by centrifugation at 6,000 g and resuspended in lysis buffer (Phosphate buffered saline (PBS) with 1 M NaCl). The cells were lysed by sonication (1 sec pulse-on, 1 sec pulse-off for 6 min, twice, at 6 W output) and the soluble lysate was obtained by centrifugation at 10,000 g for 30 min.

The cell lysate was incubated with His-Pur nickel-nitrilo-acetic acid (Ni-NTA) resin (Thermo Scientific) at 4° C. for 45 min to capture His-tagged protein. The resin was transferred to a 20-mL column and washed with 20 column volumes of lysis buffer plus 50 mM imidazole. Protein was eluted in lysis buffer with 500 mM imidazole, and concentrated by Amicon ultra centrifugal filter (Millipore, 30-kDa molecular weight cut-off) to ~50 mg/mL. The eluent was injected into a 1 mL HITRAP SP HP column (GE Healthcare) after dilution into PBS (5-fold). Protein was eluted with PBS containing a linear NaCl gradient from 0.1 M to 1 M over five column volumes. The eluted fractions containing protein were concentrated to 50 µM as quantified by absorbance at 488 nm assuming an extinction coefficient of 8.33×10$^4$ M$^{-1}$ cm$^{-1}$ as previously determined (McNaughton, B. R.; et al. *Proceedings of the National Academy of Sciences* 2009, 106, 6111), snap-frozen in liquid nitrogen, and stored in aliquots at −80° C.

Cell Culture.

All cells were cultured in Dulbecco's modification of Eagle's medium (DMEM w/glutamine, Gibco) with 10% fetal bovine serum (FBS, Gibco), 5 I.U. penicillin, and 5 g/mL streptamycin. All cells were cultured at 37° C. with 5% $CO_2$.

Peptide Synthesis.

Peptides were ordered from ChinaPeptides Co., LTD, each 4 mg, purity >90%. HPLC and MALDI data were provided with lyophilized peptides. Peptides were resuspended in DMSO to a final concentration of 10 mM.

Sortase Conjugation.

All reactions were performed in 100 mM Tris buffer (pH 7.5) with 5 mM $CaCl_2$ and 1M NaCl. For peptide conjugation to the N-terminus of GGG-+36-GFP, 20 μM of protein with N-terminal Gly-Gly-Gly was incubated with 400 μM of peptide with C-terminal LPETGG (SEQ ID NO: 89) and 1 μM eSrtA for 2 h at room temperature in a 50 μL reaction. The unreacted peptides were removed through spin filtration with an Amicon Ultra-0.5 Centrifugal Filter Unit (Millipore, 30-kDa molecular weight cut-off). The reaction mixture was washed twice with 500 μL of buffer each time to a final concentration of 50 μL. Conjugation efficiency was determined through LC-MS (Agilent 6220 ESI-TOF) using protein deconvolution through MaxEnt (Waters) by comparing relative peak intensities.

For conjugation of $GGGK^{Dex}$ (SEQ ID NO: 99) to +36-GFP-LPETG-$His_6$ ("LPETG-$His_6$" disclosed as SEQ ID NO: 100), 10 μM of protein was incubated with 400 μM of peptide and 2 μM eSrtA at room temperature. The reaction was quenched with 10 mM ethylenediaminetetraacetic acid (EDTA) after 2 h. For aurein 1.2-+36-GFP-LPETG-$His_6$ ("LPETG-$His_6$" disclosed as SEQ ID NO: 100), a N-terminal $His_6$-ENLYFQ (SEQ ID NO: 101) was added to prevent sortase reaction with the N-terminal glycine of aurein 1.2. The N-terminal tag was removed with 200 μM TEV protease at 4° C. for 16 h to release the native N-terminal sequence of aurein 1.2-+36-GFP. Successful conjugation of $GGGK^{Dex}$ (SEQ ID NO: 99) removes the C-terminal $His_6$ tag (SEQ ID NO: 98) and allows for purification through reverse Ni-NTA column. Unreacted protein binds to the Ni-NTA, and the unbound protein was collected and concentrated as described above.

Plasmid Transfection.

Plasmid DNA was transfected using Lipofectamine 2000 (Life Technologies) according the manufacturer's protocol. Synthesis of Dexamethasone-21 Thiopropionic Acid (SDex).

Synthesis of dexamethasone-21-mesylate was performed as previously described (Simons, S. S.; et al. *J Org Chem* 1980, 45, 3084; Dunkerton, L. V.; et al. *Steroids* 1982, 39, 1). 2 g of dexamethasone stirring in 38 mL anhydrous pyridine under nitrogen was reacted with 467.2 mg methanesulfonyl chloride (1.2 eq.) on ice for 1 h, after which another 311 methanesulfonmethanesulfonyl chloride was added and allowed to react overnight (16 h) on ice. Next, the reaction was added to 800 mL of ice water and Dexamethasone-21-Mesylate (Dex-21-OMs) formed a white precipitate. The slurry was filtered and the precipitate washed with 800 mL of ice water, dried under high vacuum overnight and quantified by LC-MS (m/z 471.19 Da, 83% yield).

Dexamethasone-21-thiopopionic acid ($S^{Dex}$) was prepared as previously described (Kwon, Y. U.; Kodadek, T. *J Am Chem Soc* 2007, 129, 1508). 2.05 g of Dex-21-OMs was added to 2 eq. thiopropionic acid and 4 eq. triethylamine stirring in anhydrous acetone at room temperature overnight. The following morning, the reaction was added to 800 mL of ice water and acidified with 1N HCl until $S^{Dex}$, visible as an off-white solid, precipitation was complete. The mixture was filtered, washed with 800 mL ice cold water acidified to pH 1 with HCl, dried under high vacuum overnight and analyzed by LC-MS (m/z 481.21 Da, 63% yield).

Synthesis and Purification of $GGGK^{Dex}$ (SEQ ID NO: 99). $GGGK^{Dex}$ (SEQ ID NO: 99) was synthesized on Fmoc-Lys (Mtt)-Wang resin (BACHEM, D-2565) using microwave acceleratin (MARS, CEM). Coupling reactions were performed using 5 equivalents of Fmoc-Gly-OH (Novabiochem, 29022-11-5), 5 equivalents of PyClock (Novabiochem, 893413-42-8) and 10 equivalents of diisopropylethylamine (DIEA) in N-methylpyrrolidone (NMP). Fmoc groups were removed using 25% piperidine in NMP (efficiency quantified; $\varepsilon_{299}$=6234 $M^{-1}$ $cm^{-1}$ in acetonitrile) and Mtt groups were removed by incubating the Fmoc-GGGK (Mtt)-resin (SEQ ID NO: 99) with 2% trifluoroacetic acid (TFA) in dichloromethane (DCM) for 20 min, after which the resin was washed with 2% TFA in DCM until the characteristic yellow color emitting from the Mttcation subsided. After Mtt removal, $S^{Dex}$—COOH (Dex-21-thiopropinonic acid) was coupledto the NE of the lysine sidechain by incubating the Fmoc-GGGK-resin (SEQ ID NO: 99) with 2.5 eq. $S^{Dex}$—COOH, 2.5 eq. HATU, 2.5 eq. HOAt, 5 eq. DIEA and 5 eq. 2,6-lutidine in 2.5 mL NMP overnight, at room temperature, on an orbital shaker. After $S^{Dex}$-labeling, Fmoc-$GGGK^{Dex}$-resin (SEQ ID NO: 99) was washed thoroughly with NMP and DCM, the N-terminal Fmoc was removed using 25% piperidine in NMP, and crude peptides were dissociated from the resin by incubating the $GGGK^{Dex}$-resin (SEQ ID NO: 99) in a cleavage cocktail composed of 81.5% trifluoroacetic acid (TFA), 5% thioanisole, 5% phenol, 5% water, 2.5% ethanedithiol and 1% triisopropylsilane for 30 min at 38° C. Crude peptides were precipitated in 40 mL cold diethyl ether, resuspended in water, lyophilized and purified via reverse phase high-pressure liquid chromatography (HPLC) using a linear gradient of acetonitrile and water with 0.1% TFA across a C18 (VYDAC, 250 mm×10 mm ID) column. Purified peptides were lyophilized and stored at 4° C. Polypeptide identity was confirmed by mass spectrometry on a Waters QToF LC-MS, and purity was measured by analytical reverse-phase HPLC (Shimadzu Instruments) using a C18 column (Poroshell 120 SB-C18, 2.7 μm, 100 mm×3 mm ID, Agilent).

Image Processing for Primary Screen.

BSR.LNL.tdTomato cells were plated at 10,000 cells per well in black 384-well plates (Aurora Biotechnologies). Cells were treated with Cre fusion proteins diluted in serum-free DMEM 24 h after plating and incubated for 4 h at 37° C. Following incubation, the cells were washed three times with PBS+20 U/mL heparin. The cells were incubated a further 48 h in serum-containing media. Cells were fixed in 3% paraformaldehyde and stained with Hoescht 33342 nuclear dye. Images were acquired on an ImageXpress Micro automated microscope (Molecular Devices) using a 4× objective (binning 2, gain 2), with laser- and image-based focusing (offset–130 μm, range±50 μm, step 25 μm). Images were exposed for 10 ms in the DAPI channel (Hoechst) and 500 ms in the dsRed channel (tdTomato). Image analysis was performed using the cell-scoring module of MetaXpress software (Molecular Devices). All nuclei were detected with a minimum width of 1 pixel, maximum width of 3 pixels, and an intensity of 200 gray levels above background. Positive cells were evaluated for uniform signal in the dsRed channel (minimum width of 5 pixels, maximum width of 30 pixels, intensity >200 gray levels above background, 10 μm minimum stained area). In total, nine images were captured and analyzed per well, and 16 wells were treated with the same fusion protein. The primary screen was completed in biological triplicate.

Cre Delivery Assay.

Uptake and delivery assays for Cre fusion proteins were performed as previously described (Cronican, J. J.; et al. *ACS Chemical Biology* 2010, 5, 747). Briefly, proteins were diluted in serum-free DMEM and incubated on the cells in 48-well plates for 4 h at 37° C. Following incubation, the cells were washed three times with PBS+20 U/mL heparin. The cells were incubated a further 48 h in serum-containing media prior to trypsinization and analysis by flow cytometry. All flow cytometry were carried out on a BD Fortessa flow cytometer (Becton-Dickinson) using 530/30 nm and 610/20 nm filter sets. Toxicity for aurein 1.2 and citropin 1.3 validation assays was determined using CELLTITER-GLO assay (Promega) in 96-well plates following manufacturer protocol. Toxicity for alanine scan mutational analysis was determined with LIVE/DEAD fixable far-red dead cell stain (Life Technologies) with 635 nm laser and 670/30 nm filter.

GR-mCherry Translocation Assay.

One day prior to transfection 10,000 HeLa cells in 200 µL of DMEM (10% FBS, 1× Pen-Strep) were plated into single wells of a 96-well MATRICAL glass bottom microplate (MGB096-1-2-LG-L) and allowed to adhere overnight. The following day, cells were transfected with GRmCherry using LIPOFECTAMINE® 2000 technologies. Following transfection, cells were allowed to recover overnight in DMEM (+10% FBS). The following day, cells were treated with dexamethasone (Dex) or 1 µM Dex-protein conjugate in the presence or absence of inhibitor diluted into DMEM (without phenol red, +300 nM Hoescht33342). After 30 min, cells were washed twice with 200 µL of HEPES-Krebs-Ringer's (HKR) buffer (140 mM NaCl, 2 mM KCl, 1 mM $CaCl_2$, 1 mM $MgCl_2$, and 10 mM HEPES at pH 7.4), after which 100 µL of HKR buffer was overlaid onto the cells and images were acquired on a Zeiss Axiovert 200M epifluorescence microscope outfitted with Ziess AxiocammRM camera and an EXFO-Excite series 120 Hg arc lamp. The translocation ratio (the ratio of median GFP intensity in the nuclear and surrounding regions) for individual cells was measured using CELLPROFILER® as described 36. To examine the effect of endocytosis inhibitors, HeLa cells were pretreated for 30 min with DMEM (without phenol red) containing inhibitors (80 µM Dynasore, 5 mM MBCD, 50 µM EIPA, 200 nM bafilomycin or 200 nM wortmannin) at 37° C. for 30 min before incubation with Dex or Dex-protein conjugates.

BirA Translocation Assay.

One day prior to transfection, 100,000 HeLa cells in 1 mL of DMEM (10% FBS, 1×PenStrep) were plated into single wells of a 12-well tissue culture plate and allowed to adhere overnight. Cells were transfected with mCherry-AP fusion protein using LIPOFECTAMINE® 2000 technologies according to manufacture guidelines 24 h before protein treatment. Next day, transfected cells were treated for 1 h at 37° C. with +36 GFP-BirA or aurein 1.2-+36 GFP-BirA diluted in serum-free DMEM at 250 nM, 500 nM and 1 µM concentrations. 250 nM+36 GFP-BirA+100 µM chloroquine was also used as a positive control for endosomal escape. The cells were washed three times with PBS containing heparin to remove excess supercharged proteins that were not internalized. The cells were then treated with 100 µL of 10 µM biotin and 1 mM ATP in PBS for 10 min. The reaction was quenched with excess (10 µL of 8 mM) synthesized AP before cells were trypsinized and lysed. To verify that extracellular BirA was not generating signal during lysis, 1 µM+36 GFP-BirA or aurein 1.2-+36 GFP-BirA was added during the quench step to untreated wells. Cells were lysed with 100 µL of trypsin and lysed with QIASHREDDER columns (Qiagen). 30 µL of lysate was loaded onto 4-12% Bis-Tris Bolt gels in Bolt-MES buffer (Life Technologies) and ran for 20 min at 200 volts. Gels were transferred to PVDF membrane using IBLOT2 transfer system (Life Technologies). Biotinylation was measured through western blotting using the LI-COR quantitative infrared fluorescent antibodies and the Odyssey Imager detection system. To normalize for transfection and gel loading variables, the ratio of biotin signal to mCherry signal was used for comparison.

Cytosolic Fractionation Assay.

One day prior to fractionation, $4 \times 10^6$ HeLa cells were plated in 20 mL of DMEM (10% FBS, 1×PenStrep, no phenol red) in 175-$cm^2$ culture flasks and allowed to adhere for 15 hours. The following day, the media was removed from each flask and the cells were washed twice with clear DMEM (no FBS, no PenStrep, no phenol red). The media was replaced with 7 mL of clear DMEM containing +36 GFP or aurein 1.2-+36GFP at a concentration of 250 nM, 500 nM, or 1 µM. Several flasks were treated with clear DMEM to be used as negative controls and to generate calibration curves with the cytosolic extracts. The cells were incubated for 30 min at 37° C., 5% $CO_2$ after which they were washed three times with PBS. Using a cell-scraper, the cells were suspended in 5 mL of PBS, transferred into a 15 mL Falcon tube, and pelleted at 500 g for 3 min. The cells were resuspended in 1 mL PBS, counted using an automated cell counter (Auto T4, CELLOMETER®), and pelleted again at 500 g for 3 min. The cell pellet was resuspended in ice-cold isotonic sucrose (290 mM sucrose, 10 mM imidazole, pH 7.0 with 1 mM DTT, and COMPLETE™, EDTA-free protease inhibitor cocktail) and transferred to a glass test tube on ice. The cells were homogenized with an Omni TH homogenizer outfitted with a stainless steel 5 mm probe for three 30 s pulses on ice with 30 s pauses between the pulses. The homogenized cell lysate was sedimented at 350 Kg in an ultracentrifuge (TL-100; Beckman Coulter) for 30 min at 4° C. using a TLA 120.2 rotor. The supernatant (cytosolic fraction) was analyzed in a 96-well plate on a fluorescence plate reader (SYNERGY 2, BioTek, excitation=485+/−10 nm, emission=528+/−10 nm). The concentration of the protein conjugate in the cytosol was determined using a standard curve relating fluorescence to known protein concentrations. To generate the standard curve, known concentrations of +36 GFP and aurein 1.2-+36 GFP between 0.2 nM and 1 µM were added to cytosolic extracts of the untreated negative controls. For background subtraction, several wells containing cytosolic extracts from untreated cells were averaged, and this average was subtracted from each well.

Total Protein Delivery Assay.

One day prior to the experiment, 100,000 HeLa cells/well were plated in DMEM (10% FBS, 1x PenStrep, no phenol red) in 6-well plates and allowed to adhere for 15 hours. The following day, the media was removed from each well and the cells were washed twice with clear DMEM (no FBS, no PenStrep, no phenol red). The media was replaced with 1 mL of clear DMEM containing +36 GFP or aurein 1.2-+36 GFP at concentrations of 250 nM, 500 nM, or 1 µM. The cells were incubated for 30 min at 37° C., 5% $CO_2$ after which they were washed three times with PBS containing 20 U/mL heparin (Sigma) to remove surface-bound cationic protein. The cells were trypsinized for 5 min, pelleted in serum-containing DMEM for 3 min at 500 g, washed with 1 mL PBS, and pelleted again for 3 min at 500 g. The cell pellet was resuspended in 100 μL PBS. Flow cytometry was performed on a BD Accuri C6 Flow Cytometer at 25° C. Cells were analyzed in PBS (excitation laser=488 nm, emission filter=533+/−30 nm). At least 10,000 cells were analyzed for each sample. For background subtraction, wells were treated with clear DMEM only. The average of three untreated wells was subtracted from each +36 GFP conjugate-containing well.

Microinjection of Proteins to Mouse Inner Ear.

P1-2 Gt(ROSA)26Sor$^{tm14(CAG-tdTomato)Hze}$ mice were used for aurein 1.2-+36-GFP-Cre and +36-GFP-Cre injection. The Rosa26-tdTomato mice were from the Jackson Laboratory. Animals were used under protocols approved by the Massachusetts Eye & Ear Infirmary IACUC committee. Mice were anesthetized by hypothermia on ice. Cochleostomies were performed by making an incision behind the ear to expose the cochlea. Glass micropipettes held by a micromanipulator were used to deliver the complex into the scala media, which allows access to inner ear hair cells. The total delivery volume for every injection was 0.4 μL per cochlea and the release was controlled by a micromanipulator at the speed of 69 nL/min.

Immunohistochemistry and Quantification.

5 days after injection, the mice were sacrificed and cochlea were harvested by standard protocols (Sage, C.; et al. *Science* 2005, 307, 1114). For immunohistochemistry, antibodies against hair-cell markers (Myo7a) and supporting cells (Sox2) were used following a previously described protocol (Sage C et al., supra). To quantify the number of tdTomato positive cells after aurein 1.2-+36-GFP-Cre and +36-GFP-Cre, we counted the total number of inner and outer hair cells in a region spanning 100 μm in the apex, middle, and base turn of the cochlea.

Results

Figure 13A:
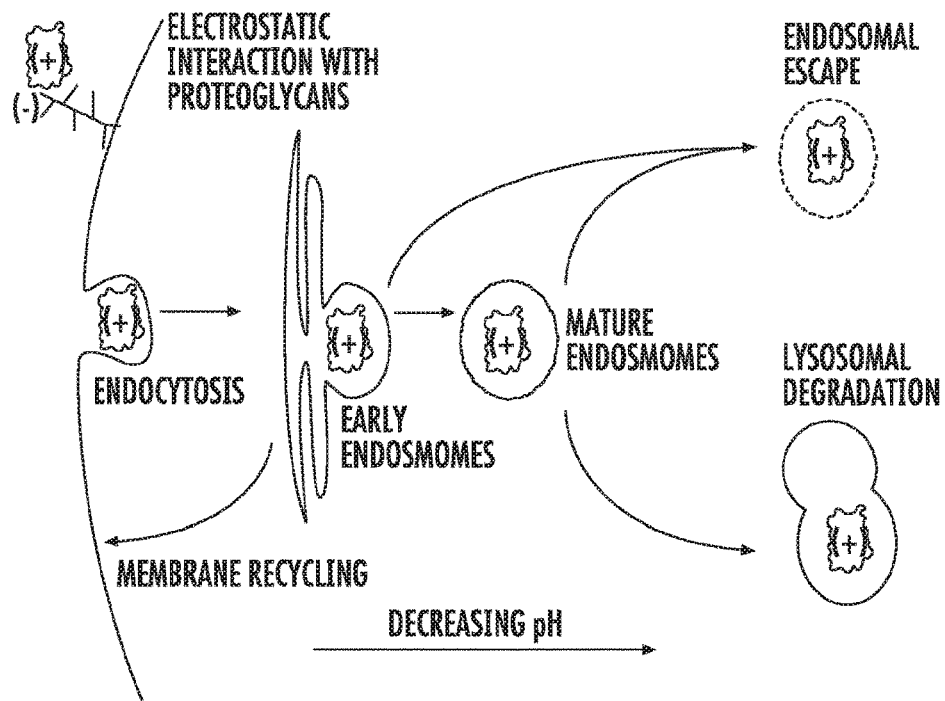
FIG. 13A is a schematic representation showing an overview of protein delivery in mammalian cells. Cationic macromolecules such as +36 GFP interact with anionic sulfated proteoglycans on the cell surface and are endocytosed and sequestered in early endosomes. The early endosomes can acidify into late endosomes or lysosomes. Alternatively, early endosomes may be trafficked back to the cell surface as part of the membrane-recycling pathway. To access the cytoplasm, an exogenous cationic protein must escape endosomes before it is degraded or exported.
Figure 13B:
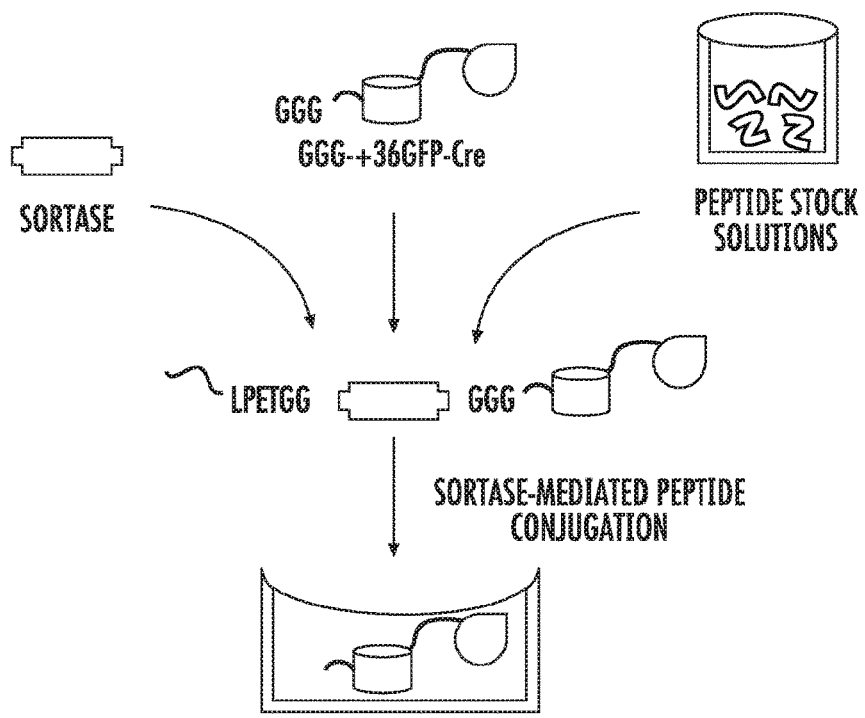
FIG. 13B is a schematic representation showing the sortase-mediated conjugation of peptides with +36 GFPCre recombinase prior to screening. Sortase was used to conjugate synthetic peptides containing a C-terminal LPETGG (SEQ ID NO: 89) with expressed +36 GFP-Cre containing an N-terminal GGG. The resulting peptide-LPETGGG-+36 GFP-Cre fusion proteins ("LPETGGG" disclosed as SEQ ID NO: 96) have the same chemical composition as expressed recombinant proteins, but are more easily assembled.

Preparation of Antimicrobial Peptide (AMP) Conjugates of Supercharged GFP-Cre Fusion Protein:

AMPs from the Antimicrobial Peptide Database (Wang, Z.; Wang, G. *Nucleic acids research* 2004, 32, D590) that are ≤25 amino acids long (to facilitate their preparation and conjugation to +36 GFP), lack post-translational modifications, and are not known to be toxic to mammalian cells. Based on these criteria, 36 AMPs were identified ranging from 9 to 25 amino acids in length (Table 1). Each of the peptides was synthesized on solid phase with an LPETGG (SEQ ID NO: 89) sequence appended to their C-terminus to enable sortase-catalyzed conjugation (Chen, I.; et al. *Proceedings of the National Academy of Sciences* 2011, 108, 11399) (FIG. 13B). Assembly of proteins using sortase proved more amenable to rapid screening than the construction and expression of the corresponding fusions, especially since several AMP fusions do not express efficiently in *E. coli*.

The peptides were conjugated to purified GGG-(+36 GFP)-Cre using the previously described evolved sortase A enzyme (eSrtA) (Chen, I.; et al. *Proceedings of the National Academy of Sciences* 2011, 108, 11399). Sortase catalyzes the transpeptidation between a substrate containing the C-terminal LPETGG (SEQ ID NO: 89) and a substrate containing an N-terminal glycine to form a native peptide bond linkage and a protein identical to the product of translational fusion.

TABLE 1

List of peptides chosen from the Antimicrobial Peptide Database (APD)

| Label | APD number | Sequence | Conjugation efficiency |
|---|---|---|---|
| A | AP00408 | FLFPLITSFLSKVL (SEQ ID NO: 36) | 55% |
| B | AP00405-11 | FISAIASMLGKFL (SEQ ID NO: 37) | 70% |
| C | AP00327 | GWFDVVKHIASAV (SEQ ID NO: 38) | – |
| D | AP01434 | PFGSVLKLIPKIL (SEQ ID NO: 39) | – |
| E | AP00013 | GLFDIIKKIAESF (SEQ ID NO: 34) | 77% |
| F | AP00025 | HGVSGHGQHGVHG (SEQ ID NO: 40) | 20% |
| G | AP00094 | FLPLIGRVLSGIL (SEQ ID NO: 41) | – |
| H | AP00012 | GLFDIIKKIAESI (SEQ ID NO: 42) | 28% |
| I | AP00014 | GLLDIVKKVVGAFGSL (SEQ ID NO: 43) | – |
| J | AP00015 | GLFDIVKKVVGALGSL (SEQ ID NO: 44) | 13% |
| K | AP00016 | GLFDIVKKVVGAIGSL (SEQ ID NO: 45) | – |
| L | AP00017 | GLFDIVKKVVGTLAGL (SEQ ID NO: 46) | 18% |
| M | AP00018 | GLFDIVKKVVGAFGSL (SEQ ID NO: 47) | – |
| N | AP00019 | GLFDIAKKVIGVIGSL (SEQ ID NO: 48) | – |
| O | AP00020 | GLFDIVKKIAGHIAGSI (SEQ ID NO: 49) | – |
| P | AP00021 | GLFDIVKKIAGHIASSI (SEQ ID NO: 50) | – |
| Q | AP00022 | GLFDIVKKIAGHIVSSI (SEQ ID NO: 51) | – |
| R | AP00101 | FVQWFSKFLGRIL (SEQ ID NO: 52) | 51% |
| S | AP00351 | GLFDVIKKVASVIGGL (SEQ ID NO: 53) | 11% |
| T | AP00352 | GLFDIIKKVASVVGGL (SEQ ID NO: 54) | – |
| U | AP00353 | GLFDIIKKVASVIGGL (SEQ ID NO: 35) | 4% |
| V | AP00567 | VWPLGLVICKALKIC (SEQ ID NO: 55) | 4% |
| W | AP00597 | NFLGTLVNLAKKIL (SEQ ID NO: 56) | 34% |
| X | AP00818 | FLPLIGKILGTIL (SEQ ID NO: 57) | 14% |

TABLE 1-continued

List of peptides chosen from the Antimicrobial Peptide Database (APD)

| Label | APD number | Sequence | Conjugation efficiency |
|---|---|---|---|
| Y | AP00866 | FLPIIAKVLSGLL (SEQ ID NO: 58) | 86% |
| Z | AP00870 | FLPIVGKLLSGLL (SEQ ID NO: 59) | – |
| AA | AP00875 | FLSSIGKILGNLL (SEQ ID NO: 60) | 88% |
| AB | AP00898 | FLSGIVGMLGKLF (SEQ ID NO: 61) | 70% |
| AC | AP01211 | TPFKLSLHL (SEQ ID NO: 62) | 81% |
| AD | AP01249 | GILDAIKAIAKAAG (SEQ ID NO: 63) | 20% |
| AE | AP00013-G | LFDIIKKIAESF (SEQ ID NO: 64) | 63% |
| AF | AP00013-2x | LFDIIKKIAESGFLFDIIKKIAESF (SEQ ID NO: 65) | – |
| AG | AP00722-75 | GLLNGLALRLGKRALKKIIKRLCR (SEQ ID NO: 66) | – |
| AH | His13 | GHHHHHHHHHHHHH (SEQ ID NO: 67) | – |
| AI | AP00512 | FKCRRWQWRM (SEQ ID NO: 68) | 42% |
| AJ | AP00553 | KTCENLADTY (SEQ ID NO: 69) | – |

Peptides were synthesized with a C-terminal LPETGG tag (SEQ ID NO: 89) to enable conjugation with an evolved sortase (eSrtA). Conjugation efficiencies were calculated based on LC-MS results using peak abundance as determined through MaxEnt protein deconvolution.

The efficiency of eSrtA-mediated conjugation varied widely among the peptides. Of the 36 peptides chosen for screening, 20 showed detectable (4% to 88%) sortase-mediated conjugation to +36 GFP-Cre, as observed by LC-MS, to generate desired peptide-LPETGGG-(+36 GFP)-Cre fusion proteins ("LPETGGG" disclosed as SEQ ID NO: 96). (Table 1). Unreacted peptide was removed by ultrafiltration with a 30-kD molecular weight cut off membrane.

Primary Screen for Endosomal Escape.

The ability of each peptide-(+36 GFP)-Cre recombinase fusion was assayed when added to culture media to effect recombination in BSR.LNL.tdTomato cells (Cronican, J. J.; et al. *ACS Chemical Biology* 2010, 5, 747), a hamster kidney cell line derived from BHK-21. Because Cre recombinase must enter the cell, escape endosomes, enter the nucleus, and catalyze recombination to generate tdTomato fluorescence, this assay reflects the availability of active, non-endosomal recombinase enzyme that reaches the nucleus. As a positive control, cells were treated with +36 GFP-Cre and chloroquine, a known endosome-disrupting small molecule (Dijkstra, J.; et al. *Biochimica et Biophysica Acta (BBA)-Molecular Cell Research* 1984, 804, 58).

Figure 14:
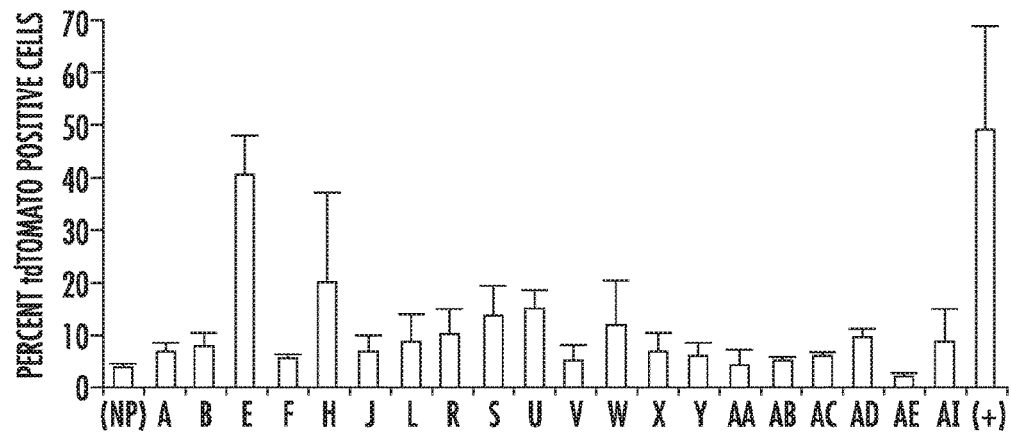
FIG. 14 is a graph showing a primary screen for cytosolic delivery of Cre recombinase in BSR.LNL.tdTomato cells. Initial screen of 20 peptide-(+36 GFP)-Cre conjugated proteins. Cytosolic Cre delivery results in recombination and tdTomato expression. The percentage of tdTomato positive cells was determined by fluorescence image analysis. 250 nM+36 GFP-Cre was used as the no-peptide control (NP), and addition of 100 µM chloroquine was used as the positive control (+). Cells were treated with 250 nM protein for 4 h in serum-free DMEM. Cells were washed and supplanted with full DMEM and incubated for 48 h. Error bars represent the standard deviation of three independent biological replicates.

The reporter BSR.LNL.tdTomato cells were incubated with 250 nM of each peptide-(+36 GFP)-Cre protein in serum-free media. In the absence of any conjugated peptide, treatment of reporter cells with 250 nM +36 GFP-Cre protein resulted in 4.5% of the cells expressing tdTomato, consistent with previous reports 18. The same concentration of protein incubated with 100 µM chloroquine as a positive control resulted in an average of 48% recombined cells (FIG. 14). The results of chloroquine treatment varied substantially between independent replicates. As chloroquine is known to be toxic to cells above 100 µM, it was speculated that this variability arises from the small differences between chloroquine's efficacious and toxic dosages.

Ten of the screened peptide conjugates resulted in recombination efficiencies that were significantly above that of +36 GFP-Cre (FIG. 14). The most potent functional delivery of Cre was observed with aurein 1.2-+36 GFP-Cre (Table 1, entry E). Treatment with aurein 1.2-+36 GFP-Cre resulted in an average of 40% recombined cells, comparable to that of the chloroquine positive control (FIG. 14). To investigate the impact of differential conjugation efficiency on peptide performance, citropin 1.3 (Table 1, entry U), which displayed a moderate level of recombination and the lowest level of conjugation (4%), was compared to aurein 1.2, which has the highest level of recombination and also a high level of conjugation (77%).

Figure 15A:
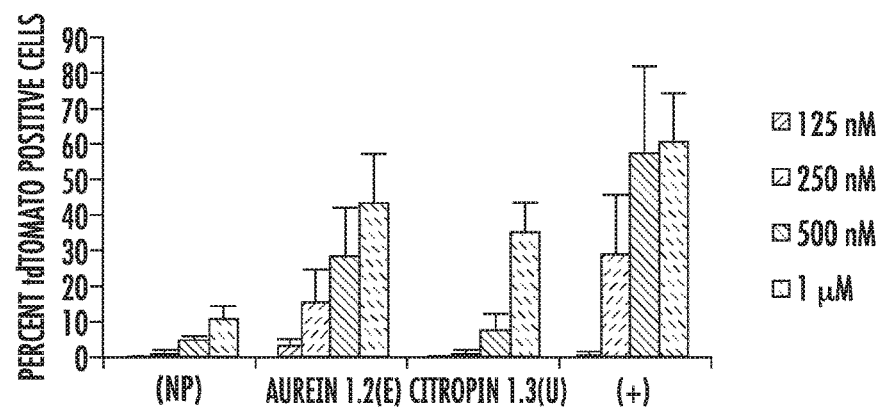
FIGS. 15A, 15B are graphs showing the efficacy and toxicity of recombinant expression fusions of aurein 1.2 ("E") and citropin 1.3 ("U").

Both aurein 1.2-+36 GFP-Cre and citropin 1.3-+36 GFP-Cre were cloned, expressed, and purified as fusion proteins. The recombination signal from treatment with 250 nM of expressed aurein 1.2-+36 GFP-Cre was 10.4-fold above that of +36 GFP-Cre. In contrast, treatment with 250 nM expressed citropin 1.3-+36 GFP-Cre did not induce any enhanced Cre delivery. When the treatment concentration was increased to 1 µM, aurein 1.2-+36 GFP-Cre and citropin 1.3-+36 GFP-Cre resulted in 3.8-fold and 3.0-fold higher recombination levels, respectively, than that of +36 GFP-Cre alone (FIG. 15A). These results evidence that while aurein 1.2 and citropin 1.3 both enhance the delivery of functional, non-endosomal +36 GFP-Cre protein at high concentrations, aurein 1.2 has greater efficacy than citropin 1.3 at lower concentrations.

Figure 15B:
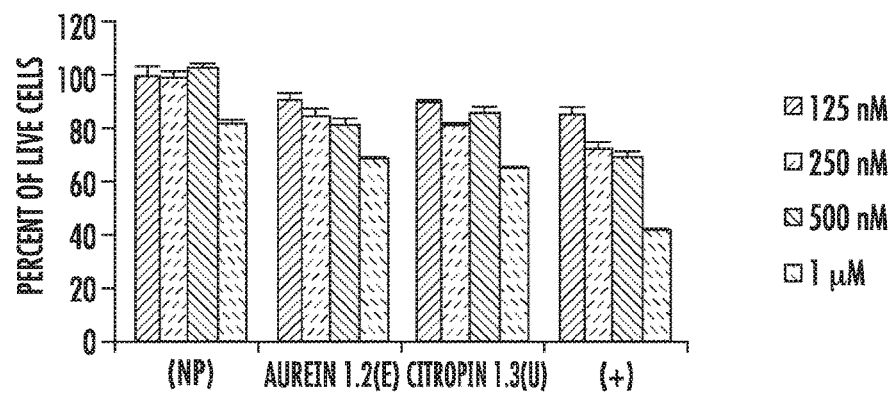

Next, the toxicity of each fusion protein was evaluated at a range of concentrations (125 nM to 1 µM) using an ATP-dependent cell viability assay at 48 h after treatment. For +36 GFP-Cre, it was observed that there was no cellular toxicity up to 1 µM treatment, which resulted in 85% viable cells. Cells treated with 250 nM recombinant aurein 1.2-+36 GFP-Cre and citropin 1.3-+36 GFP-Cre displayed 87% and 84% viability, respectively. Applying 1 µM treatments decreased cell viability to 70% and 66%, respectively (FIG. 15B). In light of its activity and low cytotoxicity at 250 nM, the ability of aurein 1.2 to enhance cytosolic protein delivery was characterized in depth.

Site-Directed Mutagenesis of Aurein 1.2.

Aurein 1.2 (GLFDIIKKIAESF; SEQ ID NO: 34) is a potent AMP excreted from the Australian tree frog, *Litoria aurea* (Rozek, T.; et al. *Rapid Communications in Mass Spectrometry* 2000, 14, 2002). Interestingly, citropin 1.3 (GLFDIIKKVASVIGGL; SEQ ID NO: 35) is a closely related peptide and is excreted from a different Australian tree frog, *Litoria citropa* (Wegener, K. L.; et al. *European journal of biochemistry/FEBS* 1999, 265, 627). While the properties of aurein 1.2 have been investigated for its anti-bacterial and anti-tumorigenic abilities ((Rozek, T.; et al. *Rapid Communications in Mass Spectrometry* 2000, 14, 2002), its ability to enhance endosomal escape or macromolecule delivery has not been previously reported. The free peptide is thought to adopt an amphipathic alpha helical structure in solution, but the length of the helix is too short to span a lipid bilayer (Balla, M.; Bowie, J. H.; Separovic, F. *European Biophysics Journal* 2004, 33, 109. Therefore it was theorized that aurein 1.2 disrupts membranes through a "carpet mechanism" in which peptides bind to the membrane surface in a manner that allows hydrophobic residues to interact with lipid tails and hydrophilic residues to interact with polar lipid head groups (Fernandez, D. I.; et al. *Physical Chemistry Chemical Physics* 2012, 14, 15739). Above a critical concentration, the peptides are thought to alter the curvature of the membrane enough to break apart the compartment.

TABLE 2

Site-directed mutagenesis of aurein 1.2

| Label | Sequence |
|---|---|
| Aurein 1.2 | GLFDIIKKIAESF (SEQ ID NO: 34) |
| G1A | ALFDIIKKIAESF (SEQ ID NO: 70) |
| L2A | GAFDIIKKIAESF (SEQ ID NO: 71) |
| F3A | GLADIIKKIAESF (SEQ ID NO: 72) |
| D4A | GLFAIIKKIAESF (SEQ ID NO: 73) |
| I5A | GLFDAIKKIAESF (SEQ ID NO: 74) |
| I6A | GLFDIAKKIAESF (SEQ ID NO: 75) |
| K7A | GLFDIIAKIAESF (SEQ ID NO: 76) |
| K8A | GLFDIIKAIAESF (SEQ ID NO: 77) |
| I9A | GLFDIIKKAAESF (SEQ ID NO: 78) |
| E11A | GLFDIIKKIAASF (SEQ ID NO: 79) |
| S12A | GLFDIIKKIAEAF (SEQ ID NO: 80) |
| F13A | GLFDIIKKIAESA (SEQ ID NO: 81) |
| K7H | GLFDIIHKIAESF (SEQ ID NO: 82) |
| K8H | GLFDIIKHIAESF (SEQ ID NO: 83) |
| E11H | GLFDIIKKIAHSF (SEQ ID NO: 84) |
| K7R | GLFDIIRKIAESF (SEQ ID NO: 85) |
| K8R | GLFDIIKRIAESF (SEQ ID NO: 86) |
| E11R | GLFDIIKKIARSF (SEQ ID NO: 87) |
| E11D | GLFDIIKKIADSF (SEQ ID NO: 88) |

An alanine scan was performed on aurein 1.2 to determine positions that tolerate mutation. Charged amino acids at tolerant positions were then replaced with histidines or other charged amino acids in an attempt to increase endosomal escape efficiency. All constructs were expressed as recombinant fusion proteins with +36 GFP-Cre.

Figure 16A:
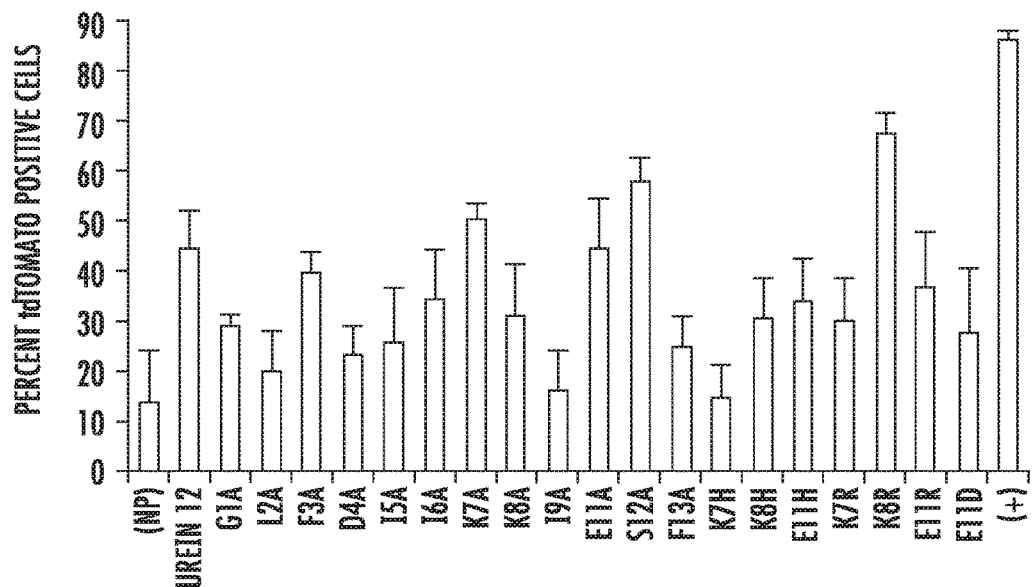
FIGS. 16A, 16B are graphs showing the activity and cytotoxicity of aurein 1.2 variants fused to +36 GFP-Cre (FIG. 16A). The percentage of tdTomato positive cells was determined by flow cytometry.
Figure 16B:
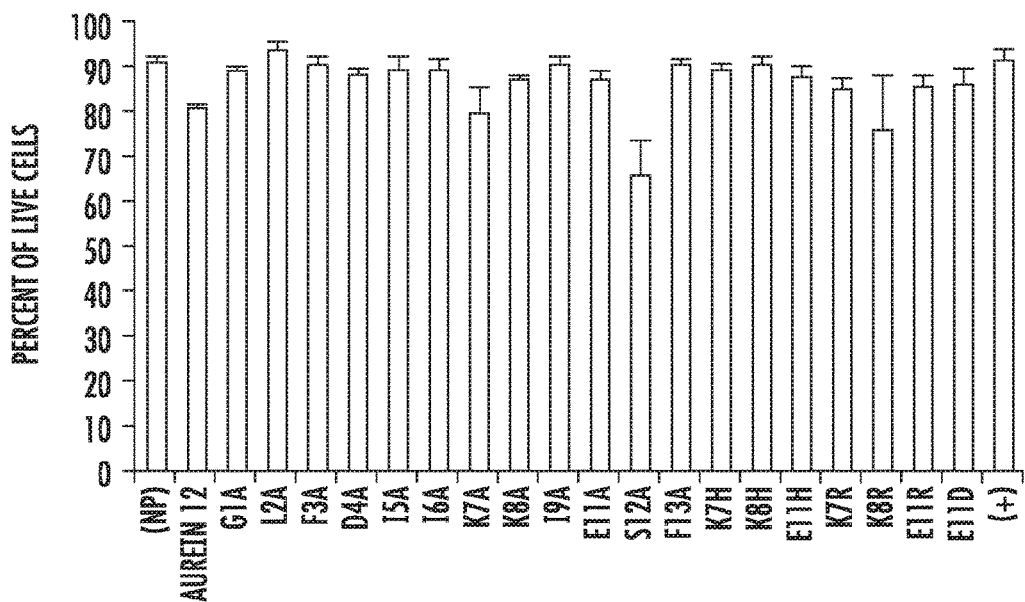

To identify the residues involved in enhancing non-endosomal protein delivery, an alanine scan of the 13 amino acid positions of aurein 1.2 was performed, by cloning, expressing, and purifying each alanine mutant of aurein 1.2-+36 GFP-Cre. The resulting fusion proteins were assayed in BSR.LNL.tdTomato reporter cells as described above (Table 2). Seven positions were moderately to highly intolerant of alanine substitution. Six positions retained >70% of the activity of unmutated aurein 1.2-+36 GFP-Cre (FIG. 16A). At each of these tolerant positions, which included three positions with charged residues (K7, K8, and E11 from Table 2), additional mutations were generated in an effort to improve activity. In total, 19 mutants of aurein 1.2 were generated and tested using the Cre recombination assay. Two of the aurein variants, K8R and S12A, exhibited potentially improved overall recombination efficiency but also increased toxicity at 250 nM (FIG. 16B). Given this increase in toxicity, it was decided to focus on the original peptide, aurein 1.2, and proceeded to characterize its potency through a series of complementary secondary assays.

Independent Assays of Endosomal Escape.

Figure 17A:
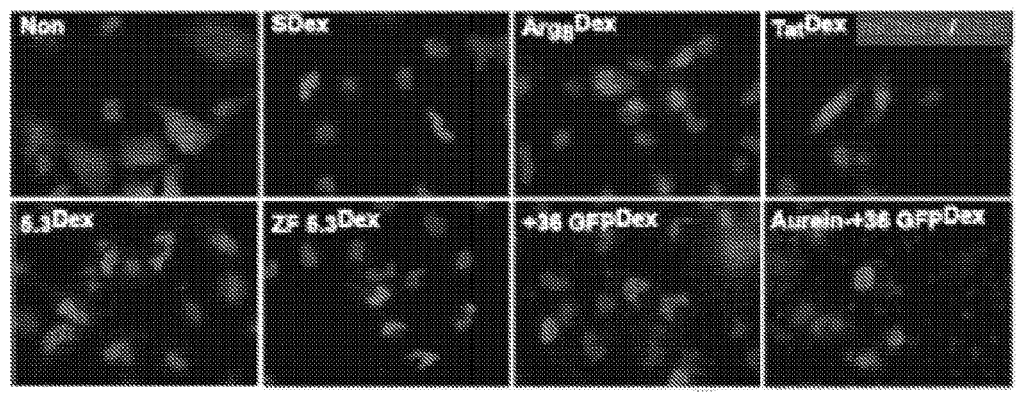
FIGS. 17A-17D show the ability of +36 GFP and aurein 1.2-+36 GFP dexamethasone-conjugates to reach the cytosol and activate GR translocation.
Figure 17B:
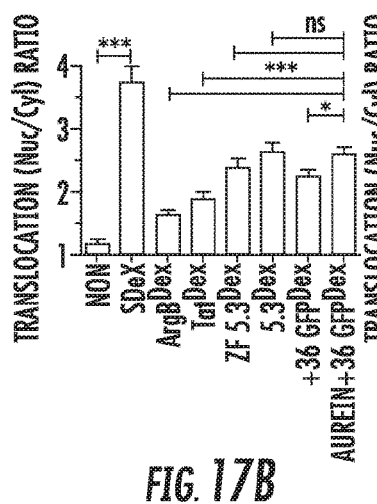

Although endosomal escape is widely considered to be the major bottleneck of cationic protein delivery (Sahay, G.; et al. *Nature Biotechnology* 2013, 31, 653), few assays quantify the ability of proteins to escape endosomes on a single-cell basis. To quantify cytosolic delivery of supercharged proteins in individual cells, a glucocorticoid receptor (GR) translocationassay (Yu, P.; Liu, B.; Kodadek, T. *Nat Biotech* 2005, 23, 746) was applied. In untreated HeLa cells expressing mCherry-labeled GR (GR-mCherry), the GR distributes nearly uniformly throughout the cell interior, resulting in a nuclear-to-cytoplasm translocation ratio (TR) of 1.17 (FIGS. 17A and 17B). Upon treatment with the cell-permeable glucocorticoid dexamethasone-21-thiopropionic acid ($S^{Dex}$) at a concentration of 1 μM for 30 min, GR-mCherry relocates almost exclusively to the nucleus, resulting in a TR of 3.77 (FIGS. 17A and 17B).

Dexamethasone conjugates of +36 GFP (+36 $GFP^{Dex}$) and aurein 1.2-+36 GFP (aurein 1.2-+36 $GFP^{Dex}$) were generated via sortase-mediated conjugation. Conjugated to these proteins, $S^{Dex}$ is no longer cell permeable and cannot activate the GR for nuclear translocation unless the protein-$S^{Dex}$ conjugate can access the cytosol. Treatment of HeLa cells expressing GR-mCherry with 1 μM aurein 1.2-+36 $GFP^{Dex}$ for 30 min resulted in a TR of 2.62, which was significantly greater (p<0.05) than that of +36 $GFP^{Dex}$ (TR=2.23). As positive controls, these cells were treated with canonical cell permeable peptides ($Tat^{Dex}$ and $Arg8^{Dex}$ (SEQ ID NO: 102)) and miniature proteins containing a penta-Arg motif that reach the cytosol intact, with efficiencies exceeding 50% ($5.3^{Dex}$ and ZF $5.3^{Dex}$) (LaRochelle, J. R.; et al. *Journal of the American Chemical Society* 2015, 137, 2536). Aurein 1.2-+36 $GFP^{Dex}$ (TR=2.62), activated significantly greater levels of GR-mCherry translocation (p<0.001) than $Tat^{Dex}$ (TR=1.87) and $Arg8^{Dex}$ (SEQ ID NO: 102) (TR=1.63) and similar levels evoked by miniature proteins $5.3^{Dex}$ (TR=2.62) and ZF $5.3^{Dex}$ (TR=2.38) (FIGS. 17A and 17B). Taken together, these results evidence that aurein 1.2-+36 $GFP^{Dex}$ exhibits an improved ability to access the cytoplasm over +36 $GFP^{Dex}$ and canonical cell permeable peptides.

As an additional, independent assay of non-endosomal protein delivery, the ability of aurein 1.2 to enhance the nonendosomal delivery of an evolved biotin ligase (BirA) enzyme was tested (Howarth, M.; Ting, A. Y. *Nature protocols* 2008, 3, 534). BirA catalyzes the biotinylation of a 15-amino acid acceptor peptide (AP). A mCherry-AP fusion plasmid was transfected into HeLa cells. Biotinylation of mCherry can only occur in the presence of cytosolic BirA. To assess the non-endosomal delivery of +36 GFP-BirA protein, mCherry-AP biotinylation was quantified by Western blot using fluorophore-labeled streptavidin and normalized to the mCherry signal. Treatment with 250 nM aurein 1.2-+36 GFP-BirA resulted in a 50% increase in biotinylation signal compared with 250 nM of +36 GFP-BirA alone. A dose-dependent increase in AP-biotinylation across treatment concentrations (250 nM, 500 nM, and 1 µM) for both aurein 1.2-(+36GFP)-BirA and unfused +36 GFP-BirA constructs was observed. These results are consistent with the results of the GR translocation assay, and further evidence that aurein 1.2 enhances the endosomal escape of superpositively charged proteins.

In order to directly quantify the increase in non-endosomal delivery resulting from aurein 1.2, a cytosolic fractionation experiment was performed to calculate the cytosolic concentrations of delivered protein. HeLa cells were treated with +36 GFP or aurein 1.2-+36 GFP at 250 nM, 500 nM, and 1 µM. After 30 min of treatment, cells were washed, homogenized, and fractionated by ultracentrifugation. The cytosolic concentration of delivered protein was calculated from the GFP fluorescence of the cytosolic fraction together with a standard curve relating fluorescence to known concentrations of +36 GFP and aurein 1.2-+36 GFP added to cytosolic extract. At 250 nM, treatment with aurein 1.2-+36 GFP resulted in ~5-fold more delivered cytosolic protein than treatment with +36 GFP alone. This difference decreased with increasing protein concentration, likely due to the influence of alternate uptake pathways or delivery bottlenecks at high protein concentrations. In contrast, the total amount of aurein 1.2-+36GFP versus +36 GFP taken up by cells was similar, with aurein 1.2-+36 GFP showing 1.3-fold higher total cellular uptake at 250 nM. These results directly demonstrate that aurein 1.2 increases the cytosolic concentration of cationic proteins that enter cells predominantly through endosomes (McNaughton, B. R.; et al. *Proceedings of the National Academy of Sciences* 2009, 106, 6111; Thompson, David B.; et al. *Chemistry & Biology* 2012, 19, 831) and are consistent with the above findings that aurein 1.2 has the greatest effect on enhancing non-endosomal delivery at ~250 nM (FIG. 15A).

Effect of Endocytic Inhibitors on +36 GFP and Aurein 1.2-+36 GFP Delivery.

Figure 17C:
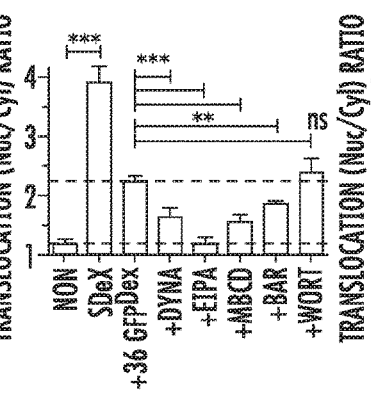
Figure 17D:
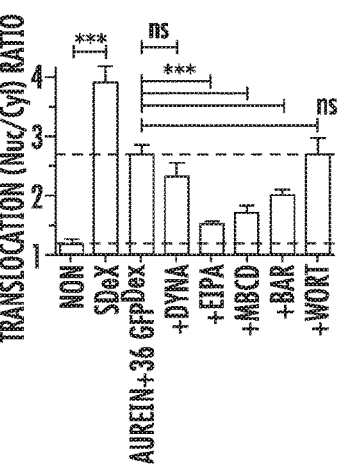

Endocytosis plays a key role in the cytosolic delivery of superpositively charged proteins (Thompson, David B.; et al. *Chemistry & Biology* 2012, 19, 831). To probe the role of endocytosis in the delivery of supercharged proteins with or without aurein 1.2, cells expressing GR-mCherry were treated with either +36 GFP$^{Dex}$ or aurein 1.2-+36GFP$^{Dex}$ in the presence of known endocytic inhibitors. The cortical actin remodeling inhibitor N-ethyl-isopropyl amiloride (EIPA), the cholesterol-sequestering agent methyl-β-cyclodextrin (MBCD), and the endosomal vesicular ATPase inhibitor bafilomycin (Baf) all strongly reduced the ability of both proteins to stimulate GRmCherry translocation. Blocking maturation of Rab5$^+$ vesicles by treatment with the phosphatidylinositol 3-kinase inhibitor wortmannin (Wort) did not influence reporter translocation of either +36 GFP$^{Dex}$ or aurein 1.2-+36GFP$^{Dex}$ (FIGS. 17C and 17D). In contrast, treatment with the small-molecule dynamin II inhibitor Dynasore (Dyna) significantly suppressed the ability of +36 GFP$^{Dex}$ to stimulate GR-mCherry translocation (TR=1.64) (FIG. 17C) but had little influence on the cytosolic delivery of aurein 1.2-+36GFP$^{Dex}$ (TR=2.30) (FIG. 17D). Taken together, these results evidence that active endocytosis is required for uptake of +36 GFP and aurein 1.2-+36GFP into the cell interior, and that the two proteins may traffic differently into the cell interior.

Aurein 1.2 can Greatly Increase Protein Delivery Efficiency In Vivo.

To evaluate the ability of aurein 1.2 to increase the efficacy of cationic protein delivery in vivo, proteins were delivered to the inner ear of Cre reporter transgenic mice that express tdTomato upon Cre-mediated recombination. This animal model was chosen due to its confined injection volume, the presence of well-characterized cell types, and the existence of genetic deafness models that would facilitate future studies of protein delivery to treat hearing loss. +36 GFP-Cre alone can be delivered to mouse retina (Cronican, J. J.; et al. *ACS Chemical Biology* 2010, 5, 747), albeit resulting in only modest levels of recombination consistent with inefficient endosomal escape.

Figure 18A:
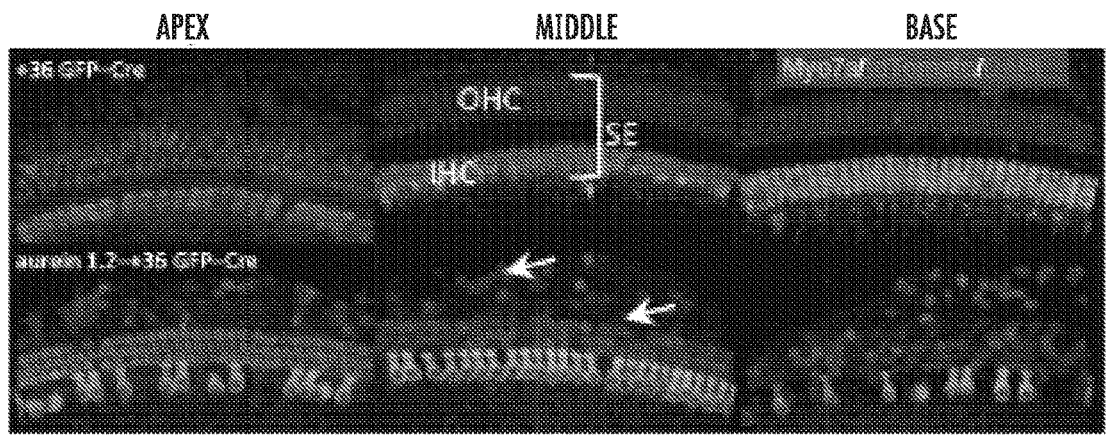
FIGS. 18A-18C show the results from the in vivo protein delivery of Cre recombinase into mouse neonatal cochleas. 0.4 µL of 50 µM+36 GFP-Cre or aurein 1.2-+36 GFP-Cre were injected into the scala media.
Figure 18B:
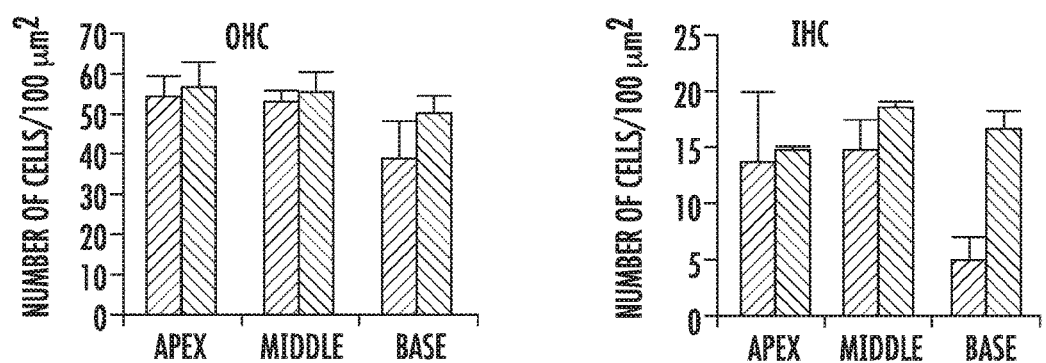
Figure 18C:
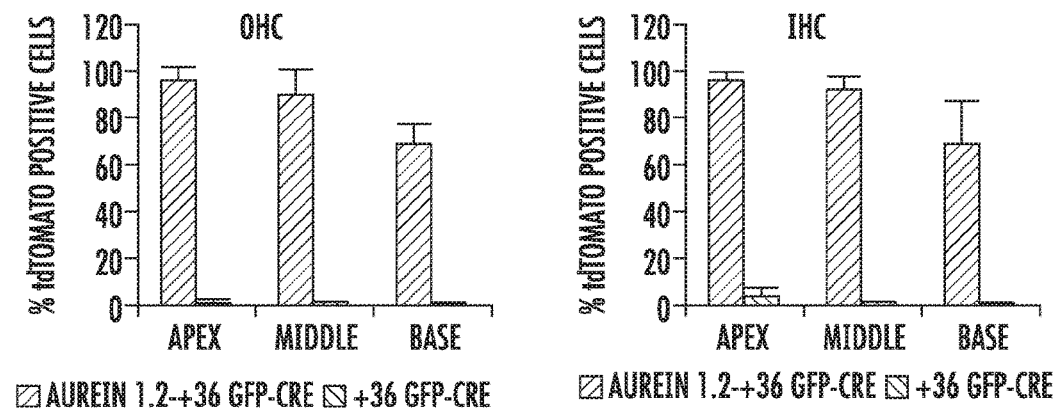

Anesthetized postnatal day 2 (P2) mice were injected with 0.4 µL of 50 µM +36 GFP-Cre or aurein 1.2-+36 GFP-Cre solutions in the scala media to access the cochlear cells. Five days after injection, the cochleas were harvested for immunolabeling of inner ear cell markers and imaging for tdTomato florescence (FIG. 18A). Both the hair cells (Myo7a+) and supporting cells (Myo7a−) were evaluated for td Tomato signal. The total number of hair cells and supporting cells (by DAPI labeling) in the sensory epithelium (SE) was used to determine the relative toxicity of aurein 1.2-+36 GFP-Cre to the baseline treatment of +36 GFP-Cre (FIG. 18A). Overall, an average of 96%, 92% and 66% of cochlear cells survived aurein 1.2-+36 GFP-Cre treatment as compared to +36 GFP-Cretreatment in the apex, middle, and base tissue samples, respectively (FIG. 18A). +36 GFP-Cre treatment resulted in low levels of recombination only in inner hair cells (IHC) of the apex of the cochlea (4.4%) but not in the middle or base of the cochlear hair cells or any cochlear supporting cells. In contrast, treatment with aurein 1.2-+36 GFP-Cre resulted in very high Cre-mediated recombination levels throughout the apex, middle, and base samples of outer hair cells (OHC) (96%, 91%, and 69%, respectively), inner hair cells (100%, 94%, and 70%, respectively), as well as supporting cells (arrows) (FIGS. 18A and 18C).

The observed levels of recombination in the inner hair cells from aurein 1.2-+36 GFP-Cre are comparable to that of adeno-associated virus type 1 (AAV1) gene transfection (Akil, O.; et al. *Neuron* 2012, 75, 283). For outer hair cells, it similar levels of recombination was previously shown using liposome-mediated delivery of supernegatively-charged GFP-Cre (Zuris, J. A.; et al. *Nat Biotech* 2015, 33, 73). The aurein 1.2-+36 GFP-Cre delivery system is the only method that showed significant recombination levels in both inner and outer hair cells (Akil, O.; et al. *Neuron* 2012, 75, 283; Taura, A.; et al. *Neuroscience* 2010, 166, 1185), and does not require any virus or other molecules beyond a single polypeptide. Significantly, aurein 1.2-+36 GFP-Cre also extended delivered recombinase activity to additional cochlear supporting cells. These results evidence that the aurein 1.2-+36 GFP-Cre delivery system to be a promising method for in vivo protein delivery into both hair cells and supporting cells of the inner ear (Izumikawa, M.; et al. *Nature Medicine* 2005, 11, 271).

Discussion

A 13-residue peptide, aurein 1.2, was discovered that can increase the efficiency of non-endosomal protein delivery by screening a panel of known membrane-active peptides. The results from a small screen of 22 peptides are consistent with our hypothesis that some peptides can selectively disrupt the endosomal membrane without disrupting the mammalian cell membrane. The effectiveness of aurein 1.2 is highly dependent on its sequence, as several other closely related peptides did not enhance protein delivery (Tables 1 and 2). Subtle differences in amino acid composition led to dramatic changes in membrane activity among peptides tested, highlighting the difficulty of rationally designing peptides that enhance non-endosomal delivery. Moreover, the lack of correspondence between peptide cationic charge and non-endosomal delivery efficiency evidences that aurein 1.2 does not enhance non-endosomal delivery simply by promoting endocytosis. While none of the tested variants of aurein 1.2 substantially outperformed the original peptide, several amino acids were identified that could be altered without loss of activity. These findings also provide a starting point for further optimization to discover next-generation endosomolytic peptides with improved efficacy and reduced toxicity.

Four independent assays for non-endosomal protein delivery (Cre recombination, GR translocation, BirA activity on a cytoplasmic peptide, and cytosolic fractionation), together with the peptide mutational studies described above, collectively evidence that aurein 1.2-fusion enhances endosomal escape of superpositively charged proteins. Moreover, these assays collectively demonstrated the ability of aurein 1.2 to mediate the non-endosomal delivery of +36 GFP fused to different proteins (or small molecules), evidences that aurein 1.2 facilities endosomal escape.

The in vivo protein delivery experiments described above revealed dramatic increases in non-endosomal functional Cre recombinase delivery into the diverse inner ear cell types including hair cells and supporting cells of live mice upon fusion with aurein 1.2. Indeed, aurein 1.2-fused +36 GFP-Cre construct resulted in highly efficient recombination levels across the main cochlear sensory epithelial cell classes studied in this work, all but one of which were unaffected by +36 GFP-Cre treatment. Taken together, these results evidence that aurein 1.2 is a 13-residue, potent, genetically encodable, endosome escape-enhancing peptide that can greatly increase the efficiency of non-endosomal cationic protein delivery in vitro and in vivo without requiring the use of additional components beyond the protein of interest.

What is claimed is:

1. A chimeric molecule comprising at least one gene editing agent fused, complexed or linked to at least one guide RNA (gRNA) wherein the at least one gRNA is targeted to a Pmca2 genomic nucleic acid sequence.

2. The chimeric molecule of claim 1, wherein the at least one gene editing agent comprises Cre recombinases, CRISPR/Cas molecules, TALE transcriptional activators, Cas9 nucleases, nickases, transcriptional regulators or combinations thereof.

3. The chimeric molecule of claim 1, wherein the chimeric molecule is encapsulated in a cationic lipid formulation.

4. The chimeric molecule of claim 2, wherein the at least one gene editing agent comprises CRISPR/Cas molecules.

* * * * *

UNITED STATES PATENT AND TRADEMARK OFFICE
CERTIFICATE OF CORRECTION

PATENT NO. : 10,258,697 B2
APPLICATION NO. : 15/523325
DATED : April 16, 2019
INVENTOR(S) : Zheng-Yi Chen et al.

It is certified that error appears in the above-identified patent and that said Letters Patent is hereby corrected as shown below:

On the Title Page

Item (72) (Inventors), after "David B. Thompson, Cambridge, MA (US)", insert -- Margie Li, Cambridge, MA (US) --

Signed and Sealed this
Twenty-second Day of August, 2023

Katherine Kelly Vidal
*Director of the United States Patent and Trademark Office*